US007056714B2

(12) United States Patent
Rosazza et al.

(10) Patent No.: US 7,056,714 B2
(45) Date of Patent: Jun. 6, 2006

(54) CARBOXYLIC ACID REDUCTASE POLYPEPTIDE, NUCLEOTIDE SEQUENCE ENCODING SAME AND METHODS OF USE

(75) Inventors: John P. Rosazza, Iowa City, IA (US); Ian Fotheringham, Edinburgh (GB); Tao Li, Union, NJ (US); Lacy Daniels, Iowa City, IA (US); Aimin He, Iowa City, IA (US)

(73) Assignee: University of Iowa Research Foundation, Inc., Iowa City, IA (US)

( * ) Notice: Subject to any disclaimer, the term of this patent is extended or adjusted under 35 U.S.C. 154(b) by 128 days.

(21) Appl. No.: 10/386,329

(22) Filed: Mar. 11, 2003

(65) Prior Publication Data

US 2004/0180400 A1   Sep. 16, 2004

(51) Int. Cl.
| | |
|---|---|
| *C12N 9/02* | (2006.01) |
| *C12N 1/20* | (2006.01) |
| *C12N 15/00* | (2006.01) |
| *C12P 21/04* | (2006.01) |
| *C12Q 1/26* | (2006.01) |
| *C12Q 1/00* | (2006.01) |
| *C07H 21/04* | (2006.01) |

(52) U.S. Cl. .............................. 435/189; 435/4; 435/6; 435/69.1; 435/71.1; 435/252.3; 435/320.1; 435/252.33; 435/440; 435/25; 536/23.2; 536/23.7

(58) Field of Classification Search ................ 435/189, 435/252.3, 320.1, 252.33, 69.1, 71.1, 4, 6, 435/440, 25; 536/23.2, 23.7, 23.5
See application file for complete search history.

(56) References Cited

U.S. PATENT DOCUMENTS

| 5,795,759 A | 8/1998 | Rosazza et al. |
| 6,261,814 B1 | 7/2001 | Rosazza et al. |

OTHER PUBLICATIONS

Kita et al. Cloning of the aldehyde reductase gene from a red yeast, Sporobolomyces salmonicolor, and characterization of the gene and its product. Appl Environ Microbiol. Jul. 1996;62(7):2303-10.*

* cited by examiner

*Primary Examiner*—Ponnathapu Achutamurthy
*Assistant Examiner*—Yong D. Pak
(74) *Attorney, Agent, or Firm*—McKee, Voorhees & Sease, P.L.C.

(57) ABSTRACT

The invention provides the nucleotide sequence and amino acid sequence for the enzyme carboxylic acid reductase isolated from bacteria. Expression cassettes, vectors, transformed cells, and variants are also provided as methods for use of recombinant biocatalytic reagents in production of synthetic, aromatic, aliphatic and alicyclic aldehydes and alcohols.

8 Claims, 8 Drawing Sheets

Figure 1

```
Nocardia    1   --AMDSPDERLQRRIAQLFAEDEQVKAARPLEAVSAAVSAPGMRLAQIAATVMAGYADRP
MtfadD      1   ---MSINDQRLTRRVEDLYASDAQFAAASPNEAIIQAIDQPGVALPQLIRMVMEGYADRP
MBCG        1   ---MSINDQRLTRRVEDLYASDAQFAAASPNEAIIQAIDQPGVALPQLIRMVMEGYADRP
MlAcS       1   MSTITKQEKQLARRVDDLTANDPQFAAAKPDPAVAAAIAQPGIRLPQIIQTALDGYAERP
Msmeg       1   -MTIETREDRFNRRIDHLFETDPQFAAARPDEAISAAAADPEIRLEAAVKQILAGYADRP
consensus   1        v   d rl RRie Lfa D QfaAA P eAvs Av   Pgm Lpqii   vm GYAdRP Nocardia    59  AAGQRAFELNTDDATGRTSPRLLPRFETITYRELWQRVGEVAAAWHHDPENPLRAGDFVA
MtfadD      58  ALGQRALRFVTDPDSGRTMVELLPRFETITYRELWARAGTLATALSADP--AIRPGDRVC
MBCG        58  ALGQRALRFVTDPDSGRTMVELLPRFETITYRELWARAGTLATALSADP--AIRPGDRVC
MlAcS       61  ALGQRVAEFTKDPKIGRTSMELLPSFETITYRQLGDRVGALARAWRHE---LLHAGYRVC
Msmeg       60  ALGKRAVEFVTD-EEGRTTAKLLPRFDTITYRQLAGRIQAVTNAWHNH---PVNAGDRVA
consensus   61  AlGqRa   f  tD  tGRT l LLPrFeTITYR L   R g va A    d   lr GdrV Nocardia    119 ILGFTSIDYATIDIADIHLGAVIVPLQASAAVSQLIAILTETSPRLIASTPEHLDAAVEC
MtfadD      116 VLGFNSVDYTTIDIALIRLGAVSVPLQTSAPVIGLRPIVTETEPTMIATSIDNLGDAVEV
MBCG        116 VLGFNSVDYTTIDIALIRLGAVSVPLQTSAPVIGLRPIVTETEPTMIATSIDNLGDAVEV
MlAcS       118 VLGFNSVDYAIIDMALGVIGAVAVPLQTSAAITQLQSIVTETEPSMIAISVNQLPDTVEL
Msmeg       116 ILGFTSVDYTTIDIALLELGAVSVPLQTSAPVAQLQPIVAETEPKVIASSVDFLADAVAL
consensus   121 lLGF SvDY tiDlAli lGAVtVPLQtSA vs L  IvtETeP liAssie L daVev Nocardia    179 LLAGTTPERLVVFDYHPEDDDQRAAFESARRRLADAGSSVIVETLDAMRARGRDLPAAPL
MtfadD      176 EAG-HAPARLVVFDYHGKVDTHREAVEAARARLAG---SVTIDTLAELIERGRALPAT--
MBCG        176 EAG-HAPARLVVFDYHGKVDTHREAVEAARARLAG---SVTIDTLAELIERGRALPAT--
MlAcS       178 ILSGQAPAKLVVFDYHPEVDEQHDAVATARARLADS--SVVVESLTEVLGRGKTLPATPI
Msmeg       176 VESGPAPSRLVVFDYSHEVDDQRIAFEAAKGKLAGT--GVVVETITDALDRGRSLADAP-
consensus   181 l    aP rLVVFDYh  vD  reA e ArarLA    sV vetl evi RGr Lpa Nocardia    239 FVPDTDDDPLALLIYTSGSTGTPKGAMYTNRLAATMWQG---NSMLQGNSQRVGINLNYM
MtfadD      230 PIADSADDALALLIYTSGSTGAPKGAMYRESQVMSFWRK---SSGWFEPSGYPSITLNFM
MBCG        230 PIADSADDALALLIYTSGSTGAPKGAMYRESQVMSFWRK---SSGWFEPSGYPSITLNFM
MlAcS       236 PMADDSADPLALLIYTSGSTGAPKGAMYLQSNVGKMWRR---SDGNWFGPTAASITLNFM
Msmeg       233 LYVPDEADPLTLLIYTSGSTGTPKGAMYPESKTAIMWQAGSKARWDETLGVMPSITLNFM
consensus   241   v  d    D LaLLIYTSGSTG PKGAMY   s    t W                  sItLNfM Nocardia    296 PMSHIAGRISLFGVLARGGTAYFAAKSDMSTLFEDIGLVRPTEIFFVPRVCDMVFQRMQS
MtfadD      287 PMSHVGGRQVLYGTLSNGGTAYFVAKSDLSTLFEDLALVRPTELCFVPRIWDMVFAEYHS
MBCG        287 PMSHVGGRQVLYGTLSNGGTAYYVAKSDLSTLFEDLALVRPTELCFVPRIWDMVFAEYHS
MlAcS       293 PMSHVMGRGILYGTLGNGGTAYFAARSDLSTLLEDIKLVRPTELNFVPRIWETLYDESKR
Msmeg       293 PMSHVMGRGILCSTLASGGTAYFAARSDLSTFLEDLALVRPTQLNFVPRIWDMIFQEYQS
consensus   301 PMSHv GR vLfgtL  GGTAYf AkSDlSTl EDlgLVRPTel FVPRiwdmvf ey s Nocardia    356 EEDRRSVAG---ADLDTEDREVKADIIRQNYLGGRFLVAVVGSAPLAAEMKTFMES-VLDLP
MtfadD      347 EVDRRLVDG---ADRAAEEAQVKAELRENVLGGRFVMALTGSAPISAEMTAWVESLLADVH
MBCG        347 EVDRRLVDG---ADRAAEEAQVKAELRENVLGGRFVMALTGSAPISAEMTAWVESLLADVH
MlAcS       353 AVDRRLANSGSADRAAEIKAEVMDEQRQSLLGGRVIAAMTGSAPTSPELKHGVES-LLEMH
Msmeg       353 RIDNRRAEG---S-EDRAEEAVLEEVRTQLLGGRFVSALTGSAPISAEMKSWVED-LLDMH
consensus   361  lDrR   g   ad   lda V  elR nvLGGRfl AvtGSAPlsaEm    fvEs  l dlh Nocardia    413 LHDGYGSTEAGASVLLDNQIQRPPVIDYKLVDVPELGYFRTDRPHPRGELLLKAETTIPG
MtfadD      405 LVEGYGSTEAG-MVLNDGMVRRPAVIDYKLVDVPPLGYFGTDQPYPRGELLVKTQTMFPG
MBCG        405 LVEGYGSTEAG-MVLNDGMVRRPAVIDYKLVDVPPLGYFGTDQPYPRGELLVKTQTMFPG
MlAcS       412 LVEGYGSTEAG-MVLFDGEVQRPPVIDYKLVDVPBLGYFGSTDQPYPRGELLLKTQNMFPG
Msmeg       409 LIEGYGSTEAG-AVFIDGQIQRPPVIDYKLVDVPDLGYFATDRPYPRGELLLKSEQMFPG
consensus   421 LveGYGSTEAG  Vl Dg i RP ViDYKLVDVPeLGYF TD PyPRGELLlKt  mfPG
```

```
Nocardia   473 YYKRPEVTAEIFDEDGFYKTGDIMAELEHDRLVYVDRRNNVLKLSQGEFVTVAELEAVFA
MtfadD     464 YYQRPDVTAEVFDPDGFYRTGDIMAKVGPDQFVYEDRRNNVLKLSQGEFIAVSKLEAVFG
MBCG       464 YYQRPDVTAEVFDPDGFYRTGDIMAKVGPDQFVYEDRRNNVLKLSQGEFIAVSKLEAVFG
MlAcS      471 YYKRPEVTATVFDSDGYYQTGDIMAEVGPDRLVYVDRRNNVLKLAQCQFVTVAKLEAAFS
Msmeg      468 YYKRPEITAEMFDEDGYYRTGDIMAELGPDHLEYEDRRNNVLKLSQGEFVTVSKLEAVFG
consensus  481 YY RPevTAeiFD DGfYkTGDIvA lgpD  vYvDRRNNVLKLsQGeFv V kLEAvFa Nocardia   533 SSPLVRQIFIYGSSERSYLLAVIVPTDDALRGRDTATLKSALAESIQRIAKDANLQEYEI
MtfadD     524 DSPLVRQIFIYGNSARAYPLAVVVPSGDALSRHGIENLKPVISESLQEVARAAGLQSYEI
MBCG       524 DSPLVRQIFIYGNSARAYPLAVVVPSGDALSRHGIENLKPVISESLQEVARAAGLQSYEI
MlAcS      531 NSPLVRQIYIYGNSAHPYLLAVVVPTEDALATNDIEVLKPLIIDSLQKVAKEADLQSYEV
Msmeg      528 DSPLVRQIYVYGNSARSYLLAVVVPTEEALSRWDGDELKSRISDSLQDAARAAGLQSYEI
consensus  541  SPLvRQIfiYGnSar Y LAVvVPt dAL    e LK i eSlQ iAk A LQsYEi Nocardia   593 PRDFLIETEPFTIANGLLSGIAKLRPNLKERYGAQLEQMYTDLATGQADELLALRRBAA
MtfadD     584 PRDFLIETTPFTLENGLLTGIRKLARPQLKKFYGERLERLYTELADSCSNELRELRQSCP
MBCG       584 PRDFLIETTPFTLENGLLTGIRKLARPQLKKFYGERLERLYTELADSCSNELRELRQSCP
MlAcS      591 PRDLLVETTPFSLENGLLTGIRKLAWPKLKQHYGARLEQLYADLVEGCANALHVLKQSVA
Msmeg      588 PRDFLVETTPFTLENGLLTGIRKLARPKLKAHYGERLEQLYTDLAEGCANELRELRRNCA
consensus  601 PRDfliETtPFtleNGLLtGIrkLarP LK  YG rLE lYtdLad Q neLr Lr   a Nocardia   653 DLPVIETVSRAAKAMLGVASADMRPDAHFTDLGGDSLSALSFSNLLHEIFGVEVPVGVMV
MtfadD     644 DAPVLPTICRAAAALLGSTAADVRPDAHFADLGGDSLSALSLANLLHEIFGVDVPVGVIV
MBCG       644 DAPVLPTICRAAAALLGSTAADVRPDAHFADLGGDSLSALSLANLLHEIFGVDVPVGVIV
MlAcS      651 NAPVLQTVSRAVGTELGVATTDLPSNAHFTDLGGDSLSALIFGSLLRELFDIDVPVGVIV
Msmeg      648 DRPVVETVSRAAVALLGASVTDLRSDAHFTDLGGDSLSALSFSNLLHEIFDVDVPVGVIV
consensus  661 d PVl Tv RAa amLG   Dmr dAHF DLGGDSLSALs  nLLhEiF vdPVGVIV Nocardia   713 SPANELRDIANYIEAERNSCAKRPTFTSVHG-GGSEIRAADLTLDKFIDARTLAAADSIP
MtfadD     704 SPASDLRAIADHIEAAR-TCVRRPSFASIHGRSATEVIASDLTLDKFIDAATLAAAPNLP
MBCG       704 SPASDLRAIADHIEAAR-TCVRRPSFASIHGRSATEVIASDLTLDKFIDAATLAAAPNLP
MlAcS      711 SPVNNLVAIADYIERER-QCTKRPIFIAIHGRDAGKVHASDLTLDKFIDVSTLTAAPVLA
Msmeg      708 SPATDLAGVEAYIEGEL-RCSKRPTYASVHGRDAIEVRARDLALGKFIDAKTLSAAPGLP
consensus  721 SPa eL alA  IEa r  G kRPtf svHGr asevrA DLtLdKFIDa  TL AAp lp Nocardia   772 HAPVPAQTVLLTGANGYLGREFLCLEWLERIDKTGGTVICVVRGSDAAAARKRLDSAFDSG
MtfadD     763 APSAQVRTVLLTGATGFLGRYLALEWLDRMDLVNGKIICLVRARSDEEAQARLDATFDSG
MBCG       763 APSAQVRTVLLTGATGFLGRYLALEWLDRMDLVNGKIICLVRARSDEEAQARLDATFDSG
MlAcS      770 QPGTEVRTVLLTGATGFLGRYLALKWLERMDLVEGKVIALVRAKSNEDARARLDKTFDSG
Msmeg      767 RSGTEIRTVLLTGATGFLGRYLALEWLERMDLVDGKMICLVRARSDDEARARLDATFDTG
consensus  781      vrTVLLTGAtGfLGRyLaLeWLeRmDlv GklIclVRars eeA aRLD tFDSG Nocardia   832 DPGLLEHYQQLAARTLEVIAGDIGDPNLGLDDATWQRLAETVDLIVHPAALVNHVLPYTQ
MtfadD     823 DPYLVRHYRELGAGRLEVIAGDKGEADLGLDRVTWQRLADTVDLIVDPAALVNHVLPYSQ
MBCG       823 DPYLVRHYRELGAGRLEVIAGDKGEADLGLDRVTWQRLADTVDLIVDPAALVNHVLPYSQ
MlAcS      830 DPKLLAHYQELATDELEVIAGDKGEVDLELDRQTWRRLADTVDLIVDPAALVNHVLPYSE
Msmeg      827 DATLLEHYRALAADHLEVIAGDKGEADLGLDHDTWQRLADTVDLIVDPAALVNHVLPYSQ
consensus  841 Dp Ll HY  Laa rLEVlAGDkGe dLgLDr TWqRLAdTVDLIVdPAALVNHVLPYsq Nocardia   892 LFGPNVVGTAEIVRIAITARRKPVTYLSTVGVADQVDPAEYQEDSDVREMSAVRVVRESY
MtfadD     883 LFGPNAAGTAELLRIALTGKRKPYIYTSTIAVGEQIPPEAFTEDADIRAISPTRRIDDSY
MBCG       883 LFGPNAAGTAELLRIALTGKRKPYIYTSTIAVGEQIPPEAFTEDADIRAISPTRRIDDSY
MlAcS      890 LFGPNTLGTAELLRIALTSKQKPYIYVSTIGVGNQIEPAKFTEDSDIRVISPTRRINNNV
Msmeg      887 MFGPNALGTAELLRIALTTIKPYIYVSTIGVGQGISPEAFVEDADIREISATRRMDDSY
consensus  901 lFGPN GTAElvRlAlT r KPyiY STigVg qi P  f ED DiR iS tR v esY
```

```
Nocardia   952  ANGYGNSKWAGEVLLREAHELCGLPVAVFRSDMILAHSRYAGQLNMQDVFTRLILSLVAT
MtfadD     943  ANGYANSKWAGEVLLREAHEQCGLPVTVFRCDMILADTSYTGQLNLPDMFTRLMLSLAAT
MBCG       943  ANGYANSKWAGEVLLREAHEQCGLPVTVFRCDMILADTSYTGQLNLPDMFTRLMLSLAAT
MlAcS      950  ANGYGNSKWAGEVLLREAHELCGLPVTVFRCDMILADTSYAGQLNMPDMFTRMMLSLAAT
Msmeg      947  ANGYGNSKWAGEVLLREAHDWCGLPVSVFRCDMILADTTYSGQLNLPDMFTRLMLSLVAT
consensus  961  ANGYgNSKWAGEVLLREAHd CGLPVtVFRcDMILAdtsY GQLNvpDmFTRlmLSL AT Nocardia   1012 GIAPYSFYRTDADCNRQRAHYDGLPADFTAAAITALG---IQATEGFRTYDVLNPYDDGI
MtfadD     1003 GIAPGSFYELDAHGNRQRAHYDGLPVEFVAEAICTLG---THSPDRFVTYHVMNPYDDGI
MBCG       1003 GIAPGSFYELDAHGNRQRAHYDGLPVEFVAEAICTLG---THSPDRFV------------
MlAcS      1010 GIAPGSFYELDAESNRQRAHYDGLPVEFIAEAISTLGDQSLHDRDGFTTYHVMNPDDDGI
Msmeg      1007 GIAPGSFYELDADGNRQRAHYDGLPVEFIAEAISTLG---SQVTDGFETRHVMNPYDDGI
consensus  1021 GIAPgSFYelDA gNRQRAHYDGLPveFvAeAI tlG        d F ty vlnp ddgi Nocardia   1069 SDDEFVDWLVESG----HPIQRITDYSDWFHRFETAIRALPEKQRQASVLPLLDAMRNEC
MtfadD     1060 GLDEFVDWLNSPTSGSGCTIQRIADYGEWLQRFETSLRALPDRQRHASLLPLLHNYREEA
MBCG            ------------------------------------------------------------
MlAcS      1070 GMDEFVDWLID----AGCPIQRINDYDEWLRRFEISLRALPERQRHSSILPLLHNYQKEE
Msmeg      1064 GLDEFVDWLIEAG----YPVHRMDDYATWLSRFETALRALPERQRQASLLPLLHNYQQES
consensus  1081      ldefvdwl        i ri dy  w   rfe  iralpekqr  svlpll  y  p Nocardia   1125 PAVRCAILPAKEEQAAVQTAKIGPEQDIPHLSAPIIDKYVSDLELLQLL  SEQ ID NO:2
MtfadD     1120 KPICCGSTAPTDQFRAAVQEAKIGPDKDIPHLAAIIAKYTSNLRLLGLL  SEQ ID NO:32
MBCG            ------------------------------------------------  SEQ ID NO:33
MlAcS      1126 KPIHGSIAPTIRERTAVQNANIGQDKDIPHLSPAILAKYVSDLQLLGLV  SEQ ID NO:34
Msmeg      1120 PPVCGAVALTDREFAAVQDAKIGPDKDIPHVIADMIVKYISNLQMLGLL  SEQ ID NO:35
consensus  1141    v   g i p   f   avq a ig e diphls   li kyvs l ll ll  SEQ ID NO:36
```

Figure 3

| | | |
|---|---|---|
| Car-C | LIYTSGSTGTPKGAMY | SEQ ID NO:40 |
| FadD9 | LIYTSGSTGAPKGAMY | SEQ ID NO:41 |
| yeast AAR | LSFTSGSEGIPKGVLG | SEQ ID NO:42 |
| motif-Pc | ---TSGSEGRPKG--- | SEQ ID NO:43 |
| consensus | l yTSGS G PKG m | SEQ ID NO:44 |
| | | |
| Car-D | DLPLHDGYGSTEAG | SEQ ID NO:45 |
| FadD9 | DVHLVEGYGSTEAG | SEQ ID NO:46 |
| yeast | NCRIVNMYGTTETQ | SEQ ID NO:47 |
| motif-Pc | ---IVNMYGTT--- | SEQ ID NO:48 |
| consensus | lv YGsTe | SEQ ID NO:49 |
| | | |
| Car-F | DEDGFYKTGDIVAE | SEQ ID NO:50 |
| FadD9 | DPDGFYRTGDIMAK | SEQ ID NO:51 |
| yeast | PRDRLYRTGDLGRY | SEQ ID NO:52 |
| motif-Pc | ---RLYRSGDL--- | SEQ ID NO:53 |
| consensus | d YrtGDl | SEQ ID NO:54 |
| | | |
| Car-H | DANLQPYEIPRDF- | SEQ ID NO:55 |
| FadD9 | AAGLQSYEIPRDF- | SEQ ID NO:56 |
| yeast | EPTLITFMVPR-FD | SEQ ID NO:57 |
| motif-Pc | ---LVSYFVP---- | SEQ ID NO:58 |
| consensus | L sy iPr f | SEQ ID NO:59 |
| | | |
| Car-I | NGLLSGIAKLLRPNLKER | SEQ ID NO:60 |
| FadD9 | NGLLTGIRKLARPQLKKF | SEQ ID NO:61 |
| yeast | KLPLNPNGKVDKPKLQFP | SEQ ID NO:62 |
| motif-Pc | ---LNPNGKIDKPAL--- | SEQ ID NO:63 |
| consensus | L gKv kP L | SEQ ID NO:64 |
| | | |
| Car-J | FTDLGGDSLSALSF | SEQ ID NO:65 |
| FadD9 | FADLGGDSLSALSL | SEQ ID NO:66 |
| yeast | FFDLGGHSILATKM | SEQ ID NO:67 |
| motif-Pc | ---LGGHSILAQ-- | SEQ ID NO:68 |
| consensus | f dLGG Si A | SEQ ID NO:69 |
| | | |
| Car-NADP | LLTGANGYLGRFL | SEQ ID NO:70 |
| FadD9 | LLTGATGFLGRYL | SEQ ID NO:71 |
| yeast | FVTGVTGFLGSYI | SEQ ID NO:72 |
| motif-Pc | ---GATGFLGAHI | SEQ ID NO:73 |
| consensus | vtGatGfLG yi | SEQ ID NO:74 |
| | | |
| Car-Reduct | YANGYGNSKWAGE | SEQ ID NO:75 |
| FadD9 | YANGYANSKWAGE | SEQ ID NO:76 |
| yeast | LTGGYGQSKWAAE | SEQ ID NO:77 |
| motif-Pc | ---GYGQSKW--- | SEQ ID NO:78 |
| consensus | GYgqSKWaae | SEQ ID NO:79 |

Fig. 4

```
AVDSPDERLQ  RRIAQLFAED  EQVKAARPLE  AVSAAVSAPG  MRLAQIAATV
MAGYADRPAA  GQRAFELNTD  DATGRTSLRL  LPRFETITYR  ELWQRVGEVA              100
AAWHHDPENP  LRAGDFVALL  GFTSIDYATL  DLADIHLGAV  TVPLQASAAV
SQLIAILTET  SPRLLASTPE  HLDAAVECLL  AGTTPERLVV  FDYHPEDDDQ              200
RAAFESARRR  LADAGSLVIV  ETLDAVRARG  RDLPAAPLFV  PDTDDDPLAL
LIYTSGSTGT  PKGAMYTNRL  AATMWQGNSM  LQGNSQRVGI  NLNYMPMSHI    C         300
AGRISLFGVL  ARGGTAYFAA  KSDMSTLFED  IGLVRPTEIF  FVPRVCDMVF
QRYQSELDRR  SVAGADLDTL  DREVKADLRQ  NYLGGRFLVA  VVGSAPLAAE              400
MKTFMESVLD  LPLHDGYGST  EAGASVLLDN  QIQRPPVLDY  KLVDVPELGY    D
FRTDRPHPRG  ELLLKAETTI  PGYYKRPEVT  AEIFDEDGFY  KTGDIVAELE    F         500
HDRLVYVDRR  NNVLKLSQGE  FVTVAHLEAV  FASSPLIRQI  FIYGSSERSY
LLAVIVPTDD  ALRGRDTATL  KSALAESIQR  IAKDANLQPY  EIPRDFLIET    H         600
EPFTIANGLL  SGIAKLLRPN  LKERYGAQLE  QMYTDLATGQ  ADELLALRRE    I
AADLPVLETV  SRAAKAMLGV  ASADMRPDAH  FTDLGGDSLS  ALSFSNLLHE    J         700
IFGVEVPVGV  VVSPANELRD  LANYIEAERN  SGAKRPTFTS  VHGGGSEIRA
ADLTLDKFID  ARTLAAADSI  PHAPVPAQTV  LLTGANGYLG  RFLCLEWLER    NADP bind. 800
LDKTGGTLIC  VVRGSDAAAA  RKRLDSAFDS  GDPGLLEHYQ  QLAARTLEVL
AGDIGDPNLG  LDDATWQRLA  ETVDLIVHPA  ALVNHVLPYT  QLFGPNVVGT              900
AEIVRLAITA  RRKPVTYLST  VGVADQVDPA  EYQEDSDVRE  MSAVRVVRES
YANGYGNSKW  AGEVLLREAH  DLCGLPVAVF  RSDMILAHSR  YAGQLNVQDV    Reduction 1000
FTRLILSLVA  TGIAPYSFYR  TDADGNRQRA  HYDGLPADFT  AAAITALGIQ
ATEGFRTYDV  LNPYDDGISL  DEFVDWLVES  GHPIQRITDY  SDWFHRFETA              1100
IRALPEKQRQ  ASVLPLLDAY  RNPCPAVRGA  ILPAKEFQAA  VQTAKIGPEQ              1150
DIPHLSAPLI  DKYVSDLELL  QLL  (SEQ ID NO:2)
```

Fig. 5

```
SINDQRLTRR VEDLYASDAQ FAAASPNEAI TQAIDQPGVA LPQLIRMVME
GYADRPALGQ RALRFVTDPD SGRTMVELLP RFETITYREL WARAGTLATA            100
LSAEPAIRPG DRVCVLGFNS VDYTTIDIAL IRLGAVSVPL QTSAPVTGLR
PIVTETEPTM IATSIDNLGD AVEVLAGHAP ARLVVFDYHG KVDTHREAVE            200
AARARLAGSV TIDTLAELIE RGRALPATPI ADSADDALAL LIYTSGSTGA      C
PKGAMYRESQ VMSFWRKSSG WFEPSGYPSI TLNFMPMSHV GGRQVLYGTL            300
SNGGTAYFVA KSDLSTLFED LALVRPTELC FVPRIWDMVF AEFHSEVDRR
LVDGADRAAL EAQVKAELRE NVLGGRFVMA LTGSAPISAE MTAWVESLLA            400
DVHLVEGYGS TEAGMVLNDG MVRRPAVIDY KLVDVPELGY FGTDQPYPRG      D
ELLVKTQTMF PGYYQRPDVT AEVFDPDGFY RTGDIMAKVG PDQFVYLDRR      F    500
NNVLKLSQGE FIAVSKLEAV FGDSPLVRQI FIYGNSARAY PLAVVVPSGD      H
ALSRHGIENL KPVISESLQE VARAAGLQSY EIPRDFIIET TPFTLENGLL            600
TGIRKLARPQ LKKFYGERLE RLYTELADSQ SNELRELRQS GPDAPVLPTL      I
CRAAAALLGS TAADVRPDAH FADLGGDSLS ALSLANLLHE IFGVDVPVGV      J    700
IVSPASDLRA LADHIEAART GVRRPSFASI HGRSATEVHA SDLTLDKFID
AATLAAAPNL PAPSAQVRTV LLTGATGFLG RYLALEWLDR MDLVNGKLIC         NADP
LVRARSDEEA QARLDATFDS GDPYLVRHYR ELGAGRLEVL AGDKGEADLG
LDRVTWQRLA DTVDLIVDPA ALVNHVLPYS QLFGPNAAGT AELLRLALTG            900
KRKPYIYTST IAVGEQIPPE AFTEDADIRA ISPTRRIDDS YANGYANSKW        Reduction
AGEVLLREAH EQCGLPVTVF RCDMILADTS YTGQLNLPDM FTRLMLSLAA           1000
TGIAPGSFYE LDAHGNRQRA HYDGLPVEFV AEAICTLGTH SPDRFVTYHV
MNPYDDGIGL DEFVDWLNSP TSGSGCTIQR IADYGEWLQR FETSLRALPD           1100
RQRHASLLPL LHNYREPAKP ICGSIAPTDQ FRAAVQEAKI GPDKDIPHLT           1150
AAIIAKYISN LRLLGLL (SEQ ID NO:32)
```

Fig. 6.

```
TNEKVWIEKL DNPTLSVLPH DFLRPQQEPY TKQATYSLQL PQLDVPHDSF
SNKYAVALSV WAALIYRVTG DDDIVLYIAN NKILRFNIQP TWSFNELYST        100
INNELNKLNS IEANFSFDEL AEKIQSCQDL ERTPQLFRLA FLENQDFKLD
EFKHHLVDFA LNLDTSNNAH VLNLIYNSLL YSNERVTIVA DQFTQYLTAA        200
LSDPSNCITK ISLITASSKD SLPDPTKNLG WCDFVGCIHD IFQDNAEAFP
ERTCVVETPT LNSDKSRSFT YRDINRTSNI VAHYLIKTGI KRGDVVMIYS        300
SRGVDLMVCV MGVLKAGATF SVIDPAYPPA RQTIYLGVAK PRGLIVIRAA
GQLDQLVEDY INDELEIVSR INSIAIQENG TIEGGKLDNG EDVLAPYDHY        400
KDTRTGVVVG PDSNPTLSFT SGSEGIPKGV LGRHFSLAYY FNWMSKRFNL  C
TENDKFTMLS GIAHDPIQRD MFTPLFLGAQ LYVPTQDDIG TPGRLAEWMS        500
KYGCTVTHLT PAMGQLLTAQ ATTPFPKLHH AFFVGDILTK RDCLRLQTLA
ENCRIVNMYG TTETQRAVSY FEVKSKNDDP NFLKKLKDVM PAGKGMLNVQ  D     600
LLVVNRNDRT QICGIGEIGE IYVRAGGLAE GYRGLPELNK EKFVNNWFVE
KDHWNYLDKD NGEPWRQFWL GPRDRLYRTG DLGRYLPNGD CECCGRADDQ  F     700
VKIRGFRIEL GEIDTHISQH PLVRENITLV RKNADNEPTL ITFMVPRFDK  H
PDDLSKFQSD VPKEVETDPI VKGLIGYHLL SKDIRTFLKK RLASYAMPSL        800
IVVMDKLPLN PNGKVDKPKL QFPTPKQLNL VAENTVSETD DSQFTNVERE
VRDLWLSILP TKPASVSPDD SFFDLGGHSI LATKMIFTLK KKLQVDLPLG  J     900
TIFKYPTIKA FAAEIDRIKS SGGSSQGEVV ENVTANYAED AKKLVETLPS
SYPSREYFVE PNSAEGKTTI NVFVTGVTGF LGSYILADLL GRSPKNYSFK  NADP bind. 1000
VFAHVRAKDE EAAFARLQKA GITYGTWNEK FASNIKVVLG DLSKSQFGLS
DEKWMDLANT VDIIIHNGAL VHWVYPYAKL RDPNVISTIN VMSLAAVGKP        1100
KFFDFVSSTS TLDTEYYFNL SDKLVSEGKP GILESDDLMN SASGLTGGYG
QSKWAAEYII RRAGERGLRG CIVRPGYVTG ASANGSSNTD DFLLRFLKGS  Reduction 1200
VQLGKIPDIE NSVNMVPVDH VARVVVATSL NPPKENELAV AQVTGHPRIL
FKDYLYTLHD YGYDVEIESY SKWKKSLEAS VIDRNEENAL YPLLHMVLDN        1300
LPESTKAPEL DDRNAVASLK KDTAWTGVDW SNGIGVTPEE VGIYIAFLNK        1350
VGFLPPPTHN DKLPLPSIEL TQAQISLVAS GAGARGSSAA A (SEQ ID NO:80)
```

CARBOXYLIC ACID REDUCTASE POLYPEPTIDE, NUCLEOTIDE SEQUENCE ENCODING SAME AND METHODS OF USE

BACKGROUND OF THE INVENTION

Microorganism-produced enzymes are widely used as a class of biocatalytic reagents in production of synthetic, aromatic, aliphatic and alicyclic aldehydes and alcohols are useful chemical intermediates in chemical, agrochemical, pharmaceutical and food industries. These enzymes are useful in a wide variety of reactions including, e.g., oxidations, reductions, hydrolyses, and carbon—carbon bond ligations.

Biocatalysts are valued for their intrinsic abilities to bind organic substrates and to catalyze highly specific and selective reactions under the mildest of reaction conditions. These selectivities and specificities are realized because of highly rigid interactions occurring between the enzyme active site and the substrate molecule. Biocatalytic reactions are particularly useful when they may be used to overcome difficulties encountered in catalysis achieved by the use of traditional chemical approaches.

Carboxylic acid reductases are complex, multicomponent enzyme systems, requiring the initial activation of carboxylic acids via formation of AMP and often coenzyme A intermediates (see, e.g., Hempel et al., Protein Sci. 2:1890–1900 (1993). Chemical methods for carboxylic acid reductions are generally poor usually requiring prior derivatization and product deblocking with multifunctional reactants.

An enzymatic reaction offers significant advantages over existing methods used in chemical reductions of carboxylic acids, or their derivatives. Unlike many substrates subjected to biocatalytic reactions, carboxylic acids are generally water soluble, rendering them of potentially broad application to this class of enzyme. The carboxylic acid reduction reaction appears to bear the usual desirable features of functional group specificity. It also functions well under mild reaction conditions and produces a high yield of product. The reduction of the activated carboxylic acid intermediate occurs step-wise to give aldehyde products (Gross et al., Eur. J. Biochem. 8:413–419; 420–425 (1969); Gross, Eur. J. Biochem. 31:585–592 (1972)).

The reduction of carboxylic acids by microorganisms is a relatively new biocatalytic reaction that has not yet been widely examined or exploited. Jezo and Zemek reported the reduction of aromatic acids to their corresponding benzaldehyde derivatives by Actinomycetes in Chem. Papers 40(2):279–281 (1986). Kato et al. reported the reduction of benzoate to benzyl alcohol by *Nocardia asteroides* JCM 3016 (Agric. Biol. Chem. 52(7):1885–1886 (1988)), and Tsuda et al. described the reduction of 2-aryloxyacetic acids (Agric. Biol. Chem. 48(5): 1373–1374 (1984)) and arylpropionates (Chem. Pharm. Bull. 33(11):4657–4661 (1985)) by species of *Glomerella* and *Gloeosporium*. Microbial reductions of aromatic carboxylic acids, typically to their corresponding alcohols, have also been observed with whole cell biotransformations by *Clostridium thermoaceticum* (White et al., Eur. J. Biochem. 184:89–96 (1989)), and by *Neurospora* (Bachman et al., Arch. Biochem. Biophys. 91:326 (1960)). More recently, carboxylic acid reduction reactions have reportedly been catalyzed by whole cell preparations of *Aspergillus niger, Corynespora melonis* and *Coriolus* (Arfmann et al., Z. Naturforsch 48c:52–57 (1993); cf., Raman et al., J. Bacterial 84:1340–1341 (1962)), and by *Nocardia asteroides* (Chen and Rosazza, Appl. Environ. Microbiol. 60(4):1292–1296 (1994)).

Biocatalytic reductions of carboxylic acids are attractive to traditional chemical catalysis because the substrates are water soluble, blocking chemistry is not necessary, reductions are enantioselective (7), and the scope of the reaction is very broad (23, 32).

Aldehyde oxidoreductases are also known as carboxylic acid reductases (CAR), require ATP, $Mg^{2+}$, and NADPH as cofactors during carboxylic acid reduction (15, 16, 20, 23). The reduction reaction is a stepwise process involving initial binding of both ATP and the carboxylic acid to the enzyme, to form mixed 5'-adenylic acid-carbonyl anhydride intermediates (8, 14, 24, 26, 40) that are subsequently reduced by hydride delivery from NADPH to form the aldehyde product (15, 24).

Aromatic carboxylic acid reductases have been purified to homogeneity only from *Neurospora* (16) and *Nocardia* (20, 23). Although details of N- and internal amino acid sequences have been reported for the *Nocardia asteroides* enzyme (23), complete gene sequences for these or any other carboxylic acid reductases are unknown.

It is an object of the present invention to provide a purified and isolated bacterial carboxylic acid reductase (CAR) gene and the protein encoded thereby.

It is yet another object of the invention to provide homologous nucleotide sequences and/or amino acid sequences which encode CAR.

It is yet another object of the invention to provide recombinant DNA using expression constructs, vectors, and recombinant cells using the sequences of the invention for production of recombinant CAR.

It is yet another object of the invention to provide for large scale production of and recovery of recombinant CAR, for use in production of synthetic, aromatic, aliphatic and alicyclic aldehydes and alcohols.

It is yet another embodiment of the invention to provide methods of synthesis of chemical compounds such as those for biocatalytically reducing a carboxylic acid, or a derivative thereof, to its corresponding aldehyde product(s), to provide a method of biocatalytically reducing a carboxylic acid, or a derivative thereof, to its corresponding intermediary by-product(s), as exemplified by acyl-AMP analogs, or to provide a method of biocatalytically reducing vanillic acid, or a precursor or derivative thereof, to vanillin, all using recombinant CAR as described the invention disclosed herein.

Additional objects, advantages and novel features of the invention will be set forth in part in the description which follows, and in part will become apparent to those skilled in the art on examination of the following, or may be learned by practice of the invention.

BRIEF SUMMARY OF THE INVENTION

The present invention provides polynucleotides, related polypeptides and all conservatively modified variants of purified and isolated CAR. The nucleotide sequence of CAR comprises the sequence found in SEQ ID NO: 1, 3, and 5. Sequences 3 and 5 provide examples of conservatively modified polynucleotides of SEQ ID NO: 1 and sequences 7, and 9, 11, are examples of sequences with 80, 90, and 95% sequence identity to SEQ ID NO:1 as also described herein.

Therefore, in one aspect, the present invention relates to an isolated nucleic acid comprising an isolated polynucleotide sequence encoding a CAR enzyme. In a further aspect, the present invention includes a nucleic acid selected from: (a) an isolated polynucleotide encoding a polypeptide of the present invention; (b) a polynucleotide having at least 80%, 90% or 95% identity to a polynucleotide of the present invention; (c) a polynucleotide comprising at least 25 nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (d).

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translation of the nucleic acid in a host cell. The present invention also relates to host cells able to express the polynucleotide of the present invention. A number of host cells could be used, such as but not limited to, microbial, mammalian, plant, or insect. In a preferred embodiment the host cell is a bacterial cell. In a more preferred embodiment the bacterial host cell is *E. Coli*. Thus the invention is also directed to transgenic cells, containing the nucleic acids of the present invention as well as cells, strains and lines derived therefrom.

This invention also provides an isolated polypeptide comprising (a) a polypeptide comprising at least 80%, 90% or 95% sequence identity to a polypeptide of the present invention (SEQ ID NO:2); (b) a polypeptide encoded by a nucleic acid of the present invention; and (c) a polypeptide comprising CAR activity and modeled and designed after SEQ ID NO:1.

Another embodiment of the subject invention comprises a methods for biocatalytically reducing a carboxylic acid, or a derivative thereof, to its corresponding aldehyde product(s), to provide a method of biocatalytically reducing a carboxylic acid, or a derivative thereof, to its corresponding intermediary by-product(s), as exemplified by acyl-AMP analogs, or to provide a method of biocatalytically reducing vanillic acid, or a precursor or derivative thereof, to vanillin, all using recombinant cells, extracts, CAR protein purified therefrom or derivatives and modifications of this CAR protein.

Yet another embodiment of the invention comprises a method of making a polypeptide of a recombinant gene comprising:
 a) providing a population of these host cells; and
 b) growing the population of cells under conditions whereby the polypeptide encoded by the coding sequence of the expression cassette is expressed;
 c) isolating the resulting polypeptide.

A number of expression systems using the said host cells could be used, such as but not limited to, microbial, mammalian, plant, or insect.

BRIEF DESCRIPTION OF THE DRAWINGS

FIG. 1 is an alignment of the deduced amino acid sequence of *Nocardia* CAR with a representative sample of putative homologous molecules from other organisms. Identical amino acids are highlighted in black, and similar amino acids are highlighted in gray. The Clustal W program was used to align the above sequences, and Boxshade (0.7 setting) was used to determine the degree of residue shading. The corresponding nucleotide sequence encoding *Nocardia* CAR has been deposited in the GenBank/EMBL database.

Figure 2:
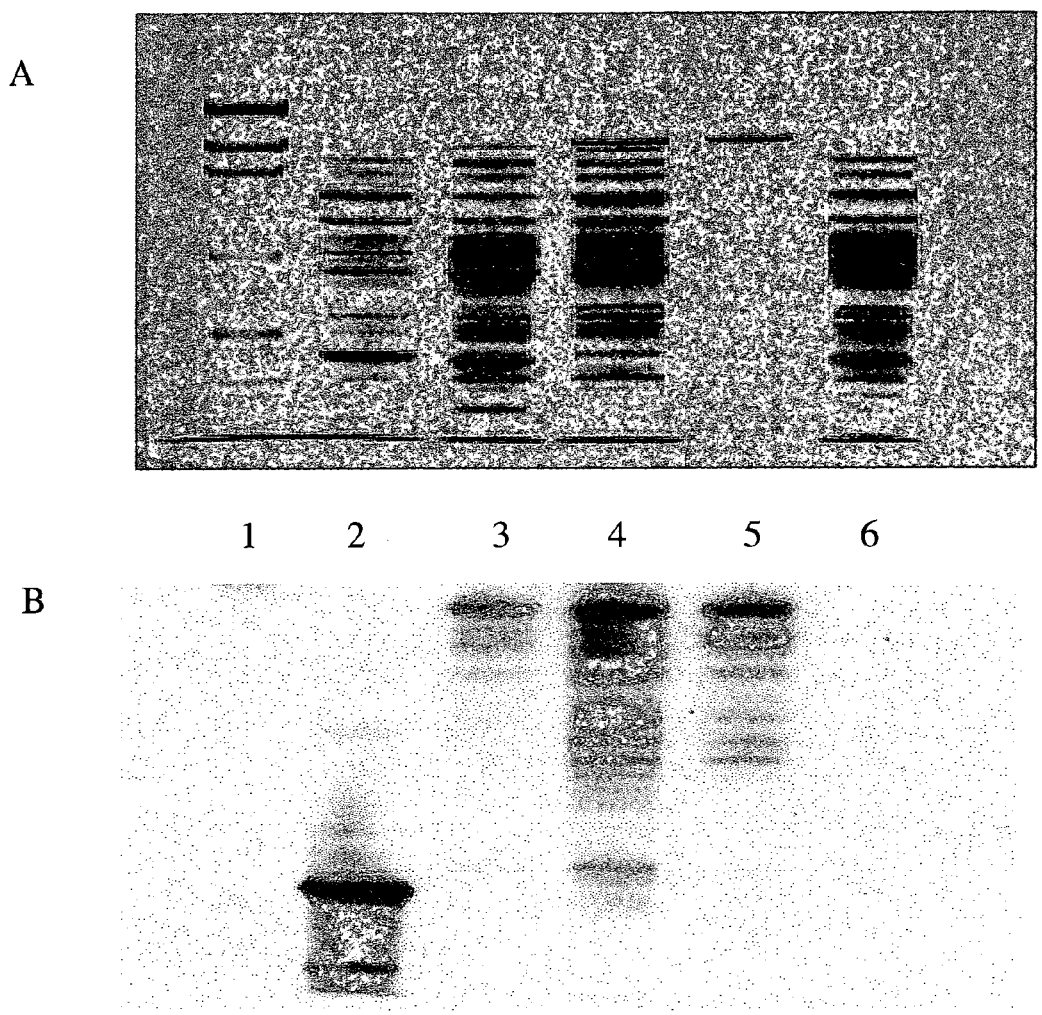

Accession nos. for the other protein sequences above are: MtfadD, *M. tuberculosis* (Z77724), Mlacl, *M. leprae* (NP_301424), Msmeg, *M. smegmatis* (Contig 3313), MBCG, *M. bovis* BCG (unnamed hypothetical protein at bases 2,885, 319–2,888,822).

FIGS. 2a and b are SDS-PAGE (a) and Western blot (b) analysis of *Nocardia* CAR expression in *E. coli* carrying pHAT10 based vectors. Samples taken from the lysates of *E. coli* cells carrying different vectors were separated in duplicate by 10% SDS-PAGE and either stained with 0.1% Coomassie blue R-250 (A) or subjected to Western blotting using a HAT-specific antibody (B). Lane assignments for panels A and B: 1, molecular weight markers: myosin (209 kDa), beta-galactosidase (124 kDa), BSA (80 kDa), ovalbumin (49.1 kDa), carbonic anhydrase (34.8 kDa), soybean trypsin inhibitor (21.5 kDa) and lysozyme (20.6 kDa), aprotinin (7.1 kDa); 2, *E. coli* cells BL21-CodonPlus® (DE3)-RP carrying pHAT-DHFR; 3, *E. coli* BL21(DE3) cells carrying pHAT-305; 4, *E. coli* BL21-CodonPlus® (DE3)-RP cells carrying pHAT-305 (uninduced); 5, purified HAT-CAR; 6, *E. coli* CodonPlus® (DE3)-RP cells carrying pHAT10.

FIG. 3 depicts the alpha-Aminoadipate reductase motifs that were described by Casqueiro at al. and Hijarrubia et al. that are present in Car. Red letters indicate identical amino acids and blue letters indicate similar amino acids. Bold letters are matches within the motif.

FIG. 4 depicts the location of motifs within Car
FIG. 5 depicts the location of motifs within FadD9.
FIG. 6 depicts the location of motifs in Aar: yeast AAR.

DETAILED DESCRIPTION OF THE PREFERRED EMBODIMENT

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); and the series *Methods in Enzymology* (S. Colowick and N. Kaplan, eds., Academic Press, Inc.).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine, one exception is *Micrococcus rubens*, for which GTG is the methionine codon (Ishizuka, et al., *J. Gen'l Microbiol,* 139:425–432 (1993)) can be modified to yield a functionally identical molecule. Accordingly, each nucleic acid disclosed herein also includes each silent variation of the nucleic acid, which encodes a polypeptide of the present invention, it is implicit in each described polypeptide sequence and incorporated herein by reference. Examples of conservatively modified variants with silent mutations are SEQ ID NO:37 (where some gca codons have been replaced with gcg condons both of which code for Alanine) and 38 (where a tca codon has been replaced with an agt codon both of which code for serine).

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 80%, or 95%, preferably 80–95% of the native protein for it's native substrate. Conservative substitution tables providing functionally similar amino acids are well known in the art. Sequence ID no 39 is a protein sequence with a conservative substitution of A for S.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company. Examples of proteins with conservatively modified variants are SEQ ID NO:_____.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate *Macronucleus,* may be used when the nucleic acid is expressed using these organisms.

When the nucleic acid is prepared or altered synthetically, advantage can be taken of known codon preferences of the intended host where the nucleic acid is to be expressed.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli,* or eukaryotic cells such as yeast, insect, plant, amphibian, or mammalian cells. Preferably, host cells are bacterial cells to provide for production of the enzyme in large quantities. A particularly preferred bacterial host cell is an *E. coli* host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "CAR nucleic acid" means a nucleic acid, including all conservatively modified variants, encoding an CAR polypeptide. The term CAR, unless otherwise stated encompasses CAR and its functional, conservatively modified variants.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual,* 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. An "inducible" or "regulatable" promoter is a promoter, which is under environmental control. Examples of environmental conditions that may effect transcription by inducible promoters include anaerobic conditions or the presence of light. Another type of promoter is a developmentally regulated or tissue specific promoter. Tissue preferred, cell type specific, developmentally regulated, and inducible promoters constitute the class of "non-constitutive" promoters. A "constitutive" promoter is a promoter, which is active under most environmental conditions.

The term "CAR polypeptide" refers to one or more amino acid sequences. The term is also inclusive of conservatively modified variants, fragments, homologs, alleles or precursors (e.g., preproproteins or proproteins) thereof. A "CAR protein" comprises a CAR polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60–90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995). Unless otherwise stated, in the present application high stringency is defined as hybridization in 4×SSC, 5× Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

"Transgenic" is used herein to include any cell, cell line, or tissue, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (Best Fit) of Smith and Waterman, Adv. Appl. Math may conduct optimal alignment of sequences for comparison. 2: 482 (1981); by the homology alignment algorithm (GAP) of Needleman and Wunsch, *J. Mol. Biol.* 48: 443 (1970); by the search for similarity method (Tfasta and Fasta) of Pearson and Lipman, *Proc.*

*Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et a., *Computer Applications in the Biosciences* 8: 155–65 (1992), and Pearson, et al., *Methods in Molecular Biology* 24: 307–331 (1994). The preferred program to use for optimal global alignment of multiple sequences is PileUp (Feng and Doolittle, *Journal of Molecular Evolution*, 25:351–360 (1987) which is similar to the method described by Higgins and Sharp, *CABIOS*, 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

GAP uses the algorithm of Needleman and Wunsch (J. Mol. Biol. 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters. Altschul et al., *Nucleic Acids Res.* 25:3389–3402 (1997).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has between 50–100% sequence identity, preferably at least 50% sequence identity, preferably at least 60% sequence identity, preferably at least 87%, more preferably at least 90%, more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55–100%, preferably at least 75%, preferably at least 80%, more preferably at least 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terms "substantial identity" in the context of a peptide indicates that a peptide comprises a sequence with between 55–100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

Carboxylic acid reductase (CAR) catalyzes the first and rate limiting step in the reduction of carboxylic acids to aldehydes, and later alcohols. According to the invention, analysis of a cloned 6.9 Kb sequence revealed that the entire open reading frame of *Nocardia* CAR and its 5' and 3' flanking regions had been cloned. ATG was identified as the translation start codon by matching the N-terminal amino acid sequence from purified *Nocardia* CAR (23) with an amino acid sequence deduced from the DNA sequence. The assignment of ATG as the start codon is supported by 5' flank region analysis: 6 bp upstream from the start codon ATG lies a conserved *Streptomyces* ribosomal binding site (GGGAGG) (27, 35). The 2.5 Kb sequence upstream of CAR showed fair homology to a putative transmembrane efflux protein (33% identity) in *S. avermitilis*, and a putative efflux protein (32% identity) in *M. tuberculosis*. The sequence downstream of *Nocardia car* showed 40%, 35%, 34% and 28% identities to putative membrane proteins in *Corynebacterium efficiens, M. tuberculosis, M. leprae*, and *S. coelicolor*, respectively. Although the CAR gene was flanked by genes encoding membrane proteins, the actual function of CAR in *Nocardia* remains unknown at this time.

BLAST analysis also showed that CAR contained two major domains and a possible phosphopantetheine attachment site. The N-terminal domain (aa 90–544) showed high homology to AMP-binding proteins. The C-terminal showed high homology to NADPH binding proteins. If a 4'-phosphopantetheine prosthetic group exists in active CAR, it likely acts as a "swinging arm" for transferring acyl-AMP intermediates to the C-terminal reductase domain. This arrangement of the CAR protein would reflect its sequential catalytic mechanism wherein the N-terminal domain catalyzes substrate activation by formation of an initial acyl-AMP intermediate, while the C-terminal portion then catalyzes the reduction of acyl-AMP by cofactor NADPH to finish a catalytic cycle. The existence of a possible 4'-phosphopantetheine prosthetic group for the catalytic process remains to be shown.

By BLAST analysis, the deduced amino acid sequence of *Nocardia* CAR showed high similarity to those of the putative enzymes in *M. tuberculosis* (fadD9, 61% identity), *M. leprae* (acyl-CoA synthetase, 57% identity), *M. smegmatis* (unnamed hypothetical protein on contig:3313, 61.8% identity), *M. bovis* strain BCG (unnamed hypothetical protein at bases 2,885,319–2,888.822, 60.3% identity), suggesting that possible functions of these proteins may relate to carboxylic acid reduction.

The present invention provides, inter alia, isolated nucleic acids of RNA, DNA, and analogs and/or chimeras thereof, comprising a CAR nucleic acid.

The present invention also includes polynucleotides optimized for expression in different organisms. For example, for expression of the polynucleotide in a maize plant, the sequence can be altered to account for specific codon preferences and to alter GC content as according to Murray et al, supra. Maize codon usage for 28 genes from maize plants is listed in Table 4 of Murray, et al., supra.

The CAR nucleic acids of the present invention comprise isolated CAR nucleic acid sequences which, are inclusive of:

(a) an isolated polynucleotide encoding a polypeptide of the present invention; (b) a polynucleotide having at least 80%, 90% or 95% identity to a polynucleotide of the present invention; (c) a polynucleotide comprising at least 25 nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (d).

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al." are used.

A. Preparation of CAR, Antibodies Specific for CAR and Nucleic Acid Molecules Encoding CAR 1. Proteins and Antibodies CAR may be prepared in a variety of ways, according to a variety of methods that have been developed for purifying CAR from bacteria which are detailed in the materials incorporated herein by reference. Alternatively, the availability of amino acid sequence information, such as (SEQ ID NO: 2), enables the isolation of nucleic acid molecules encoding CAR. This may be accomplished using anti-CAR antibodies to screen a cDNA expression library from a selected species, according to methods well known in the art. Alternatively, a series of degenerate oligonucleotide probes encoding parts or all of (SEQ ID NO: 1) FIG. 2 may be used to screen cDNA or genomic libraries, as described in greater detail below.

Once obtained, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. The pCITE in vitro translation system (Novagen) also may be utilized.

According to a preferred embodiment, larger quantities of the proteins may be produced by expression in a suitable procaryotic or eucaryotic system. This is particularly beneficial for CAR as *Nocardia* sp. are difficult to propagate and maintain in culture. For example, part or all of a CAR-encoding DNA molecule may be inserted into a vector adapted for expression in a bacterial cell (such as *E. coli*) or a yeast cell (such as *Saccharomyces cerevisiae*), or a mammalian cell. Such vectors comprise the regulatory elements necessary for expression of the DNA in the host cell, positioned in such a manner as to permit expression of the DNA in the host cell. Such regulatory elements required for expression include operably linked promoter sequences, transcription initiation sequences and, optionally, enhancer sequences.

CAR produced by gene expression in a recombinant procaryotic or eukaryotic system may be purified according to methods known in the art and incorporated herein. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or with expression/secretion systems (e.g. a C-terminal tag on a secreted protein). Such methods are commonly used by skilled practitioners.

The present invention also provides antibodies capable of binding to CAR from one or more selected species. Polyclonal or monoclonal antibodies directed toward part or all of a selected CAR may be prepared according to standard methods. Monoclonal antibodies may be prepared according to general methods of Kohler and Milstein, following standard protocols. In a preferred embodiment, antibodies are prepared, which react immunospecifically with selected epitopes of CAR distinguishing it from other enzymes.

2. Nucleic Acid Molecules

Once sequence information is obtained, nucleic acid molecules encoding CAR may be prepared by two general methods: (1) they may be synthesized from appropriate nucleotide triphosphates, or (2) they may be isolated from biological sources. Both methods utilize protocols well known in the art.

The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Nucleic acid molecules encoding CAR also may be isolated from microorganisms of interest using methods well known in the art. Nucleic acid molecules from a selected species may be isolated by screening cDNA or genomic libraries with oligonucleotides designed to match a nucleic acid sequence specific to a CAR-encoding gene. If the gene from a species is desired, the genomic library is screened. Alternatively, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al., *Molecular Cloning*, 1989, Cold Spring Harbor Press, Cold Spring Harbor N.Y.).

Alternatively, PCR (polymerase chain reaction) primers may be designed by the above method to encode a portion of CAR protein, and these primers used to amplify nucleic acids from isolated cDNA or genomic DNA. In a preferred embodiment, the oligonucleotides used to isolate CAR-encoding nucleic acids are designed to encode sequences unique to CAR, as opposed to other homologous proteins.

In accordance with the present invention, nucleic acids having the appropriate sequence homology with a CAR-encoding nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° in 1×SSC and 1% SDS, changing the solution every 30 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

CAR-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting CAR-encoding genes or mRNA in test samples, e.g. by PCR amplification.

B. Uses of CAR Protein

CAR can reduce many types of carboxylic acids. Previous work by the inventors(23, 32) showed that CAR from *Nocardia* has wide ranging substrate capabilities and that the enzyme is enantioselective versus racemic carboxylic acid substrates such as ibuprofen (7). Recombinant CAR shown in the examples herein indicate that CAR effectively reduced benzoic acid, vanillic acid and ferulic acid in preparative scale reactions. However, CAR is different than coniferyl aldehyde dehydrogenase, which uses $NAD^+$ as the cofactor to catalyze the oxidation of aldehydes to acids, which does not use ATP, and which has no homology with CAR (1). ATP-dependent CAR catalyzes the energetically unfavorable reduction of acids to aldehdyes by using ATP as an energy source to drive the reaction forward. It can also catalyze the oxidation of aldehyde to acid without ATP, but the cofactor for CAR is NADP(H) instead of NAD(H). From the gene sequence, we know that CAR (3.5 kb) is much larger than aldehyde dehydrogenases (1.5 kb) (1). The enzyme also differs from fatty acid reductases in luminescent bacteria which contains three polypeptide components (31).

1. Proteins and Antibodies

Purified CAR, or fragments thereof, may be used to produce polyclonal or monoclonal antibodies which may serve as sensitive detection reagents for the presence and accumulation of the proteins in cultured cells or tissues and in intact organisms. Recombinant techniques enable expression of fusion proteins containing part or all of a selected CAR. The full length protein or fragments of the protein may be used to advantage to generate an array of monoclonal or polyclonal antibodies specific for various epitopes of the protein, thereby providing even greater sensitivity for detection of the protein. In a preferred embodiment, fragments of CAR that distinguish CAR from serum SAAs are utilized for generating epitope-specific antibodies.

Polyclonal or monoclonal antibodies immunologically specific for CAR may be used in a variety of assays designed to detect and quantitative the proteins. Such assays include, but are not limited to, (1) immunoprecipitation followed by protein quantification; (2) immunoblot analysis (e.g., dot blot, Western blot) (3) radioimmune assays, (4) nephelometry, turbidometric or immunochromatographic (lateral flow) assays, and (5) enzyme-coupled assays, including ELISA and a variety of qualitative rapid tests (e.g., dip-stick and similar tests).

Polyclonal or monoclonal antibodies that immunospecifically interact with CAR can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

2. Nucleic Acids

CAR-encoding nucleic acids may be used for a variety of purposes in accordance with the present invention. The DNA, RNA, or fragments thereof may be used as probes to detect the presence of and/or expression of the genes. Methods in which CAR-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR) and reverse transcriptase-PCR (RT-PCR).

The exemplified CAR-encoding nucleic acids of the invention (e.g., cow, sheep, horse) may also be utilized as probes to identify related genes from other species, including s. As is well known in the art and described above, hybridization stringencies may be adjusted to allow hybridization of nucleic acid probes with complementary sequences of varying degrees of homology.

In addition to the aforementioned uses of CAR-encoding nucleic acids, they are expected to be of utility in the creation of transgenic cells, tissues and organisms.

The present invention provides novel purified and isolated nucleic acid sequences encoding CAR protein. In presently preferred forms, the DNA sequences comprise cDNA sequences encoding the novel CAR, or its conservatively modified variants, which are expressed in *Nocardia* cells. In a more preferred embodiment the nucleic acid sequence comprises at least about 80% identity to (SEQ ID NO: 1) or 80% identity of the encoded amino acid sequence. Specifically, the sequence isolated is depicted in (SEQ ID NO: 1). Alternate DNA forms such as genomic DNA, and DNA prepared by partial or total chemical synthesis from nucleotides as well as DNA with deletions or mutations, is also within the contemplated scope of the invention.

Association of DNA sequences provided by the invention with homologous or heterologous species expression control DNA sequences such as promoters, operators, regulators, and the like, allows in vivo and in vitro transcription to make mRNA which, in turn, is susceptible to translation to provide the proteins of the invention, and related poly- and oligo-peptides in large quantities. In a presently preferred DNA expression system of the invention CAR encoding DNA is operatively linked to a regulatory promoter DNA sequence allowing for in vitro transcription and translation of the protein.

Incorporation of DNA sequences into prokaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources.

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both prokaryotic and eucaryotic systems may be used to express CAR encoding sequences; prokaryotic hosts are, of course, the most convenient for cloning procedures. Prokaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, Gene (1977) 2:95. pBR322 contains genes for ampicillin and tetracycline resistance, and thus provides multiple selectable markers which can be either retained or destroyed in constructing the desired vector. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2μ origin of replication of Broach, J. R., *Meth Enz* (1983) 101:307, or other yeast compatible origins of replication (see, for example, Stinchcomb, et al, *Nature* (1979) 282:39, Tschumper, G., et al, *Gene* (1980) 10:157 and Clarke, L, et al, *Meth Enx* (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMT1I (Karin, M., et al, *Nature* (1982) 299:797–802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci (USA)* 1972) 69:2110, or the rbC12 method described in Maniatis, et al, *Molecular Cloning: A Laboratory Manual* (1982) Cold Spring Harbor Press, p. 254 and Hanahan, D., *J Mol Biol* (1983) 166: 557–580 may be used for prokaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777–785 may be used. Transformations into yeast may be carried out according to the method of Beggs, J. D. *Nature* (1978) 275:104–109 or of Hinnen, A., et al, *Proc Natl Acad Sci (USA)* (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and relegated in the form desired.

The DNA sequences which form the vectors are available from a number of sources. Backbone vectors and control systems are generally found on available "host" vectors which are used for the bulk of the sequences in construction. Typical sequences have been set forth above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire sequence for genes or cDNA's of sizable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, *Nature* (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.75y pmoles γ32P-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl2, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 µl volumes under the following standard conditions and temperatures: for example, 20 mM Tris-Cl pH 7.5, 10 mM MgCl$_2$, 10 mM DTT, 33 µg/ml BSA, 10 mM–50 mM NaCl, and either 40 µM ATP, 0.01–0.02 (Weiss) units T4 DNA ligase at 0 C (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per µg of vector at 60° for about one hour. In order to recover the nucleic acid fragments, the preparation is extracted with phenol/chloroform and ethanol precipitated. Alternatively, re-ligation can be prevented in vectors which have been double digested by additional restriction enzyme digestion and/or separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al, *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

Correct ligations for plasmid construction can be confirmed by first transforming *E. coli* strain MC1061 obtained from Dr. M. Casadaban (Casadaban, M., et al, *J Mol Biol* (1980) 138:179–207) or other suitable host with the ligation mixture. Successful transformants are selected by ampicillin, tetracycline or other antibiotic resistance by using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem Acids Res* (1979) 7:1513–1523. The isolated DNA is analyzed by restriction and/or sequenced by the dideoxy nucleotide method of Sanger, F., et al, *Proc Natl Acad Sci* (USA) (1977) 74:5463 as further described by Messing, et al, *Nucleic Acids Res* (1981) 9:309, o4 by the method of Maxam, et al, *Methods in Enzymology* (1980) 65:499.

Hosts Exemplified

Host strains used in cloning and prokaryotic expression herein are as follows:

For cloning and sequencing, and for expression of construction under control of most bacterial promoters, *E. coli* strains such as MC1061, DH1, RR1, C600hfl, K803, HB101, JA221, and JM101 can be used.

It can therefore be seen that the above invention accomplishes at least all of its stated objectives. All references cited herein are hereby expressly incorporated herein in their entirety by reference.

EXAMPLES

Materials and enzymes. Restriction enzymes, T4 DNA ligase and shrimp alkaline phosphatase were purchased from New England Biolabs (Beverly, Mass.); PGEM-T easy vector kit from Promega (Madison, Wis.); *Escherichia coli* BL21(DE3) and BL21-CodonPlus® (DE3)-RP competent cells from Stratagene (La Jolla, Calif.); Polyclonal rabbit anti-HAT antibody, pHAT10 vector and Talon® resin from Clontech (Palo Alto, Calif.); goat anti-rabbit IgG-conjugated alkaline phosphatase and Immun-Star Chemiluminescent Substrate Kit from Bio-Rad (Hercules, Calif.); Qiaprep Spin Miniprep kit and Qiaquick kit from Qiagen Inc. (Chatsworth, Calif.). All other chemicals were from Sigma (St Louis, Mo.) unless specified.

Bacterial strains, plasmids, media and growth conditions. The bacteria and plasmids used in this study are given in Table 1. *Nocardia* sp. NRRL 5646 (9), maintained in the University of Iowa College of Pharmacy culture collection on slants of Sabouraud-Dextrose agar or sporulation agar (ATCC no. 5 medium), was grown in Luria-Bertani (LB) medium containing 0.05% Tween 80 (vol/vol, liquid medium only). With *E. coli* (JM109, BL21 (DE3), or BL21-CodonPlus® (DE3)-RP) as the recombinant host for pHAT based vectors, cells were grown at 37° C. on solid or in liquid LB medium. Ampicillin (100 µg/ml) was incorporated into LB medium to select for recombinants. In addition, isopropyl-β-D-thiogalactopyranoside (IPTG, 1 mM) and/or 5-bromo-4-chloro-3-indolyl-β-D-galactopyranoside (X-Gal, 80 µg/ml) were included for recombinant selection and identification.

Molecular biology techniques. All DNA manipulations used for this study were performed by standard protocols (33). *Nocardia* sp. NRRL 5646 chromosomal DNA (gDNA) was purified as described by Pelicic et al. (29) with modifications. Briefly, ampicillin (0.2 mg/ml) and glycine (1.5%, vol/vol) were added into 100 ml stationary phase cultures, two hrs before harvest by centrifugation at 4,000×g for 15 min and 4° C. Cells (1.5 g, wet weight) were resuspended in 5 ml of lysis solution I (25% sucrose in 50 mM Tris-HCl, pH 8.0 containing 50 mM EDTA and 12 mg/ml lysozyme), and incubated at 37° C. with shaking at 50 rpm for 1.5 hrs. Lysis solution II (3 ml of 100 mM Tris-HCl, pH 8.0 containing 1% SDS and 700 □g/ml proteinase K) was then added, and the sample was incubated at 55° C. for 4 hrs. Then 45 □l Rnase (500 □g/ml) was added into the lysate, and incubated with shaking at 50 rpm and 37° C. for 1 h. The lysate was then extracted with phenol-chloroform-isoamyl alcohol (25:24:1, vol/vol/vol, Invitrogen Life Technologies), and gDNA was concentrated by ethanol precipitation, yielding a total of 90 µg gDNA.

Recombinant plasmids from *E. coli* were purified by using a Qiaprep spin miniprep kit, and Qiaquick kits were used for PCR cleanup and gel extractions with vector constructs as instructed by the manufacturer. All PCR cloning amplification was done with either Platinum Taq DNA polymerase or Platinum Pfx DNA polymerase (Invitrogen). Restriction enzymes and DNA-modification enzymes were used according to the manufacturer's protocols. Sequencing was conducted using an Applied Biosystem 373A DNA sequencer.

PCR and cloning of PCR product. In order to obtain a portion of *Nocardia car*, oligonucleotides were constructed corresponding to N-terminal and internal amino acid sequences, which were determined with purified CARBOXYLIC ACID REDUCTASE (23). Forward primers (Noc-1 and Noc-2) were based on the N-terminal amino acid sequence AVDSPDERLQRRIAQL (SEQ ID NO:6), and reverse primers (Noc-3 and Noc-4) were based on the complementary strand sequence encoding the internal amino acid sequence KLSQGEFVTVAHLEAV (SEQ ID NO:7) (Table 2). Degeneracy of all four primers was minimized by taking advantage of the reported *Nocardia* codon preferences (10). A typical 50 µl reaction in 1×PCR buffer contained 500 ng *Nocardia* DNA, 5 mM$^{++}$, 500 µM of each dNTP, 0.5 µM of each primer, 1% DM50 (vol/vol) and 3.5 units of Taq DNA polymerase. The reaction mixtures were subjected to the following cycles: one cycle at 94° C. for 4 mm, thirty cycles at 94°for 45 s, 56°for 45 s, and 72° C. for 2 mm, and finally one cycle at 72° C. for 10 mm. PCR products were separated on 1% agarose gel. The desired band was excised and extracted with a Qiagen gel extraction kit. The resulting PCR product was ligated into pGEM-T by T4 ligase. The ligation mixture was mixed with *E. coli* JM109 cells and chilled on ice for 30 nun. Cells were transformed by heat shock, then placed immediately on ice. Transformed *E. coli* JM 109 cells were mixed with 800 µl SOC medium and incubated at 37° C. for 1.5 hrs on a rotary shaker at 170 rpm. Plasmid transformants were spreadplated onto LB/X-Gal agar supplemented with 100 µg/ml ampicillin. Ampicillin resistant colonies were picked and used to inoculate 5 ml LB broth supplemented with 100 µg/ml ampicillin and incubated overnight at 37° C. on a rotary shaker operating at 170 rpm. Cultures were harvested by centrifugation and subjected to a plasmid miniprep procedure (Qiagen). The resulting recombinant plasmid was sequenced in both directions with sequencing primers (Table 2).

Inverse PCR. Inverse PCR was used to obtain the entire *Nocardia asteriodes car* gene sequence. To prepare the template for Inverse PCR analysis, 1 µg of *Nocardia asteriodes* gDNA was completely digested with 20 U SalI or Acc65I at 37° C. Digested gDNA was diluted five fold and then circularized with T4 DNA ligase. PCR primers CA-5 (Forward) and CA-7 (Reverse) were designed based on part of the *Nocardia asteriodes car* sequence obtained above. Inverse PCR was performed using Taq DNA polymerase for a total of 30 cycles with the following cycling pattern: melting at 94° C. for 45 s, annealing at 57° C. for 45 s, and polymerization at 72° C. for 2 min. The amplified PCR product was cloned in PGEM-T, and transformed into *E. coli* JM109 cells by heat shock treatment as described above. Plasmid preparations from independent clones were sequenced in both directions. The resulting sequence combined with the above part of *Nocardia asteriodes car* gave a 4.6 Kb sequence which contained the entire *Nocardia asteriodes car* gene (with Acc65I digested and then religated gDNA as the template). A sequence of 2.5 Kb upstream car was obtained with SalI digested and religated gDNA as the template for PCR.

Construction of expression vectors. To express recombinant *Nocardia asteriodes car* in *E. coli*, a DNA fragment containing *Nocardia asteriodes car* was generated by PCR using the primers car-F and car-R with *Nocardia asteriodes* gDNA as the template. For cloning purposes, those two primers incorporated a BamHI site at the 5' end and an KpnI site at the 3' end of the *Nocardia* gene insert. PCR was performed using Platinum Pfx DNA polymerase for a total of 30 cycles with the following cycling pattern: melting at 94° C. for 18 s, annealing at 59° C. for 30 s, and polymerization at 72° C. for 4 min. PCR products were sequentially digested with BamHI and KpnI was separated on a 1% agarose gel and purified using a Qiagen gel extraction kit, and then subcloned into the corresponding sites of pHAT10 to result in pHAT-305. One round of sequencing confirmed that *Nocardia car* had been correctly cloned into the pHAT vector by using sequence primers.

Expression of *Nocardia car* in *E. coli*. A 100 ml culture of *E coli* cells (BL21(DE3) or BL21-CodonPlus® (DE3)-RP) harboring pHAT-305 were grown overnight in LB medium containing 100 □g/ml ampicillin at 37° C. Overnight broth cultures were diluted 20 fold in fresh LB medium containing 100 µg/mL ampicillin, and then incubated at 170 rpm in a rotary shaker at 37° C. to an optical density at 600 nm of 0.6, followed by addition of 1 mM IPTG and further incubation for 4.5 h. The cells were harvested by centrifugation (10 min, 5,000×g), and then stored at −65° C. before use.

Enzyme assay. The standard reaction mixture contained 1 mM ATP, 0.15 mM NADPH, 5 mM sodium benzoate, 10 mM MgCl$_2$ and enzyme in 0.05 M Tris buffer (pH 7.5) containing 1 mM EDTA, 1 mM DTT and 10% glycerol (vol/vol), in a final volume of 1.4 ml. The reference cuvette contained all components except benzoate. Reactions were initiated by adding enzyme, and were monitored by recording the absorption decrease at 340 nm at 25° C. with a Shimadzu UV-2010PC scanning spectrophotometer. One unit of the enzyme was defined as the amount of enzyme that catalyzed the reduction of 1 □mol of benzoate to benzaldehyde.min$^{-1}$ under standard assay condition. Protein concentrations were measured by the Bradford protein microassay (4) with bovine serum albumin as the standard.

Purification of overexpressed HAT-CAR fusion protein. *E. coli* BL21-CodonPlus® (DE3)-RP cells (4.3 g wet weight) transformed with pHAT-305 were suspended in 26 ml of 0.05 M $K_2HPO_4$ (pH 7.5) buffer containing 0.3 M NaCl, 10% (vol/vol) glycerol, 0.2 mM PMSF and 3 mM β-mercaptoethanol. The cells were disrupted by passing through a French Press cell at 12,000 psi twice. The cell debris was removed by centrifugation for 60 min at 25,000×g and 4° C. The resulting supernatant (27 ml) was referred to as cell-free extract (CFE) and used for HAT-CAR purification. 24 ml of CFE was loaded on a 6 ml bed volume column of Talon resin (A cobalt complexed resin made by Clontech that specifically binds the HAT tag.) equilibrated with 0.05 M $K_2HPO_4$ buffer pH 7.5 containing 0.3 M NaCl, 10% (vol/vol) glycerol, at a flow rate of 0.4 ml/min. After the column was washed with 35 ml 0.05 M $K_2HPO_4$ buffer pH 7.5 containing 0.3 M NaCl, 10% (vol/vol) glycerol, the HAT-CAR was eluted sequentially by 16 ml of 5 mM, 7.5 mM, 10 mM, and 20 mM of Imidazole in 0.05 M $K_2HPO_4$ buffer pH 7.5 containing 0.3 M NaCl, 10% (vol/vol) glycerol. Active fractions were pooled and then concentrated by ultrafiltration in an Amicon concentrator (PM-10 membrane) and then diluted with 100 ml of 50 mM Tris buffer (pH 7.5) containing 1 mM EDTA, 1 mM DTT, and 10% glycerol. The resulting enzyme preparation was loaded on a DEAE Sepharose column (1.5 by 20 cm with a bed volume of 24 ml) equilibrated with 50 mM Tris buffer (pH 7.5) containing 1 mM EDTA, 1 mM DTT, and 10% glycerol. The column was washed with 30 ml of starting buffer and eluted with a 0 to 0.5 M NaCl linear gradient (total 100 ml). The active fractions (29 to 34) were combined for subsequent analysis (Table 3).

SDS-PAGE and Western blot analysis. Proteins were separated by SDS-PAGE as described by Laemmli (22). For Western blot analysis, protein samples were subjected to SDS-PAGE and then transferred to a polyvinylidene difluoride (PVDF) membrane. To identify proteins containing the HAT tag, the PVDF membrane was first incubated with 2% fat-free milk in TBS, then with a polyclonal anti-HAT antibody (diluted 1:20,000) that recognizes epitopes throughout the HAT tag, and finally with a polyclonal goat anit-rabbit IgG conjugated to alkaline phosphatase (diluted 1:20,000), which was used with the Bio-Rad Immuno-Star Chemoluminescent Substrate. Proteins containing the HAT tag were identified with Kodak BioMax MR photographic film after 2 min exposures. *E. coli* JM 109 carrying an expression vector coding for HAT-tagged dihydrofolate reductase (DHFR, Clontech) was used as a positive control for each Western blot analysis, and *E. coli* BL21-Codon-Plus® (DE3)-RP carrying the pHAT10 vector was used as a negative control.

In vitro and in vivo transformations of benzoate, vanillic acid, and ferulic acid. In vitro enzyme reactions were carried out in a reaction mixture of 50 ml of 50 mM Tris-HCl buffer (pH 7.5) containing 0.1 mmol of substrate, 12.5 mg of NADPH, 55 mg ATP, 101 mg $MgCl_2$, 33.6 mg glucose-6-phosphate, and 3 U of glucose-6-phosphate dehydrogenase, and 1 mg purified HAT-CAR (0.1 U). Reaction mixtures were incubated at 30° C. with gentle shaking at 50 rpm for 24 h.

In vivo whole cell reactions were typically conducted with 100 ml cultures of *E. coli* BL21-CodonPlus® (DE3)-RP carrying pHAT-305. Cultures were induced by 1 mM IPTG for 4 hrs before receiving 1 mg/ml of benzoic acid, vanillic acid, or ferulic acid.

Samples of approximately 2 mL were removed at various time intervals, sample pH was adjusted to pH 2.0 with 6N HCl, and samples were extracted with 1 ml ethyl acetate, and centrifuged for 2 min at 1,000×g. Organic phases were removed and used to spot silica gel $GF_{254}$ TLC plates for analysis, and comparison with authentic standards of benzaldehyde, vanillin and coniferaldehyde. For metabolite isolation, reactions were stopped by adjustment of mixtures to pH 2.0 with 6N HCl, and extracted three times with half-volumes of ethyl acetate. After removal of solvent by rotary evaporation, reduction products were purified by preparative TLC for analysis and comparison with authentic standards.

Four degenerate primers (two forward, CA-1 and CA-2; and two reverse, CA-3 and CA-4) incorporating *Nocardia* codon preferences (10) were initially designed to identify part of *Nocardia car*, based on the known N-terminal amino acid sequence and internal amino acid sequences (Li and Rosazza, 1997). PCR products were cloned into a pGEM-T vector and sequenced to give a 1.6 Kb sequence.

Gene sequence specific primers (CA-5 and CA-6) based on this identified fragment were synthesized for inverse PCR to clone the entire *Nocardia car* gene. The sequence derived from two inverse PCR experiments and the above-obtained sequence gave a total of 6.9 Kb of data, which included the entire *Nocardia car* gene and its flanking regions. The DNA sequence and the deduced amino acid sequence of *Nocardia car* will be deposited in the GenBank upon filing of a patent. *Nocardia car* consisted of 3525 bp, corresponding to 1174 amino acid residues with a calculated molecular mass of 128.3 kDa and an isoelectric point (pI) of 4.74. The N-terminal amino acid sequence of purified *Nocardia* CAR exactly matched the deduced amino acid sequence of the N-terminus, with Ala as the first amino acid. Met, encoded by the start codon ATG in *Nocardia car*, is apparently removed by posttranslational modification in the mature form of the protein produced in wild type *Nocardia* cells.

Comparative sequence analysis. When the *Nocardia car* sequence was compared by BLAST analysis with DNA sequences in the NCBI database, the BestFit analysis of two nucleotide sequences showed that the *Nocardia* CAR was 60% and 57% identical to the putative polyketide synthetase fadD9 of *M. tuberculosis* and putative acyl-CoA synthetase of *M. leprae* respectively. Putative proteins in *M. smegmatis* and *M. bovis* strain BCG were 61.8% and 60.3% identical to *Nocardia* CAR. The Clustal W program (35) was used to align CAR with these closely-related putative proteins from different species (FIG. 1).

Heterologous expression of *Nocardia car*. For expression of *Nocardia* CAR, the *Nocardia car* gene was successfully cloned in frame into pHAT10 to form the expression vector pHAT-305. Constructed vectors were found by complete sequencing to have a car that was 100% identical to the original *Nocardia car* sequence, proving that no errors were introduced by Pfx DNA polymerase cloning. Lysate from *E. coli* BL21(DE3) cells carrying pHAT-305 had moderate carboxylic acid reductase activity (0.003 U/mg of protein) versus that of *Nocardia* wild type cells (0.03 U/mg of protein) (23). However, the expression of pHAT-305 was much improved when it was transformed into *E. coli* Codon-Plus® (DE3)-RP cells, where a crude extract specific activity of 0.009 U/mg of protein was observed. When these cultures were examined by SDS-PAGE, the Coomassie blue-stained band with an apparent molecular size of 132.4 kDa were confirmed to be the HAT-CAR by activity assay and Western blot analysis (FIG. 2). Also, the DHFR-positive control (lysate of *E. coli* carrying the DHFR gene cloned into the same pHAT 10 vector) and negative control (lysate of *E. coli* BL21-CodonPlus® (DE3)-RP cells carrying the pHAT10 vector) showed the absence of a 132.4 kDa band by SDS-PAGE and Western blot analyses.

The HAT-CAR protein from *E. coli* was purified to homogeneity on SDS-PAGE by Talon® resin affinity chromatography and DEAE sepharose column with a overall recovery of 85%. Western blot analysis showed that there were some HAT-tag positive smear bands with lower molecular weight than that of HAT-CAR. The purified HAT-CAR showed a specific CAR activity of 0.11 $\mu$mol·min$^{-1}$·mg$^{-1}$ protein, which was less than that of CAR purified from *Nocardia* cells (5.89 U/mg of protein) (23). Kinetic constants were determined by fitting experimental data with Cleland's kinetics program (9). Km values for benzoate, ATP and NADPH were determined to be 852±82 mM, 69±6.6 $\mu$M, and 57±3.6 $\mu$M, respectively. These are similar to the Km values of the natural protein. Vmax was determined to be 0.135±0.004 $\mu$mol·min$^{-21}$·mg$^{-1}$ protein, which is lower than that of the natural protein at 0.902±0.04 $\mu$mol·min$^{-1}$.mg$^{-1}$ protein (23).

In vitro transformations showed that pure HAT-CAR could reduce various carboxylic acids to their corresponding aldehydes in reactions that were not optimized. Benzoic acid was converted to benzaldehyde (96% yield), vanillic acid to vanillin (49% yield), and ferulic acid to coniferyl aldehyde (22% yield). In vivo studies on the transformation of the same substrates showed that benzoate was quickly converted to benzyl alcohol, while vanillin and coniferyl aldehyde converted to their corresponding alcohols.

Recombinant CAR bound weakly to Talon® affinity matrix, being eluted from columns by 10 mM imidazole, rather than the 100 mM imidazole usually required for HAT-tagged proteins elution. HAT-CAR can be easily purified to near homogeneity (SDS-PAGE) with Talon® matrix chromatography. Minor impurities in enzyme preparations after the affinity step were not completely removed by DEAE sepharose column chromatography. Although trace impurities were not detected by SDS-PAGE, they were detected by Western blot analysis (FIG. 2).

These trace impurities were HAT-tag containing proteins that are likely hydrolyzed fragments of HAT-CAR cleaved by metal proteases. Metal protease inhibitors were not used to prevent protease cleavage during cell disruption because they would be incompatible with Talon® matrix chromatography.

CAR was only moderately expressed in *E. coli* BL21 (DE3) cells carrying pHAT-305. It was thought that low expression was mainly due to the codon bias that can cause early termination and misincorporation of amino acids since the G+C content of the sequence is 66%. In searching for new hosts to overcome the codon bias, the expression of pHAT-305 was much improved when it was carried out in *E. coli* CodonPlus® (DE3)-RP cells. The protein bands were clearly seen on the SDS-PAGE (FIG. 2) with the CFE enzyme preparation. Although CAR of the correct molecular mass accumulates in cells, the specific activity of the crude extract was only improved about 3 fold. The specific activity of CAR in *E. coli* BL21 (DE3) may be higher than in *E. coli* CodonPlus® (DE3)-RP cells. We have shown that approximately 50 mg pure HAT-CAR can be obtained from a 1 liter culture of *E. coli* CodonPlus® (DE3)-RP cells.

Comparing relative protein expression and differing specific activities of CARBOXYLIC ACID REDUCTASE in these two different hosts, we speculate that two forms of the enzyme may exist in *E. coli* cells: one active, while the other is an inactive variant. It is possible that the conversion of an inactive form of the enzyme (pre-CARBOXYLIC ACID REDUCTASE) to the catalytically active form of the enzyme (CARBOXYLIC ACID REDUCTASE) may occur by posttranslational modification. One such modification that has precedence in the type of reaction catalyzed by carboxylic acid reductase would be phosphopantetheinylation (12). In this type of model, inactive pre-carboxylic acid reductase would be converted to active carboxylic acid reductase by attachment of phosphopantetheine prosthetic group possibly attached to Ser688 to function as a Swinging arm. In the active enzyme, carboxylic acid reductase, the SH of the phosphopantetheine prosthetic group would react with acyl-AMP to form an acyl-S-pantotheine-carboxylic acid reductase intermediate. The C-terminal reductase domain finishes the catalytic cycle by delivering hydride from NADPH to the acyl-S-pantoheine carboxylic acid reductase intermediate freeing an aldehyde product. α-Aminoadipate reductase is well studied, and motifs responsible for adenylation of α-aminoadipate, reduction, NADPH binding and attachment of a phosphopantetheinyl group used in the reaction have been identified (5, 18). While traditional blast analysis does not reveal the expected common motifs in the N-terminal portion of car, they do appear in the C-terminal portion. A P-pantotheine attachment site, domain J, is clearly present in carboxylic acid reductase (LGGxSxxA) (SEQ ID NO:8), as are the reduction domain (GYxxSKW) (SEQ ID NO:9) and the NADP binding domain (GxxGxLG) (SEQ ID NO: 10). These motifs are fully conserved in the *Mycobactrium* carboxylic acid reductase homologs (FIG. 1). Whether benzoate induction (23) increases the expression of carboxylic acid reductase, or catalyzes the conversion of inactive form enzyme to active form by a posttranslational modification remains to be established.

Biotransformation reactions using IPTG-induced whole growing cells of *E. coli* CodonPlus® (DE3)-RP cells carrying pHAT-305 were simple to conduct, and they smoothly converted carboxylic acids to aldehydes—and subsequently to alcohols. With whole cells, expensive cofactors are not needed (25), and the relatively slow reduction of aldehyde products formed by CAR to alcohols by an endogenous *E. coli* alcohol dehydrogenase similar to that in *Nocardia* (25) may be obviated by judicious biochemical engineering approaches with the recombinant organism.

The unique car sequence car for the carboxylic acid reductase enzyme, CAR, may be used to produce recombinant cultures such as *E. coli* for direct use in whole cell biocatalytic conversions of an enormous number of synthetic or natural carboxylic acids (23, 32) including aromatic, aliphatic, alicyclic and others. Alternatively, this gene sequence, or homologs of this gene sequence may be incorporated into the genomes of multiply recombinant strains through pathway engineering to be used as a part of a biosynthetic or biodegradative pathway leading to useful compounds.

TABLE 1

Strains and plasmids used in this study

| Strains or plasmids | Relevant properties | Reference or source |
|---|---|---|
| *Nocardia* sp. NRRL 5646 | Wild type | 8 |
| *E. coli* JM 109 | RecA, recombinant vector host strain | Promega |
| *E. coil* BL21 (DE3) | Inducible T7 RNA polymerase, Amp$^r$ | Stratagene |
| *E. coil* BL21-CodonPlus ® (DE3)-RP | having argU and proL tRNA genes | Stratagene |

TABLE 1-continued

Strains and plasmids used in this study

| Strains or plasmids | Relevant properties | Reference or source |
|---|---|---|
| pGEM-T easy | T/A PCR cloning vector, Amp$^r$ | Promega |
| pHAT10 | Cloning vector for addition of HAT-tag to the N-terminus, Amp$^r$ | Clontech |
| pHAT-305 | pHAT-10 with car insert | This study |
| pHAT-DHFR | Positive control expression vector with dihydrofolate reductase gene tagged with HAT at the N-terminus | Clontech |

TABLE 2

Oligonucleotides used in this study

| | | |
|---|---|---|
| GTSGATTCACCSGATGAG | This study | 11 |
| CCSGATGARCGSCTACAG | This Study | 12 |
| TGSGCSACSGTSACGAAC | This Study | 13 |
| SACGAAYTCSCCCTGSGAC | This Study | 14 |
| GGTCGGGATCAATCTCAACTACATG | This Study | 15 |
| CTTCAGCTGCTCTGACGGATATCAG | This Study | 16 |
| CCTGCTCATCTTCTGCAAACAACTG | This Study | 17 |
| CGC<u>GGATCC</u>GCAGTGGATTCACCGG ATGAGC | This Study | 18 |
| CGG<u>GGTACC</u>CTGATATCCGTCAGA GCAGCTG | This Study | 19 |
| Sequencing primers | | |
| TAATACGACTCACTATAGGG | Sigma-Genosys | 20 |
| CATACGATTTAGGTGACACTATAG | Sigma-Genosys | 21 |
| CAGGAAACAGCTATGACC | Sigma-Genosys | 22 |
| CTCGACCTGGCCGATATCCAC | This Study | 23 |
| GAGGACGGCTTCTACAAGAC | This Study | 24 |
| GACGCGCACTTCACCGACCTG | This Study | 25 |
| GTCGACCTGATCGTCCATCC | This Study | 26 |
| ACCTACGACGTGCTCAATC | This Study | 27 |
| CGTACGACGATGGCATCTC | This Study | 28 |
| GTGGATATCGGCCAGGTCGAG | This Study | 29 |
| GGTGGCAGGATGGAATCGG | This Study | 30 |
| CGTCGATTCGCGATTCCCTG | This Study | 31 |

$^a$Restriction cleavage sites are underlined; R = A or G, Y = C or T, S = G or C.

TABLE 3

Purification of recombinant HAT-CAR from Nocardia.

| Step Purification | Total protein (mg) | Total activity (U)$^1$ | Specific activity (U/mg) | Yield (%) | |
|---|---|---|---|---|---|
| Crude extract | 600 | 5.21 | 0.009 | 100 | 1 |
| Talon Matrix | 69.1 | 4.57 | 0.066 | 87.7 | 7.62 |
| DEAE Sepharose | 49 | 4.43 | 0.09 | 85 | 10 |

$^1$One unit of the enzyme is defined as the amount of the enzyme that catalyzed the reduction of 1 μmol of benzoate to benzaldehyde per min at 25° C.

Homology

In conducting BLAST analysis the database proteins most similar to CAR are proteins of unknown function in mycobacteria. The most similar known enzymes are Alpha aminoadipate reducatase and peptide synthetases, but it is unlikely that Car is either of these. Nonetheless, it is likely that the mechanism of benzoate reduction is similar to alpha-aminoadipate reduction. Piperideine-6-carboxylate dehydrogenase has no sequence similarity to CAR, and its mechanism is unlikely to be related to that of Car.

CAR shows very unique catalytic properties. It is very tolerant, taking carboxylic acids with different structures, as long as they are hydrophobic. In addition, when CAR was tested with alpha amino acids, none of them were reduced. If the alpha amino group is protected with a hydrophobic group, such as Boc, all were reduced with good efficiencies. Therefore, CAR is most likely different from alpha-amino adipate reductase despite the similar motifs.

CAR is most homologous to a set of proteins of similar large size, thus far found only among the mycobacteria. The best hit is with the Mycobacterium tuberculosis protein identified as a 'putative substrate-CoA ligase' (in Mtb CDC1551) or 'putative acyl CoA ligase' (FadD9; Rv2590, in Mtb H37Rv). These proteins give a score of 1336, E value of 0, and are 60% identical and 75% positive. The next best hit is with a 'putative acyl-CoA synthetase' from Mycobacterium leprae. Another strong hit is also obtained with the Mycobacterium smegmatis database.

A conserved domain search shows that the protein consists of two main domains, plus a small third domain. The N-terminal portion has homology with a variety of acyl-CoA synthetases and AMP-binding proteins, polyketide synthase, and peptide synthetase modules. Between the N-terminal and C-terminal regions is a short section similar to phosphopantetheine attachment sites (aa 650–725). The C-terminal portion has homology with a variety of dehydrogenases and NAD(P)-dependent enzymes. The 740 N-terminal amino acids and the 482 C-terminal amino acids were blasted giving a bit of overlap. Tables 1 and 2 describe most of the best blast hits. Most protein homologues listed do not have known functions. It appears that the N-terminal and C-terminal Blast hits of CAR with Streptomyces are not with the same proteins, but this is not yet clear, since the S. coelicolor database is not yet fully annotated. The closest hits to known proteins are with alpha-aminoadipate reductase and a non-ribosomal peptide synthetase (for both N-terminal and C-terminal portions). These hits with known proteins are not very strong.

alpha-Aminoadipate semialdehyde is in chemical equilibrium with 1-piperideine-6-carboxylate. It is of interest that there is some similarity in structure between the 1-piperideine-6-carboxylate and benzoic acid. This might suggest some evolutionary relationship between the benzoate reductase and the aminoadipate enzyme. However, given the low level of identity, it is unlikely that the benzoate reductase is actually an alpha-aminoadipate semialdehyde dehydrogenase. Furthermore, the *Mycobacterium* homologues would not be Aar because these organisms make lysine via the diaminopimelic acid path rather than the aminoadipate path.

Bacterial means for converting piperideine-6-carboxylate (a-aminoadipate semialdehyde) into a-aminoadipate exists in *Nocardia, Streptomyces, Flavobacterium* and *Pseudomonas,* by use of 1-piperideine-6-carboxylate dehydrogenase.

The gene for this enzyme has been identified in *Flavobacterium* and *Streptomyces clavuligerus,* and it has good homology with AldB (Rv3293 in *M. tuberculosis*). However, it has no homology with Car, despite the similarity of the piperideine-6-carboxylate dehydrogenase with the Car reaction. This makes sense, since this reaction does not involve ATP and NAD is used instead of NADP.

Alpha-Aminoadipate reductase has been well studied. Motifs responsible for adenylation of alpha-aminoadipate, reduction, NADP(H) binding, and attachment of the P-pantetheinyl group used in the reaction have been identified. Given the similar overall sizes of Aar proteins and Car, and at least weak blast hits with both the N-terminal and C-terminal portions of the Car sequence, it might be reasonable to postulate a great similarity in mechanism between the two enzymes. However, traditional blast analysis does not reveal the expected common motifs in the N-terminal portion of car, although they appear in the C-terminal portion. Nonetheless, when the motifs are searched for "visually", many of them are found, as shown in FIG. 3. FIG. 4, FIG. 5, and FIG. 6 show the locations of these motifs within Car, the *M. tuberculosis* homologue FadD9, and a yeast Aar. "Adenylation domain" motifs C, D, F, H and I are found in Car, although A, B, E, and G are not. The P-pantetheine attachment site, domain J, is clearly present, as are the reduction (R) domain and the NADP-binding domain.

TABLE 1

Comparison of amino acid sequence of N-terminal 740 aa of Car to database sequences using Blast analysis

| Organism | Sequence ID | Sequence function | Blast score | E value | % ID | % Positive |
|---|---|---|---|---|---|---|
| *M. tuberculosis* | FadD9 | Putative acyl-CoA synthetase | 764 | 0 | 57 | 72 |
| *M. bovis* BCG | 2.885331 | Not annotated | "2074" | $2.4 \times 10^{-213}$ | 57 | 72 |
| *M. leprae* | ML0484 | Putative acyl-CoA ligase | 769 | 0 | 54 | 70 |
| *M. smegmatis* | 3.09264 | Not annotated | "3528" | 0 | 61 | 75 |
| *S. coelicolor* | SCO2561 | Putative fatty acid-CoA ligase | 251 | $3.5 \times 10^{-29}$ | 29 | 50 |
| *S. coelicolor* | SCO4383 | Putative 4-coumarate: CoA ligase | 221 | $6.8 \times 10^{-18}$ | 28 | 42 |
| *Drosophila* | CG3961-PA | Hypothetical protein | 211 | $4 \times 10^{-53}$ | 31 | 49 |
| *Mus* | AAH31544 | Similar to fatty acid Co-A ligase | 202 | $2 \times 10^{-50}$ | 27 | 46 |
| *T. fusca* | Scaf 1 | Not annotated | 121 | $3 \times 10^{-28}$ | 25 | 41 |
| *Stigmatella aurantica* | MxaA | Non-ribosomal peptide synthetase (in myxalamid biosynthesis) | 39 | $7 \times 10^{-5}$ | 26 | 41 |
| *Schizosaccharomyces pombe* | P40976 | ☐-Aminoadipate reductase | 25 | 0.14 | 23 | 43 |
| *Candida albicans* | AAC02241 | ☐-Aminoadipate reductase | 25 | 0.18 | 22 | 40 |

Bold letters indicate genes known to make a particular enzyme.

TABLE 2

Comparison of amino acid sequence of C-terminal 482 aa of Car to database sequences using Blast analysis

| Organism | Sequence ID | Sequence function | Blast score | E value | % ID | % Positive |
|---|---|---|---|---|---|---|
| *M. tuberculosis* | FadD9 | Putative acyl-CoA synthetase | 583 | $10^{-165}$ | 61 | 74 |
| *M. bovis* BCG | 2.887365 | Not annotated | "1531" | $3 \times 10^{-155}$ | 60 | 74 |
| *M. leprae* | ML0484 | Putative acyl-CoA ligase | 555 | $1 \times 10^{-157}$ | 58 | 74 |
| *M. smegmatis* | 3.11301 | Not annotated | "1597" | $4.8 \times 10^{-164}$ | 62 | 77 |
| *S. coelicolor* | SCO6273 | Putative polyketide synthase | 323 | $1.6 \times 10^{-27}$ | 35 | 51 |
| *S. coelicolor* | SCO1273 | Putative reductase | 248 | $4.7 \times 10^{-28}$ | 39 | 52 |
| *Stigmatella aurantica* | MxaA | Non-ribosomal peptide synthetase (in myxalamid biosynthesis) | 148 | $2 \times 10^{-34}$ | 33 | 46 |
| *Schizosaccharomyces pombe* | P40976 | ☐-Aminoadipate reductase | 116 | $9 \times 10^{-25}$ | 27 | 46 |
| *Pichia farinosa* | CAB97252 | ☐-Aminoadipate reductase | 108 | $2 \times 10^{-22}$ | 25 | 42 |
| *T. fusca* | | No Hits | | | | |

Bold letters indicate genes known to make a particular enzyme.

What is claimed is:

1. An isolated polynucleotide encoding a carboxylic acid reductase, said polynucleotide selected from the group consisting of:
   (a) a polynucleotide having at least 95% nucleotide sequence identity to SEQ ID NO:1 encoding a polypeptide having carboxylic acid reductase activity;
   (b) a polynucleotide comprising SEQ ID NO:1 encoding a polypeptide having carboxylic acid reductase activity; and
   (c) a polynucleotide which is complementary to the full length of the polynucleotide of (a) or (b).

2. A recombinant expression cassette comprising a polynucleotide selected from the group consisting of:
   (a) a polynucleotide having at least 95% nucleotide sequence identity to SEQ ID NO:1 encoding a polypeptide having carboxylic acid reductase activity;
   (b) a polynucleotide comprising SEQ ID NO:1 encoding a polypeptide having carboxylic acid reductase activity; and
   (c) a polynucleotide which is complementary to the full length of the polynucleotide of (a) or (b).

3. A vector comprising a recombinant expression cassette comprising a polynucleotide selected from the group consisting of:
   (a) a polynucleotide having at least 95% nucleotide sequence identity to SEQ ID NO:1 encoding a polypeptide having carboxylic acid reductase activity;
   (b) a polynucleotide comprising SEQ ID NO:1 encoding a polypeptide having carboxylic acid reductase activity; and
   (c) a polynucleotide which is complementary to the full length of the polynucleotide of (a) or (b).

4. An isolated host cell transformed with a recombinant expression cassette which comprises a polynucleotide selected from the group consisting of:
   (a) a polynucleotide having at least 95% nucleotide sequence identity to SEQ ID NO:1 encoding a polypeptide having carboxylic acid reductase activity;
   (b) a polynucleotide comprising SEQ ID NO:1 encoding a polypeptide having carboxylic acid reductase activity; and
   (c) a polynucleotide which is complementary to the full length of the polynucleotide of (a) or (b).

5. The host cell of claim 4 wherein the cell is a bacterial cell.

6. The host cell of claim 5 wherein the cell is an *E. Coli* cell.

7. An isolated bacterial cell transformed with a polynucleotide selected from the group consisting of:
   (a) a polynucleotide having at least 95% nucleotide sequence identity to SEQ ID NO:1 encoding a polypeptide having carboxylic acid reductase activity;
   (b) a polynucleotide comprising SEQ ID NO:1 encoding a polypeptide having carboxylic acid reductase activity; and
   (c) a polynucleotide which is complementary to the full length of the polynucleotide of (a) or (b).

8. A method of making a carboxylic acid reductase enzyme comprising the steps of:
   a) expressing a polynucleotide in a bacterial host cell transformed with said polynucleotide, wherein the polynucleotide is selected from the group consisting of:
      i) a polynucleotide having at least 95% nucleotide sequence identity to SEQ ID NO:1 encoding a polypeptide having carboxylic acid reductase activity; and
      ii) a polynucleotide comprising SEQ ID NO:1 encoding a polypeptide having carboxylic acid reductase activity;
   b) culturing said bacterial cell under cell growth conditions; so that carboxylic acid reductase is produced and
   c) harvesting said carboxylic acid reductase.

* * * * *

SEQUENCE LISTING

<160> NUMBER OF SEQ ID NOS: 39

<210> SEQ ID NO 1
<211> LENGTH: 4600
<212> TYPE: DNA
<213> ORGANISM: Nocardia
<220> FEATURE:
<221> NAME/KEY: CDS
<222> LOCATION: (189)..(4598)
<223> OTHER INFORMATION:

<400> SEQUENCE: 1

```
ggtaccggca atacctggat aagcggtcgg atcctgggcc gctgcggtgg agtggccgcc      60
gttccggccc gatgtggcca agaccactcg agtcaccgcc gcgtatcacc ttcccggaag     120
tatttactta ggctaacgtg ttttacgggt tgcagggctt ttcctactta tgacaaggga     180 ggcttgcc atg gca gtg gat tca ccg gat gag cgg cta cag cgc cgc att      230
         Met Ala Val Asp Ser Pro Asp Glu Arg Leu Gln Arg Arg Ile
          1               5                  10 gca cag ttg ttt gca gaa gat gag cag gtc aag gcc gca cgt ccg ctc      278
Ala Gln Leu Phe Ala Glu Asp Glu Gln Val Lys Ala Ala Arg Pro Leu
 15                  20                  25                  30 gaa gcg gtg agc gcg gcg gtg agc gcg ccc ggt atg cgg ctg gcg cag      326
Glu Ala Val Ser Ala Ala Val Ser Ala Pro Gly Met Arg Leu Ala Gln
                 35                  40                  45 atc gcc gcc act gtt atg gcg ggt tac gcc gac cgc ccg gcc gcc ggg      374
Ile Ala Ala Thr Val Met Ala Gly Tyr Ala Asp Arg Pro Ala Ala Gly
             50                  55                  60 cag cgt gcg ttc gaa ctg aac acc gac gac gcg acg ggc cgc acc tcg      422
Gln Arg Ala Phe Glu Leu Asn Thr Asp Asp Ala Thr Gly Arg Thr Ser
 65                  70                  75 ctg cgg tta ctt ccc cga ttc gag acc atc acc tat cgc gaa ctg tgg      470
Leu Arg Leu Leu Pro Arg Phe Glu Thr Ile Thr Tyr Arg Glu Leu Trp
 80                  85                  90 cag cga gtc ggc gag gtt gcc gcg gcc tgg cat cat gat ccc gag aac      518
Gln Arg Val Gly Glu Val Ala Ala Ala Trp His His Asp Pro Glu Asn
 95                 100                 105                 110 ccc ttg cgc gca ggt gat ttc gtc gcc ctg ctc ggc ttc acc agc atc      566
Pro Leu Arg Ala Gly Asp Phe Val Ala Leu Leu Gly Phe Thr Ser Ile
                115                 120                 125 gac tac gcc acc ctc gac ctg gcc gat atc cac ctc ggc gcg gtt acc      614
Asp Tyr Ala Thr Leu Asp Leu Ala Asp Ile His Leu Gly Ala Val Thr
            130                 135                 140 gtg ccg ttg cag gcc agc gcg gcg gtg tcc cag ctg atc gct atc ctc      662
Val Pro Leu Gln Ala Ser Ala Ala Val Ser Gln Leu Ile Ala Ile Leu
            145                 150                 155 acc gag act tcg ccg cgg ctg ctc gcc tcg acc ccg gag cac ctc gat      710
Thr Glu Thr Ser Pro Arg Leu Leu Ala Ser Thr Pro Glu His Leu Asp
 160                 165                 170 gcg gcg gtc gag tgc cta ctc gcg ggc acc aca ccg gaa cga ctg gtg      758
Ala Ala Val Glu Cys Leu Leu Ala Gly Thr Thr Pro Glu Arg Leu Val
 175                 180                 185                 190 gtc ttc gac tac cac ccc gag gac gac gac cag cgt gcg gcc ttc gaa      806
Val Phe Asp Tyr His Pro Glu Asp Asp Asp Gln Arg Ala Ala Phe Glu
                195                 200                 205 tcc gcc cgc cgc cgc ctt gcc gac gcg ggc agc tcg gtg atc gtc gaa      854
Ser Ala Arg Arg Arg Leu Ala Asp Ala Gly Ser Ser Val Ile Val Glu
            210                 215                 220 acg ctc gat gcc gtg cgt gcc cgg ggc cgc gac tta ccg gcc gcg cca      902
```

|  |  |
|---|---|
| Thr Leu Asp Ala Val Arg Ala Arg Gly Arg Asp Leu Pro Ala Ala Pro<br>    225                           230                        235 | |
| ctg ttc gtt ccc gac acc gac gac gac ccg ctg gcc ctg ctg atc tac<br>Leu Phe Val Pro Asp Thr Asp Asp Asp Pro Leu Ala Leu Leu Ile Tyr<br>    240                           245                        250 | 950 |
| acc tcc ggc agc acc gga acg ccg aag ggc gcg atg tac acc aat cgg<br>Thr Ser Gly Ser Thr Gly Thr Pro Lys Gly Ala Met Tyr Thr Asn Arg<br>255                           260                        265                        270 | 998 |
| ttg gcc gcc acg atg tgg cag ggg aac tcg atg ctg cag ggg aac tcg<br>Leu Ala Ala Thr Met Trp Gln Gly Asn Ser Met Leu Gln Gly Asn Ser<br>                         275                        280                        285 | 1046 |
| caa cgg gtc ggg atc aat ctc aac tac atg ccg atg agc cac atc gcc<br>Gln Arg Val Gly Ile Asn Leu Asn Tyr Met Pro Met Ser His Ile Ala<br>              290                        295                        300 | 1094 |
| ggt cgc ata tcg ctg ttc ggc gtg ctc gct cgc ggt ggc acc gca tac<br>Gly Arg Ile Ser Leu Phe Gly Val Leu Ala Arg Gly Gly Thr Ala Tyr<br>        305                        310                        315 | 1142 |
| ttc gcg gcc aag agc gac atg tcg aca ctg ttc gaa gac atc ggc ttg<br>Phe Ala Ala Lys Ser Asp Met Ser Thr Leu Phe Glu Asp Ile Gly Leu<br>    320                         325                        330 | 1190 |
| gta cgt ccc acc gag atc ttc ttc gtc ccg cgc gtg tgc gac atg gtc<br>Val Arg Pro Thr Glu Ile Phe Phe Val Pro Arg Val Cys Asp Met Val<br>335                         340                        345                        350 | 1238 |
| ttc cag cgc tat cag agc gag ctg gac cgg cgc tcg gtg gcg ggc gcc<br>Phe Gln Arg Tyr Gln Ser Glu Leu Asp Arg Arg Ser Val Ala Gly Ala<br>                         355                        360                        365 | 1286 |
| gac ctg gac acg ctc gat cgg gaa gtg aaa gcc gac ctc cgg cag aac<br>Asp Leu Asp Thr Leu Asp Arg Glu Val Lys Ala Asp Leu Arg Gln Asn<br>              370                        375                        380 | 1334 |
| tac ctc ggt ggg cgc ttc ctg gtg gcg gtc gtc ggc agc gcg ccg ctg<br>Tyr Leu Gly Gly Arg Phe Leu Val Ala Val Val Gly Ser Ala Pro Leu<br>        385                        390                        395 | 1382 |
| gcc gcg gag atg aag acg ttc atg gag tcc gtc ctc gat ctg cca ctg<br>Ala Ala Glu Met Lys Thr Phe Met Glu Ser Val Leu Asp Leu Pro Leu<br>    400                         405                        410 | 1430 |
| cac gac ggg tac ggg tcg acc gag gcg ggc gca agc gtg ctg ctc gac<br>His Asp Gly Tyr Gly Ser Thr Glu Ala Gly Ala Ser Val Leu Leu Asp<br>415                         420                        425                        430 | 1478 |
| aac cag atc cag cgg ccg ccg gtg ctc gat tac aag ctc gtc gac gtg<br>Asn Gln Ile Gln Arg Pro Pro Val Leu Asp Tyr Lys Leu Val Asp Val<br>                         435                        440                        445 | 1526 |
| ccc gaa ctg ggt tac ttc cgc acc gac cgg ccg cat ccg cgc ggt gag<br>Pro Glu Leu Gly Tyr Phe Arg Thr Asp Arg Pro His Pro Arg Gly Glu<br>            450                        455                        460 | 1574 |
| ctg ttg ttg aag gcg gag acc acg att ccg ggc tac tac aag cgg ccc<br>Leu Leu Leu Lys Ala Glu Thr Thr Ile Pro Gly Tyr Tyr Lys Arg Pro<br>              465                        470                        475 | 1622 |
| gag gtc acc gcg gag atc ttc gac gag gac ggc ttc tac aag acc ggc<br>Glu Val Thr Ala Glu Ile Phe Asp Glu Asp Gly Phe Tyr Lys Thr Gly<br>                     480                        485                        490 | 1670 |
| gat atc gtg gcc gag ctc gag cac gat cgg ctg gtc tat gtc gac cgt<br>Asp Ile Val Ala Glu Leu Glu His Asp Arg Leu Val Tyr Val Asp Arg<br>495                         500                        505                        510 | 1718 |
| cgc aac aat gtg ctc aaa ctg tcg cag ggc gag ttc gtg acc gtc gcc<br>Arg Asn Asn Val Leu Lys Leu Ser Gln Gly Glu Phe Val Thr Val Ala<br>                         515                        520                        525 | 1766 |
| cat ctc gag gcc gtg ttc gcc agc agc ccg ctg atc cgg cag atc ttc<br>His Leu Glu Ala Val Phe Ala Ser Ser Pro Leu Ile Arg Gln Ile Phe<br>              530                        535                        540 | 1814 |

-continued

| | |
|---|---|
| atc tac ggc agc agc gaa cgt tcc tat ctg ctc gcg gtg atc gtc ccc<br>Ile Tyr Gly Ser Ser Glu Arg Ser Tyr Leu Leu Ala Val Ile Val Pro<br>545                550                555 | 1862 |
| acc gac gac gcg ctg cgc ggc cgc gac acc gcc acc ttg aaa tcg gca<br>Thr Asp Asp Ala Leu Arg Gly Arg Asp Thr Ala Thr Leu Lys Ser Ala<br>560                565                570 | 1910 |
| ctg gcc gaa tcg att cag cgc atc gcc aag gac gcg aac ctg cag ccc<br>Leu Ala Glu Ser Ile Gln Arg Ile Ala Lys Asp Ala Asn Leu Gln Pro<br>575                580                585                590 | 1958 |
| tac gag att ccg cgc gat ttc ctg atc gag acc gag ccg ttc acc atc<br>Tyr Glu Ile Pro Arg Asp Phe Leu Ile Glu Thr Glu Pro Phe Thr Ile<br>595                600                605 | 2006 |
| gcc aac gga ctg ctc tcc ggc atc gcg aag ctg ctg cgc ccc aat ctg<br>Ala Asn Gly Leu Leu Ser Gly Ile Ala Lys Leu Leu Arg Pro Asn Leu<br>610                615                620 | 2054 |
| aag gaa cgc tac ggc gct cag ctg gag cag atg tac acc gat ctc gcg<br>Lys Glu Arg Tyr Gly Ala Gln Leu Glu Gln Met Tyr Thr Asp Leu Ala<br>625                630                635 | 2102 |
| aca ggc cag gcc gat gag ctg ctc gcc ctg cgc cgc gaa gcc gcc gac<br>Thr Gly Gln Ala Asp Glu Leu Leu Ala Leu Arg Arg Glu Ala Ala Asp<br>640                645                650 | 2150 |
| ctg ccg gtg ctc gaa acc gtc agc cgg gca gcg aaa gcg atg ctc ggc<br>Leu Pro Val Leu Glu Thr Val Ser Arg Ala Ala Lys Ala Met Leu Gly<br>655                660                665                670 | 2198 |
| gtc gcc tcc gcc gat atg cgt ccc gac gcg cac ttc acc gac ctg ggc<br>Val Ala Ser Ala Asp Met Arg Pro Asp Ala His Phe Thr Asp Leu Gly<br>675                680                685 | 2246 |
| ggc gat tcc ctt tcc gcg ctg tcg ttc tcg aac ctg ctg cac gag atc<br>Gly Asp Ser Leu Ser Ala Leu Ser Phe Ser Asn Leu Leu His Glu Ile<br>690                695                700 | 2294 |
| ttc ggg gtc gag gtg ccg gtg ggt gtc gtc agc ccg gcg aac gag<br>Phe Gly Val Glu Val Pro Val Gly Val Val Ser Pro Ala Asn Glu<br>705                710                715 | 2342 |
| ctg cgc gat ctg gcg aat tac att gag gcg gaa cgc aac tcg ggc gcg<br>Leu Arg Asp Leu Ala Asn Tyr Ile Glu Ala Glu Arg Asn Ser Gly Ala<br>720                725                730 | 2390 |
| aag cgt ccc acc ttc acc tcg gtg cac ggc ggc ggt tcc gag atc cgc<br>Lys Arg Pro Thr Phe Thr Ser Val His Gly Gly Gly Ser Glu Ile Arg<br>735                740                745                750 | 2438 |
| gcc gcc gat ctg acc ctc gac aag ttc atc gat gcc cgc acc ctg gcc<br>Ala Ala Asp Leu Thr Leu Asp Lys Phe Ile Asp Ala Arg Thr Leu Ala<br>755                760                765 | 2486 |
| gcc gcc gac agc att ccg cac gcg ccg gtg cca gcg cag acg gtg ctg<br>Ala Ala Asp Ser Ile Pro His Ala Pro Val Pro Ala Gln Thr Val Leu<br>770                775                780 | 2534 |
| ctg acc ggc gcg aac ggc tac ctc ggc cgg ttc ctg tgc ctg gaa tgg<br>Leu Thr Gly Ala Asn Gly Tyr Leu Gly Arg Phe Leu Cys Leu Glu Trp<br>785                790                795 | 2582 |
| ctg gag cgg ctg gac aag acg ggt ggc acg ctg atc tgc gtc gtg cgc<br>Leu Glu Arg Leu Asp Lys Thr Gly Gly Thr Leu Ile Cys Val Val Arg<br>800                805                810 | 2630 |
| ggt agt gac gcg gcc gcg gcc cgt aaa cgg ctg gac tcg gcg ttc gac<br>Gly Ser Asp Ala Ala Ala Arg Lys Arg Leu Asp Ser Ala Phe Asp<br>815              820                825                830 | 2678 |
| agc ggc gat ccc ggc ctg ctc gag cac tac cag caa ctg gcc gca cgg<br>Ser Gly Asp Pro Gly Leu Leu Glu His Tyr Gln Gln Leu Ala Ala Arg<br>835                840                845 | 2726 |
| acc ctg gaa gtc ctc gcc ggt gat atc ggc gac ccg aat ctc ggt ctg<br>Thr Leu Glu Val Leu Ala Gly Asp Ile Gly Asp Pro Asn Leu Gly Leu<br>850                855                860 | 2774 |

-continued

| | |
|---|---|
| gac gac gcg act tgg cag cgg ttg gcc gaa acc gtc gac ctg atc gtc<br>Asp Asp Ala Thr Trp Gln Arg Leu Ala Glu Thr Val Asp Leu Ile Val<br>              865              870              875 | 2822 |
| cat ccc gcc gcg ttg gtc aac cac gtc ctt ccc tac acc cag ctg ttc<br>His Pro Ala Ala Leu Val Asn His Val Leu Pro Tyr Thr Gln Leu Phe<br>     880               885              890 | 2870 |
| ggc ccc aat gtc gtc ggc acc gcc gaa atc gtc cgg ttg gcg atc acg<br>Gly Pro Asn Val Val Gly Thr Ala Glu Ile Val Arg Leu Ala Ile Thr<br>895              900              905              910 | 2918 |
| gcg cgg cgc aag ccg gtc acc tac ctg tcg acc gtc gga gtg gcc gac<br>Ala Arg Arg Lys Pro Val Thr Tyr Leu Ser Thr Val Gly Val Ala Asp<br>              915              920              925 | 2966 |
| cag gtc gac ccg gcg gag tat cag gag gac agc gac gtc cgc gag atg<br>Gln Val Asp Pro Ala Glu Tyr Gln Glu Asp Ser Asp Val Arg Glu Met<br>     930               935              940 | 3014 |
| agc gcg gtg cgc gtc gtg cgc gag agt tac gcc aac ggc tac ggc aac<br>Ser Ala Val Arg Val Val Arg Glu Ser Tyr Ala Asn Gly Tyr Gly Asn<br>945              950              955 | 3062 |
| agc aag tgg gcg ggg gag gtc ctg ctg cgc gaa gca cac gat ctg tgt<br>Ser Lys Trp Ala Gly Glu Val Leu Leu Arg Glu Ala His Asp Leu Cys<br>              960              965              970 | 3110 |
| ggc ttg ccg gtc gcg gtg ttc cgt tcg gac atg atc ctg gcg cac agc<br>Gly Leu Pro Val Ala Val Phe Arg Ser Asp Met Ile Leu Ala His Ser<br>975              980              985              990 | 3158 |
| cgg tac gcg ggt cag ctc aac gtc cag gac gtg ttc acc cgg ctg atc<br>Arg Tyr Ala Gly Gln Leu Asn Val Gln Asp Val Phe Thr Arg Leu Ile<br>              995              1000           1005 | 3206 |
| ctc agc ctg gtc gcc acc ggc atc gcg ccg tac tcg ttc tac cga<br>Leu Ser Leu Val Ala Thr Gly Ile Ala Pro Tyr Ser Phe Tyr Arg<br>           1010            1015           1020 | 3251 |
| acc gac gcg gac ggc aac cgg cag cgg gcc cac tac gac ggt ctg<br>Thr Asp Ala Asp Gly Asn Arg Gln Arg Ala His Tyr Asp Gly Leu<br>           1025            1030           1035 | 3296 |
| ccc gcc gat ttc acg gcg gcg gcg atc acc gcg ctc ggc atc caa<br>Pro Ala Asp Phe Thr Ala Ala Ala Ile Thr Ala Leu Gly Ile Gln<br>           1040            1045           1050 | 3341 |
| gcc acc gaa ggc ttc cgg acc tac gac gtg ctc aat ccg tac gac<br>Ala Thr Glu Gly Phe Arg Thr Tyr Asp Val Leu Asn Pro Tyr Asp<br>           1055            1060           1065 | 3386 |
| gat ggc atc tcc ctc gat gaa ttc gtc gac tgg ctc gtc gaa tcc<br>Asp Gly Ile Ser Leu Asp Glu Phe Val Asp Trp Leu Val Glu Ser<br>           1070            1075           1080 | 3431 |
| ggc cac ccg atc cag cgc atc acc gac tac agc gac tgg ttc cac<br>Gly His Pro Ile Gln Arg Ile Thr Asp Tyr Ser Asp Trp Phe His<br>           1085            1090           1095 | 3476 |
| cgt ttc gag acg gcg atc cgc gcg ctg ccg gaa aag caa cgc cag<br>Arg Phe Glu Thr Ala Ile Arg Ala Leu Pro Glu Lys Gln Arg Gln<br>           1100            1105           1110 | 3521 |
| gcc tcg gtg ctg ccg ttg ctg gac gcc tac cgc aac ccc tgc ccg<br>Ala Ser Val Leu Pro Leu Leu Asp Ala Tyr Arg Asn Pro Cys Pro<br>           1115            1120           1125 | 3566 |
| gcg gtc cgc ggc gcg ata ctc ccg gcc aag gag ttc caa gcg gcg<br>Ala Val Arg Gly Ala Ile Leu Pro Ala Lys Glu Phe Gln Ala Ala<br>           1130            1135           1140 | 3611 |
| gtg caa aca gcc aaa atc ggt ccg gaa cag gac atc ccg cat ttg<br>Val Gln Thr Ala Lys Ile Gly Pro Glu Gln Asp Ile Pro His Leu<br>           1145            1150           1155 | 3656 |
| tcc gcg cca ctg atc gat aag tac gtc agc gat ctg gaa ctg ctt<br>Ser Ala Pro Leu Ile Asp Lys Tyr Val Ser Asp Leu Glu Leu Leu | 3701 |

-continued

|  |  |  |  |
|---|---|---|---|
| 1160 | 1165 | 1170 | |
| cag ctg ctc tga cgg ata tca ggc cgc cgc gcg cac ctc gtc ggt<br>Gln Leu Leu     Arg Ile Ser Gly Arg Arg Ala His Leu Val Gly<br>                            1175                         1180                       1185 | | 3746 |
| gcg ttc ggc gcc ttc gcg ccg gag gcg aaa cag gaa tac cgc cga<br>Ala Phe Gly Ala Phe Ala Pro Glu Ala Lys Gln Glu Tyr Arg Arg<br>              1190                           1195                          1200 | | 3791 |
| gcc acc cag gac agc ggc gta gac gat gac gaa gct gtt gat cag<br>Ala Thr Gln Asp Ser Gly Val Asp Asp Asp Glu Ala Val Asp Gln<br>                     1205                        1210                         1215 | | 3836 |
| gac ctg ggc gac cgg cca cca cgg cgg gaa cag gaa cag ccc gac<br>Asp Leu Gly Asp Arg Pro Pro Arg Arg Glu Gln Glu Gln Pro Asp<br>                      1220                        1225                          1230 | | 3881 |
| gac aac gta gtc cgg gct gta ttc cca cgt cca cgc gcc gat cga<br>Asp Asn Val Val Arg Ala Val Phe Pro Arg Pro Arg Ala Asp Arg<br>                  1235                          1240                        1245 | | 3926 |
| gac gaa gag cgc ggc cga ggc aag cca cca cca cgg ctg cga ctg<br>Asp Glu Glu Arg Gly Arg Gly Lys Pro Pro Pro Arg Leu Arg Leu<br>                      1250                       1255                         1260 | | 3971 |
| cgc cct gtg cag tag ata gac gaa cag ggg aac gaa cca cac cca<br>Arg Pro Val Gln     Ile Asp Glu Gln Gly Asn Glu Pro His Pro<br>                         1265                          1270 | | 4016 |
| gtg gtg gtc cca gga gaa cgg cga gac cgc gca ggc ggt gag gcc<br>Val Val Val Pro Gly Glu Arg Arg Asp Arg Ala Gly Gly Glu Ala<br>1275                        1280                          1285 | | 4061 |
| ggc gag ggt gac cgc gag gag ctg ttc gcc acg ccg ata cag gcc<br>Gly Glu Gly Asp Arg Glu Glu Leu Phe Ala Thr Pro Ile Gln Ala<br>1290                        1295                          1300 | | 4106 |
| gat ggt gac ggc cag act cgc cag cgc gac gga gcc cgc gat gag<br>Asp Gly Asp Gly Gln Thr Arg Gln Arg Asp Gly Ala Arg Asp Glu<br>1305                        1310                          1315 | | 4151 |
| cag cca cag cca cac cgg cgc cgg gtg atg ggt cag gtg cgc gat<br>Gln Pro Gln Pro His Arg Arg Arg Val Met Gly Gln Val Arg Asp<br>1320                        1325                          1330 | | 4196 |
| ggc gcc gcg gat gga ttg att gga cgg gtg cat atc gtc cgc gat<br>Gly Ala Ala Asp Gly Leu Ile Gly Arg Val His Ile Val Arg Asp<br>1335                        1340                          1345 | | 4241 |
| ccg att gga ctg gaa gaa cgt cga ggt cca gta ctg ccg gga atc<br>Pro Ile Gly Leu Glu Glu Arg Arg Gly Pro Val Leu Pro Gly Ile<br>1350                        1355                          1360 | | 4286 |
| ggc ggg cag cac gat cca ggc gag gac gat gga cgc gat gaa cac<br>Gly Gly Gln His Asp Pro Gly Glu Asp Asp Gly Arg Asp Glu His<br>1365                        1370                          1375 | | 4331 |
| cgc cac ggc ggt gca cgc gga ccg cca ctg ccg caa cgc gag gaa<br>Arg His Gly Gly Ala Arg Gly Pro Pro Leu Pro Gln Arg Glu Glu<br>1380                        1385                          1390 | | 4376 |
| ttg cac gac gaa gta gcc agg gac gag ctt gat gcc cgc cgc cac<br>Leu His Asp Glu Val Ala Arg Asp Glu Leu Asp Ala Arg Arg His<br>1395                        1400                          1405 | | 4421 |
| ccc gac gcc gag gcc gcg cag ctt gct gcg gtc ggg ccg gga gaa<br>Pro Asp Ala Glu Ala Ala Gln Leu Ala Ala Val Gly Pro Gly Glu<br>1410                        1415                          1420 | | 4466 |
| gtc cca cag cac cag cag cat cag cat cag gtt gat ctg gcc gta<br>Val Pro Gln His Gln Gln His Gln His Gln Val Asp Leu Ala Val<br>1425                        1430                          1435 | | 4511 |
| gaa cag cgt tgt ccg gac ggg ctc gat gaa cgc gca ggt gag cgc<br>Glu Gln Arg Cys Pro Asp Gly Leu Asp Glu Arg Ala Gly Glu Arg<br>1440                        1445                          1450 | | 4556 |
| cag tag ggc gct gac gac ggc cag tct ggc gtt gat ccg gta cc | | 4600 |

```
Gln         Gly Ala Asp Asp Gly  Gln Ser Gly Val Asp  Pro Val
1455                    1460                 1465

<210> SEQ ID NO 2
<211> LENGTH: 1174
<212> TYPE: PRT
<213> ORGANISM: Nocardia

<400> SEQUENCE: 2

Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Ser Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
                260                 265                 270

Ala Thr Met Trp Gln Gly Asn Ser Met Leu Gln Gly Asn Ser Gln Arg
            275                 280                 285

Val Gly Ile Asn Leu Asn Tyr Met Pro Met Ser His Ile Ala Gly Arg
        290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
                340                 345                 350

Arg Tyr Gln Ser Glu Leu Asp Arg Arg Ser Val Ala Gly Ala Asp Leu
            355                 360                 365
```

-continued

```
Asp Thr Leu Asp Arg Glu Val Lys Ala Asp Leu Arg Gln Asn Tyr Leu
    370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
            420                 425                 430

Ile Gln Arg Pro Pro Val Leu Asp Tyr Lys Leu Val Asp Val Pro Glu
        435                 440                 445

Leu Gly Tyr Phe Arg Thr Asp Arg Pro His Pro Arg Gly Glu Leu Leu
    450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
    530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
    610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
    690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
        755                 760                 765

Asp Ser Ile Pro His Ala Pro Val Pro Ala Gln Thr Val Leu Leu Thr
    770                 775                 780
```

-continued

```
Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
            805                 810                 815

Asp Ala Ala Ala Arg Lys Arg Leu Asp Ser Ala Phe Asp Ser Gly
        820                 825                 830

Asp Pro Gly Leu Leu Glu His Tyr Gln Gln Leu Ala Ala Arg Thr Leu
        835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
                900                 905                 910

Arg Lys Pro Val Thr Tyr Leu Ser Thr Val Gly Val Ala Asp Gln Val
            915                 920                 925

Asp Pro Ala Glu Tyr Gln Glu Asp Ser Asp Val Arg Glu Met Ser Ala
930                 935                 940

Val Arg Val Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
                980                 985                 990

Ala Gly Gln Leu Asn Val Gln Asp  Val Phe Thr Arg Leu  Ile Leu Ser
        995                 1000                1005

Leu Val  Ala Thr Gly Ile Ala  Pro Tyr Ser Phe Tyr  Arg Thr Asp
    1010                1015                1020

Ala Asp  Gly Asn Arg Gln Arg  Ala His Tyr Asp Gly  Leu Pro Ala
    1025                1030                1035

Asp Phe  Thr Ala Ala Ala Ile  Thr Ala Leu Gly Ile  Gln Ala Thr
    1040                1045                1050

Glu Gly  Phe Arg Thr Tyr Asp  Val Leu Asn Pro Tyr  Asp Asp Gly
    1055                1060                1065

Ile Ser  Leu Asp Glu Phe Val  Asp Trp Leu Val Glu   Ser Gly His
    1070                1075                1080

Pro Ile  Gln Arg Ile Thr Asp  Tyr Ser Asp Trp Phe  His Arg Phe
    1085                1090                1095

Glu Thr  Ala Ile Arg Ala Leu  Pro Glu Lys Gln Arg   Gln Ala Ser
    1100                1105                1110

Val Leu  Pro Leu Leu Asp Ala  Tyr Arg Asn Pro Cys  Pro Ala Val
    1115                1120                1125

Arg Gly  Ala Ile Leu Pro Ala  Lys Glu Phe Gln Ala   Ala Val Gln
    1130                1135                1140

Thr Ala  Lys Ile Gly Pro Glu  Gln Asp Ile Pro His  Leu Ser Ala
    1145                1150                1155

Pro Leu  Ile Asp Lys Tyr Val  Ser Asp Leu Glu Leu  Leu Gln Leu
    1160                1165                1170

Leu
```

<210> SEQ ID NO 3

```
<211> LENGTH: 90
<212> TYPE: PRT
<213> ORGANISM: Nocardia

<400> SEQUENCE: 3

Arg Ile Ser Gly Arg Arg Ala His Leu Val Gly Ala Phe Gly Ala Phe
1               5                   10                  15

Ala Pro Glu Ala Lys Gln Glu Tyr Arg Arg Ala Thr Gln Asp Ser Gly
            20                  25                  30

Val Asp Asp Glu Ala Val Asp Gln Asp Leu Gly Asp Arg Pro Pro
        35                  40                  45

Arg Arg Glu Gln Glu Gln Pro Asp Asp Asn Val Val Arg Ala Val Phe
    50                  55                  60

Pro Arg Pro Arg Ala Asp Arg Asp Glu Glu Arg Gly Arg Gly Lys Pro
65                  70                  75                  80

Pro Pro Arg Leu Arg Leu Arg Pro Val Gln
                85                  90

<210> SEQ ID NO 4
<211> LENGTH: 191
<212> TYPE: PRT
<213> ORGANISM: Nocardia

<400> SEQUENCE: 4

Ile Asp Glu Gln Gly Asn Glu Pro His Pro Val Val Pro Gly Glu
1               5                   10                  15

Arg Arg Asp Arg Ala Gly Gly Glu Ala Gly Glu Gly Asp Arg Glu Glu
            20                  25                  30

Leu Phe Ala Thr Pro Ile Gln Ala Asp Gly Asp Gly Gln Thr Arg Gln
            35                  40                  45

Arg Asp Gly Ala Arg Asp Glu Gln Pro Gln Pro His Arg Arg Arg Val
    50                  55                  60

Met Gly Gln Val Arg Asp Gly Ala Ala Asp Gly Leu Ile Gly Arg Val
65                  70                  75                  80

His Ile Val Arg Asp Pro Ile Gly Leu Glu Glu Arg Arg Gly Pro Val
                85                  90                  95

Leu Pro Gly Ile Gly Gly Gln His Asp Pro Gly Glu Asp Asp Gly Arg
            100                 105                 110

Asp Glu His Arg His Gly Gly Ala Arg Gly Pro Pro Leu Pro Gln Arg
        115                 120                 125

Glu Glu Leu His Asp Glu Val Ala Arg Asp Glu Leu Asp Ala Arg Arg
    130                 135                 140

His Pro Asp Ala Glu Ala Ala Gln Leu Ala Ala Val Gly Pro Gly Glu
145                 150                 155                 160

Val Pro Gln His Gln Gln His Gln Val Asp Leu Ala Val Glu
                165                 170                 175

Gln Arg Cys Pro Asp Gly Leu Asp Arg Ala Gly Glu Arg Gln
            180                 185                 190

<210> SEQ ID NO 5
<211> LENGTH: 12
<212> TYPE: PRT
<213> ORGANISM: Nocardia

<400> SEQUENCE: 5

Gly Ala Asp Asp Gly Gln Ser Gly Val Asp Pro Val
1               5                   10
```

-continued

```
<210> SEQ ID NO 6
<211> LENGTH: 16
<212> TYPE: PRT
<213> ORGANISM: Nocardia

<400> SEQUENCE: 6

Ala Val Asp Ser Pro Asp Glu Arg Leu Gln Arg Arg Ile Ala Gln Leu
1               5                   10                  15

<210> SEQ ID NO 7
<211> LENGTH: 16
<212> TYPE: PRT
<213> ORGANISM: Nocardia

<400> SEQUENCE: 7

Lys Leu Ser Gln Gly Glu Phe Val Thr Val Ala His Leu Glu Ala Val
1               5                   10                  15

<210> SEQ ID NO 8
<211> LENGTH: 8
<212> TYPE: PRT
<213> ORGANISM: hypothetical
<220> FEATURE:
<221> NAME/KEY: MISC_FEATURE
<222> LOCATION: (7)..(7)
<223> OTHER INFORMATION: "X" can ba any animo acid
<220> FEATURE:
<221> NAME/KEY: MISC_FEATURE
<222> LOCATION: (4)..(4)
<223> OTHER INFORMATION: "X" can ba any animo acid
<220> FEATURE:
<221> NAME/KEY: MISC_FEATURE
<222> LOCATION: (6)..(6)
<223> OTHER INFORMATION: "X" can ba any animo acid

<400> SEQUENCE: 8

Leu Gly Gly Xaa Ser Xaa Xaa Ala
1               5

<210> SEQ ID NO 9
<211> LENGTH: 7
<212> TYPE: PRT
<213> ORGANISM: hypothetical
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be any amino acid

<400> SEQUENCE: 9

Gly Tyr Xaa Xaa Ser Lys Trp
1               5

<210> SEQ ID NO 10
<211> LENGTH: 7
<212> TYPE: PRT
<213> ORGANISM: hypothetical
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
```

```
<222> LOCATION: (5)..(5)
<223> OTHER INFORMATION: X can be any amino acid

<400> SEQUENCE: 10

Gly Xaa Xaa Gly Xaa Leu Gly
1               5

<210> SEQ ID NO 11
<211> LENGTH: 18
<212> TYPE: DNA
<213> ORGANISM: Nocardia

<400> SEQUENCE: 11
gtsgattcac csgatgag                                                 18

<210> SEQ ID NO 12
<211> LENGTH: 18
<212> TYPE: DNA
<213> ORGANISM: Nocardia

<400> SEQUENCE: 12
ccsgatgarc gsctacag                                                 18

<210> SEQ ID NO 13
<211> LENGTH: 18
<212> TYPE: DNA
<213> ORGANISM: Nocardia

<400> SEQUENCE: 13
tgsgcsacsg tsacgaac                                                 18

<210> SEQ ID NO 14
<211> LENGTH: 19
<212> TYPE: DNA
<213> ORGANISM: Nocardia

<400> SEQUENCE: 14
sacgaaytcs ccctgsgac                                                19

<210> SEQ ID NO 15
<211> LENGTH: 25
<212> TYPE: DNA
<213> ORGANISM: Nocardia

<400> SEQUENCE: 15
ggtcgggatc aatctcaact acatg                                         25

<210> SEQ ID NO 16
<211> LENGTH: 26
<212> TYPE: DNA
<213> ORGANISM: Nocardia

<400> SEQUENCE: 16
cttcagctgc tctgacggat atcagc                                        26

<210> SEQ ID NO 17
<211> LENGTH: 24
<212> TYPE: DNA
<213> ORGANISM: Nocardia

<400> SEQUENCE: 17
ctgctcatct tctgcaaaca actg                                          24
```

```
<210> SEQ ID NO 18
<211> LENGTH: 31
<212> TYPE: DNA
<213> ORGANISM: Nocardia

<400> SEQUENCE: 18
cgcggatccg cagtggattc accggatgag c                              31

<210> SEQ ID NO 19
<211> LENGTH: 32
<212> TYPE: DNA
<213> ORGANISM: Nocardia

<400> SEQUENCE: 19
cggggtaccc ctgatatccg tcagagcagc tg                             32

<210> SEQ ID NO 20
<211> LENGTH: 20
<212> TYPE: DNA
<213> ORGANISM: Nocardia

<400> SEQUENCE: 20
taatacgact cactataggg                                           20

<210> SEQ ID NO 21
<211> LENGTH: 24
<212> TYPE: DNA
<213> ORGANISM: Nocardia

<400> SEQUENCE: 21
catacgattt aggtgacact atag                                      24

<210> SEQ ID NO 22
<211> LENGTH: 18
<212> TYPE: DNA
<213> ORGANISM: Nocardia

<400> SEQUENCE: 22
caggaaacag ctatgacc                                             18

<210> SEQ ID NO 23
<211> LENGTH: 21
<212> TYPE: DNA
<213> ORGANISM: Nocardia

<400> SEQUENCE: 23
ctcgacctgg ccgatatcca c                                         21

<210> SEQ ID NO 24
<211> LENGTH: 20
<212> TYPE: DNA
<213> ORGANISM: Nocardia

<400> SEQUENCE: 24
gaggacggct tctacaagac                                           20

<210> SEQ ID NO 25
<211> LENGTH: 21
<212> TYPE: DNA
<213> ORGANISM: Nocardia

<400> SEQUENCE: 25
gacgcgcact tcaccgacct g                                         21
```

-continued

```
<210> SEQ ID NO 26
<211> LENGTH: 20
<212> TYPE: DNA
<213> ORGANISM: Nocardia

<400> SEQUENCE: 26
gtcgacctga tcgtccatcc                                              20

<210> SEQ ID NO 27
<211> LENGTH: 19
<212> TYPE: DNA
<213> ORGANISM: Nocardia

<400> SEQUENCE: 27
acctacgacg tgctcaatc                                               19

<210> SEQ ID NO 28
<211> LENGTH: 19
<212> TYPE: DNA
<213> ORGANISM: Nocardia

<400> SEQUENCE: 28
cgtacgacga tggcatctc                                               19

<210> SEQ ID NO 29
<211> LENGTH: 21
<212> TYPE: DNA
<213> ORGANISM: Nocardia

<400> SEQUENCE: 29
gtggatatcg gccaggtcga g                                            21

<210> SEQ ID NO 30
<211> LENGTH: 19
<212> TYPE: DNA
<213> ORGANISM: Nocardia

<400> SEQUENCE: 30
ggtggcagga tggaatcgg                                               19

<210> SEQ ID NO 31
<211> LENGTH: 20
<212> TYPE: DNA
<213> ORGANISM: Nocardia

<400> SEQUENCE: 31
cgtcgattcg cgattccctg                                              20

<210> SEQ ID NO 32
<211> LENGTH: 1168
<212> TYPE: PRT
<213> ORGANISM: M. tuberculosis

<400> SEQUENCE: 32

Met Ser Ile Asn Asp Gln Arg Leu Thr Arg Arg Val Glu Asp Leu Tyr
1               5                   10                  15

Ala Ser Asp Ala Gln Phe Ala Ala Ala Ser Pro Asn Glu Ala Ile Thr
            20                  25                  30

Gln Ala Ile Asp Gln Pro Gly Val Ala Leu Pro Gln Leu Ile Arg Met
        35                  40                  45

Val Met Glu Gly Tyr Ala Asp Arg Pro Ala Leu Gly Gln Arg Ala Leu
    50                  55                  60
```

```
Arg Phe Val Thr Asp Pro Asp Ser Gly Arg Thr Met Val Glu Leu Leu
 65                  70                  75                  80

Pro Arg Phe Glu Thr Ile Thr Tyr Arg Glu Leu Trp Ala Arg Ala Gly
                 85                  90                  95

Thr Leu Ala Thr Ala Leu Ser Ala Glu Pro Ala Ile Arg Pro Gly Asp
            100                 105                 110

Arg Val Cys Val Leu Gly Phe Asn Ser Val Asp Tyr Thr Thr Ile Asp
        115                 120                 125

Ile Ala Leu Ile Arg Leu Gly Ala Val Ser Val Pro Leu Gln Thr Ser
130                 135                 140

Ala Pro Val Thr Gly Leu Arg Pro Ile Val Thr Glu Thr Glu Pro Thr
145                 150                 155                 160

Met Ile Ala Thr Ser Ile Asp Asn Leu Gly Asp Ala Val Glu Val Leu
                165                 170                 175

Ala Gly His Ala Pro Ala Arg Leu Val Val Phe Asp Tyr His Gly Lys
            180                 185                 190

Val Asp Thr His Arg Glu Ala Val Glu Ala Ala Arg Ala Arg Leu Ala
        195                 200                 205

Gly Ser Val Thr Ile Asp Thr Leu Ala Glu Leu Ile Glu Arg Gly Arg
210                 215                 220

Ala Leu Pro Ala Thr Pro Ile Ala Asp Ser Ala Asp Ala Leu Ala
225                 230                 235                 240

Leu Leu Ile Tyr Thr Ser Gly Ser Thr Gly Ala Pro Lys Gly Ala Met
                245                 250                 255

Tyr Arg Glu Ser Gln Val Met Ser Phe Trp Arg Lys Ser Ser Gly Trp
            260                 265                 270

Phe Glu Pro Ser Gly Tyr Pro Ser Ile Thr Leu Asn Phe Met Pro Met
        275                 280                 285

Ser His Val Gly Gly Arg Gln Val Leu Tyr Gly Thr Leu Ser Asn Gly
    290                 295                 300

Gly Thr Ala Tyr Phe Val Ala Lys Ser Asp Leu Ser Thr Leu Phe Glu
305                 310                 315                 320

Asp Leu Ala Leu Val Arg Pro Thr Glu Leu Cys Phe Val Pro Arg Ile
                325                 330                 335

Trp Asp Met Val Phe Ala Glu Phe His Ser Glu Val Asp Arg Arg Leu
            340                 345                 350

Val Asp Gly Ala Asp Arg Ala Ala Leu Glu Ala Gln Val Lys Ala Glu
        355                 360                 365

Leu Arg Glu Asn Val Leu Gly Gly Arg Phe Val Met Ala Leu Thr Gly
370                 375                 380

Ser Ala Pro Ile Ser Ala Glu Met Thr Ala Trp Val Glu Ser Leu Leu
385                 390                 395                 400

Ala Asp Val His Leu Val Glu Gly Tyr Gly Ser Thr Glu Ala Gly Met
                405                 410                 415

Val Leu Asn Asp Gly Met Val Arg Arg Pro Ala Val Ile Asp Tyr Lys
            420                 425                 430

Leu Val Asp Val Pro Glu Leu Gly Tyr Phe Gly Thr Asp Gln Pro Tyr
        435                 440                 445

Pro Arg Gly Glu Leu Leu Val Lys Thr Gln Thr Met Phe Pro Gly Tyr
450                 455                 460

Tyr Gln Arg Pro Asp Val Thr Ala Glu Val Phe Asp Pro Asp Gly Phe
465                 470                 475                 480
```

-continued

Tyr Arg Thr Gly Asp Ile Met Ala Lys Val Gly Pro Asp Gln Phe Val
              485                 490                 495

Tyr Leu Asp Arg Arg Asn Asn Val Leu Lys Leu Ser Gln Gly Glu Phe
              500                 505                 510

Ile Ala Val Ser Lys Leu Glu Ala Val Phe Gly Asp Ser Pro Leu Val
              515                 520                 525

Arg Gln Ile Phe Ile Tyr Gly Asn Ser Ala Arg Ala Tyr Pro Leu Ala
              530                 535                 540

Val Val Val Pro Ser Gly Asp Ala Leu Ser Arg His Gly Ile Glu Asn
545                 550                 555                 560

Leu Lys Pro Val Ile Ser Glu Ser Leu Gln Glu Val Ala Arg Ala Ala
              565                 570                 575

Gly Leu Gln Ser Tyr Glu Ile Pro Arg Asp Phe Ile Ile Glu Thr Thr
              580                 585                 590

Pro Phe Thr Leu Glu Asn Gly Leu Leu Thr Gly Ile Arg Lys Leu Ala
              595                 600                 605

Arg Pro Gln Leu Lys Lys Phe Tyr Gly Glu Arg Leu Glu Arg Leu Tyr
              610                 615                 620

Thr Glu Leu Ala Asp Ser Gln Ser Asn Glu Leu Arg Glu Leu Arg Gln
625                 630                 635                 640

Ser Gly Pro Asp Ala Pro Val Leu Pro Thr Leu Cys Arg Ala Ala Ala
              645                 650                 655

Ala Leu Leu Gly Ser Thr Ala Ala Asp Val Arg Pro Asp Ala His Phe
              660                 665                 670

Ala Asp Leu Gly Gly Asp Ser Leu Ser Ala Leu Ser Leu Ala Asn Leu
              675                 680                 685

Leu His Glu Ile Phe Gly Val Asp Val Pro Val Gly Val Ile Val Ser
              690                 695                 700

Pro Ala Ser Asp Leu Arg Ala Leu Ala Asp His Ile Glu Ala Ala Arg
705                 710                 715                 720

Thr Gly Val Arg Arg Pro Ser Phe Ala Ser Ile His Gly Arg Ser Ala
              725                 730                 735

Thr Glu Val His Ala Ser Asp Leu Thr Leu Asp Lys Phe Ile Asp Ala
              740                 745                 750

Ala Thr Leu Ala Ala Ala Pro Asn Leu Pro Ala Pro Ser Ala Gln Val
              755                 760                 765

Arg Thr Val Leu Leu Thr Gly Ala Thr Gly Phe Leu Gly Arg Tyr Leu
              770                 775                 780

Ala Leu Glu Trp Leu Asp Arg Met Asp Leu Val Asn Gly Lys Leu Ile
785                 790                 795                 800

Cys Leu Val Arg Ala Arg Ser Asp Glu Glu Ala Gln Ala Arg Leu Asp
              805                 810                 815

Ala Thr Phe Asp Ser Gly Asp Pro Tyr Leu Val Arg His Tyr Arg Glu
              820                 825                 830

Leu Gly Ala Gly Arg Leu Glu Val Leu Ala Gly Asp Lys Gly Glu Ala
              835                 840                 845

Asp Leu Gly Leu Asp Arg Val Thr Trp Gln Arg Leu Ala Asp Thr Val
              850                 855                 860

Asp Leu Ile Val Asp Pro Ala Ala Leu Val Asn His Val Leu Pro Tyr
865                 870                 875                 880

Ser Gln Leu Phe Gly Pro Asn Ala Ala Gly Thr Ala Glu Leu Leu Arg
              885                 890                 895

Leu Ala Leu Thr Gly Lys Arg Lys Pro Tyr Ile Tyr Thr Ser Thr Ile

```
                        900             905             910
Ala Val Gly Glu Gln Ile Pro Pro Glu Ala Phe Thr Glu Asp Ala Asp
            915                 920                 925

Ile Arg Ala Ile Ser Pro Thr Arg Arg Ile Asp Asp Ser Tyr Ala Asn
    930                 935                 940

Gly Tyr Ala Asn Ser Lys Trp Ala Gly Glu Val Leu Leu Arg Glu Ala
945                 950                 955                 960

His Glu Gln Cys Gly Leu Pro Val Thr Val Phe Arg Cys Asp Met Ile
                965                 970                 975

Leu Ala Asp Thr Ser Tyr Thr Gly Gln Leu Asn Leu Pro Asp Met Phe
            980                 985                 990

Thr Arg Leu Met Leu Ser Leu Ala Ala Thr Gly Ile Ala Pro Gly Ser
        995                 1000                1005

Phe Tyr Glu Leu Asp Ala His Gly Asn Arg Gln Arg Ala His Tyr
    1010                1015                1020

Asp Gly Leu Pro Val Glu Phe Val Ala Glu Ala Ile Cys Thr Leu
    1025                1030                1035

Gly Thr His Ser Pro Asp Arg Phe Val Thr Tyr His Val Met Asn
    1040                1045                1050

Pro Tyr Asp Asp Gly Ile Gly Leu Asp Glu Phe Val Asp Trp Leu
    1055                1060                1065

Asn Ser Pro Thr Ser Gly Ser Gly Cys Thr Ile Gln Arg Ile Ala
    1070                1075                1080

Asp Tyr Gly Glu Trp Leu Gln Arg Phe Glu Thr Ser Leu Arg Ala
    1085                1090                1095

Leu Pro Asp Arg Gln Arg His Ala Ser Leu Leu Pro Leu Leu His
    1100                1105                1110

Asn Tyr Arg Glu Pro Ala Lys Pro Ile Cys Gly Ser Ile Ala Pro
    1115                1120                1125

Thr Asp Gln Phe Arg Ala Ala Val Gln Glu Ala Lys Ile Gly Pro
    1130                1135                1140

Asp Lys Asp Ile Pro His Leu Thr Ala Ala Ile Ile Ala Lys Tyr
    1145                1150                1155

Ile Ser Asn Leu Arg Leu Leu Gly Leu Leu
    1160                1165

<210> SEQ ID NO 33
<211> LENGTH: 1047
<212> TYPE: PRT
<213> ORGANISM: M. bovis BCG

<400> SEQUENCE: 33

Met Ser Ile Asn Asp Gln Arg Leu Thr Arg Arg Val Glu Asp Leu Tyr
1               5                   10                  15

Ala Ser Asp Ala Gln Phe Ala Ala Ala Ser Pro Asn Glu Ala Ile Thr
            20                  25                  30

Gln Ala Ile Asp Gln Pro Gly Val Ala Leu Pro Gln Leu Ile Ar

-continued

```
Thr Leu Ala Thr Ala Leu Ser Ala Glu Pro Ala Ile Arg Pro Gly Asp
            100                 105                 110
Arg Val Cys Val Leu Gly Phe Asn Ser Val Asp Tyr Thr Ile Asp
        115                 120                 125
Ile Ala Leu Ile Arg Leu Gly Ala Val Ser Val Pro Leu Gln Thr Ser
    130                 135                 140
Ala Pro Val Thr Gly Leu Arg Pro Ile Val Thr Glu Thr Glu Pro Thr
145                 150                 155                 160
Met Ile Ala Thr Ser Ile Asp Asn Leu Gly Asp Ala Val Glu Val Leu
                165                 170                 175
Ala Gly His Ala Pro Ala Arg Leu Val Val Phe Asp Tyr His Gly Lys
            180                 185                 190
Val Asp Thr His Arg Glu Ala Val Glu Ala Ala Arg Ala Arg Leu Ala
        195                 200                 205
Gly Ser Val Thr Ile Asp Thr Leu Ala Glu Leu Ile Glu Arg Gly Arg
    210                 215                 220
Ala Leu Pro Ala Thr Pro Ile Ala Asp Ser Ala Asp Asp Ala Leu Ala
225                 230                 235                 240
Leu Leu Ile Tyr Thr Ser Gly Ser Thr Gly Ala Pro Lys Gly Ala Met
                245                 250                 255
Tyr Arg Glu Ser Gln Val Met Ser Phe Trp Arg Lys Ser Ser Gly Trp
            260                 265                 270
Phe Glu Pro Ser Gly Tyr Pro Ser Ile Thr Leu Asn Phe Met Pro Met
        275                 280                 285
Ser His Val Gly Gly Arg Gln Val Leu Tyr Gly Thr Leu Ser Asn Gly
    290                 295                 300
Gly Thr Ala Tyr Tyr Val Ala Lys Ser Asp Leu Ser Thr Leu Phe Glu
305                 310                 315                 320
Asp Leu Ala Leu Val Arg Pro Thr Glu Leu Cys Phe Val Pro Arg Ile
                325                 330                 335
Trp Asp Met Val Phe Ala Glu Phe His Ser Glu Val Asp Arg Arg Leu
            340                 345                 350
Val Asp Gly Ala Asp Arg Ala Leu Glu Ala Gln Val Lys Ala Glu
        355                 360                 365
Leu Arg Glu Asn Val Leu Gly Gly Arg Phe Val Met Ala Leu Thr Gly
    370                 375                 380
Ser Ala Pro Ile Ser Ala Glu Met Thr Ala Trp Val Glu Ser Leu Leu
385                 390                 395                 400
Ala Asp Val His Leu Val Glu Gly Tyr Gly Ser Thr Glu Ala Gly Met
                405                 410                 415
Val Leu Asn Asp Gly Met Val Arg Arg Pro Ala Val Ile Asp Tyr Lys
            420                 425                 430
Leu Val Asp Val Pro Glu Leu Gly Tyr Phe Gly Thr Asp Gln Pro Tyr
        435                 440                 445
Pro Arg Gly Glu Leu Leu Val Lys Thr Gln Thr Met Phe Pro Gly Tyr
    450                 455                 460
Tyr Gln Arg Pro Asp Val Thr Ala Glu Val Phe Asp Pro Asp Gly Phe
465                 470                 475                 480
Tyr Arg Thr Gly Asp Ile Met Ala Lys Val Gly Pro Asp Gln Phe Val
                485                 490                 495
Tyr Leu Asp Arg Arg Asn Asn Val Leu Lys Leu Ser Gln Gly Glu Phe
            500                 505                 510
Ile Ala Val Ser Lys Leu Glu Ala Val Phe Gly Asp Ser Pro Leu Val
```

-continued

```
                515                 520                 525
Arg Gln Ile Phe Ile Tyr Gly Asn Ser Ala Arg Ala Tyr Pro Leu Ala
            530                 535                 540
Val Val Val Pro Ser Gly Asp Ala Leu Ser Arg His Gly Ile Glu Asn
545                 550                 555                 560
Leu Lys Pro Val Ile Ser Glu Ser Leu Gln Glu Val Ala Arg Ala Ala
                565                 570                 575
Gly Leu Gln Ser Tyr Glu Ile Pro Arg Asp Phe Ile Ile Glu Thr Thr
            580                 585                 590
Pro Phe Thr Leu Glu Asn Gly Leu Leu Thr Gly Ile Arg Lys Leu Ala
        595                 600                 605
Arg Pro Gln Leu Lys Lys Phe Tyr Gly Glu Arg Leu Glu Arg Leu Tyr
    610                 615                 620
Thr Glu Leu Ala Asp Ser Gln Ser Asn Glu Leu Arg Glu Leu Arg Gln
625                 630                 635                 640
Ser Gly Pro Asp Ala Pro Val Leu Pro Thr Leu Cys Arg Ala Ala Ala
                645                 650                 655
Ala Leu Leu Gly Ser Thr Ala Ala Asp Val Arg Pro Asp Ala His Phe
            660                 665                 670
Ala Asp Leu Gly Gly Asp Ser Leu Ser Ala Leu Ser Leu Ala Asn Leu
        675                 680                 685
Leu His Glu Ile Phe Gly Val Asp Val Pro Val Gly Val Ile Val Ser
    690                 695                 700
Pro Ala Ser Asp Leu Arg Ala Leu Ala Asp His Ile Glu Ala Ala Arg
705                 710                 715                 720
Thr Gly Val Arg Arg Pro Ser Phe Ala Ser Ile His Gly Arg Ser Ala
                725                 730                 735
Thr Glu Val His Ala Ser Asp Leu Thr Leu Asp Lys Phe Ile Asp Ala
            740                 745                 750
Ala Thr Leu Ala Ala Ala Pro Asn Leu Pro Ala Pro Ser Ala Gln Val
        755                 760                 765
Arg Thr Val Leu Leu Thr Gly Ala Thr Gly Phe Leu Gly Arg Tyr Leu
    770                 775                 780
Ala Leu Glu Trp Leu Asp Arg Met Asp Leu Val Asn Gly Lys Leu Ile
785                 790                 795                 800
Cys Leu Val Arg Ala Arg Ser Asp Glu Glu Ala Gln Ala Arg Leu Asp
                805                 810                 815
Ala Thr Phe Asp Ser Gly Asp Pro Tyr Leu Val Arg His Tyr Arg Glu
            820                 825                 830
Leu Gly Ala Gly Arg Leu Glu Val Leu Ala Gly Asp Lys Gly Glu Ala
        835                 840                 845
Asp Leu Gly Leu Asp Arg Val Thr Trp Gln Arg Leu Ala Asp Thr Val
    850                 855                 860
Asp Leu Ile Val Asp Pro Ala Ala Leu Val Asn His Val Leu Pro Tyr
865                 870                 875                 880
Ser Gln Leu Phe Gly Pro Asn Ala Ala Gly Thr Ala Glu Leu Leu Arg
                885                 890                 895
Leu Ala Leu Thr Gly Lys Arg Lys Pro Tyr Ile Tyr Thr Ser Thr Ile
            900                 905                 910
Ala Val Gly Glu Gln Ile Pro Pro Glu Ala Phe Thr Glu Asp Ala Asp
        915                 920                 925
Ile Arg Ala Ile Ser Pro Thr Arg Arg Ile Asp Asp Ser Tyr Ala Asn
    930                 935                 940
```

```
Gly Tyr Ala Asn Ser Lys Trp Ala Gly Glu Val Leu Arg Glu Ala
945                 950                 955                 960

His Glu Gln Cys Gly Leu Pro Val Thr Val Phe Arg Cys Asp Met Ile
                965                 970                 975

Leu Ala Asp Thr Ser Tyr Thr Gly Gln Leu Asn Leu Pro Asp Met Phe
            980                 985                 990

Thr Arg Leu Met Leu Ser Leu Ala  Ala Thr Gly Ile Ala  Pro Gly Ser
        995                 1000                1005

Phe Tyr  Glu Leu Asp Ala His  Gly Asn Arg Gln Arg  Ala His Tyr
    1010                1015                1020

Asp Gly  Leu Pro Val Glu Phe  Val Ala Glu Ala Ile  Cys Thr Leu
    1025                1030                1035

Gly Thr  His Ser Pro Asp Arg  Phe Val
    1040                1045

<210> SEQ ID NO 34
<211> LENGTH: 1174
<212> TYPE: PRT
<213> ORGANISM: M. leprae

<400> SEQUENCE: 34

Met Ser Thr Ile Thr Lys Gln Glu Lys Gln Leu Ala Arg Arg Val Asp
1               5                   10                  15

Asp Leu Thr Ala Asn Asp Pro Gln Phe Ala Ala Lys Pro Asp Pro
            20                  25                  30

Ala Val Ala Ala Ala Leu Ala Gln Pro Gly Leu Arg Leu Pro Gln Ile
        35                  40                  45

Ile Gln Thr Ala Leu Asp Gly Tyr Ala Glu Arg Pro Ala Leu Gly Gln
    50                  55                  60

Arg Val Ala Glu Phe Thr Lys Asp Pro Lys Thr Gly Arg Thr Ser Met
65                  70                  75                  80

Glu Leu Leu Pro Ser Phe Glu Thr Ile Thr Tyr Arg Gln Leu Gly Asp
                85                  90                  95

Arg Val Gly Ala Leu Ala Arg Ala Trp Arg His Asp Leu His Ala
            100                 105                 110

Gly Tyr Arg Val Cys Val Leu Gly Phe Asn Ser Val Asp Tyr Ala Ile
        115                 120                 125

Ile Asp Met Ala Leu Gly Val Ile Gly Ala Val Ala Val Pro Leu Gln
    130                 135                 140

Thr Ser Ala Ala Ile Thr Gln Leu Gln Ser Ile Val Thr Glu Thr Glu
145                 150                 155                 160

Pro Ser Met Ile Ala Thr Ser Val Asn Gln Leu Pro Asp Thr Val Glu
                165                 170                 175

Leu Ile Leu Ser Gly Gln Ala Pro Ala Lys Leu Val Val Phe Asp Tyr
            180                 185                 190

His Pro Glu Val Asp Glu Gln His Asp Ala Val Ala Thr Ala Arg Ala
        195                 200                 205

Arg Leu Ala Asp Ser Ser Val Val Glu Ser Leu Thr Glu Val Leu
    210                 215                 220

Gly Arg Gly Lys Thr Leu Pro Ala Thr Pro Ile Pro Val Ala Asp Asp
225                 230                 235                 240

Ser Ala Asp Pro Leu Ala Leu Leu Ile Tyr Thr Ser Gly Ser Thr Gly
                245                 250                 255

Ala Pro Lys Gly Ala Met Tyr Leu Gln Ser Asn Val Gly Lys Met Trp
```

```
            260               265                270
Arg Arg Ser Asp Gly Asn Trp Phe Gly Pro Thr Ala Ala Ser Ile Thr
        275                 280                285

Leu Asn Phe Met Pro Met Ser His Val Met Gly Arg Gly Ile Leu Tyr
    290                 295                 300

Gly Thr Leu Gly Asn Gly Gly Thr Ala Tyr Phe Ala Ala Arg Ser Asp
305                 310                 315                320

Leu Ser Thr Leu Leu Glu Asp Leu Lys Leu Val Arg Pro Thr Glu Leu
                325                 330                335

Asn Phe Val Pro Arg Ile Trp Glu Thr Leu Tyr Asp Glu Ser Lys Arg
            340                 345                350

Ala Val Asp Arg Arg Leu Ala Asn Ser Gly Ser Ala Asp Arg Ala Ala
            355                 360                365

Ile Lys Ala Glu Val Met Asp Glu Gln Arg Gln Ser Leu Leu Gly Gly
        370                 375                 380

Arg Tyr Ile Ala Ala Met Thr Gly Ser Ala Pro Thr Ser Pro Glu Leu
385                 390                 395                400

Lys His Gly Val Glu Ser Leu Leu Glu Met His Leu Leu Glu Gly Tyr
                405                 410                415

Gly Ser Thr Glu Ala Gly Met Val Leu Phe Asp Gly Glu Val Gln Arg
                420                 425                430

Pro Pro Val Ile Asp Tyr Lys Leu Val Asp Val Pro Asp Leu Gly Tyr
            435                 440                445

Phe Ser Thr Asp Gln Pro Tyr Pro Arg Gly Glu Leu Leu Leu Lys Thr
    450                 455                 460

Gln Asn Met Phe Pro Gly Tyr Tyr Lys Arg Pro Glu Val Thr Ala Thr
465                 470                 475                480

Val Phe Asp Ser Asp Gly Tyr Tyr Gln Thr Gly Asp Ile Val Ala Glu
                485                 490                495

Val Gly Pro Asp Arg Leu Val Tyr Val Asp Arg Arg Asn Asn Val Leu
                500                 505                510

Lys Leu Ala Gln Gly Gln Phe Val Thr Val Ala Lys Leu Glu Ala Ala
    515                 520                 525

Phe Ser Asn Ser Pro Leu Val Arg Gln Ile Tyr Ile Tyr Gly Asn Ser
530                 535                 540

Ala His Pro Tyr Leu Leu Ala Val Val Val Pro Thr Glu Asp Ala Leu
545                 550                 555                560

Ala Thr Asn Asp Ile Glu Val Leu Lys Pro Leu Ile Ile Asp Ser Leu
            565                 570                575

Gln Lys Val Ala Lys Glu Ala Asp Leu Gln Ser Tyr Glu Val Pro Arg
            580                 585                590

Asp Leu Ile Val Glu Thr Thr Pro Phe Ser Leu Glu Asn Gly Leu Leu
        595                 600                605

Thr Gly Ile Arg Lys Leu Ala Trp Pro Lys Leu Lys Gln His Tyr Gly
    610                 615                 620

Ala Arg Leu Glu Gln Leu Tyr Ala Asp Leu Val Glu Gly Gln Ala Asn
625                 630                 635                640

Ala Leu His Val Leu Lys Gln Ser Val Ala Asn Ala Pro Val Leu Gln
                645                 650                655

Thr Val Ser Arg Ala Val Gly Thr Ile Leu Gly Val Ala Thr Thr Asp
            660                 665                670

Leu Pro Ser Asn Ala His Phe Thr Asp Leu Gly Gly Asp Ser Leu Ser
            675                 680                685
```

-continued

```
Ala Leu Thr Phe Gly Ser Leu Leu Arg Glu Leu Phe Asp Ile Asp Val
    690                 695                 700
Pro Val Gly Val Ile Val Ser Pro Val Asn Asn Leu Val Ala Ile Ala
705                 710                 715                 720
Asp Tyr Ile Glu Arg Glu Arg Gln Gly Thr Lys Arg Pro Thr Phe Ile
                725                 730                 735
Ala Ile His Gly Arg Asp Ala Gly Lys Val His Ala Ser Asp Leu Thr
            740                 745                 750
Leu Asp Lys Phe Ile Asp Val Ser Thr Leu Thr Ala Ala Pro Val Leu
        755                 760                 765
Ala Gln Pro Gly Thr Glu Val Arg Thr Val Leu Leu Thr Gly Ala Thr
    770                 775                 780
Gly Phe Leu Gly Arg Tyr Leu Ala Leu Lys Trp Leu Glu Arg Met Asp
785                 790                 795                 800
Leu Val Glu Gly Lys Val Ile Ala Leu Val Arg Ala Lys Ser Asn Glu
                805                 810                 815
Asp Ala Arg Ala Arg Leu Asp Lys Thr Phe Asp Ser Gly Asp Pro Lys
            820                 825                 830
Leu Leu Ala His Tyr Gln Glu Leu Ala Thr Asp His Leu Glu Val Ile
        835                 840                 845
Ala Gly Asp Lys Gly Glu Val Asp Leu Glu Leu Asp Arg Gln Thr Trp
    850                 855                 860
Arg Arg Leu Ala Asp Thr Val Asp Leu Ile Val Asp Pro Ala Ala Leu
865                 870                 875                 880
Val Asn His Val Leu Pro Tyr Ser Glu Leu Phe Gly Pro Asn Thr Leu
                885                 890                 895
Gly Thr Ala Glu Leu Ile Arg Ile Ala Leu Thr Ser Lys Gln Lys Pro
            900                 905                 910
Tyr Ile Tyr Val Ser Thr Ile Gly Val Gly Asn Gln Ile Glu Pro Ala
        915                 920                 925
Lys Phe Thr Glu Asp Ser Asp Ile Arg Val Ile Ser Pro Thr Arg Asn
    930                 935                 940
Ile Asn Asn Asn Tyr Ala Asn Gly Tyr Gly Asn Ser Lys Trp Ala Gly
945                 950                 955                 960
Glu Val Leu Leu Arg Glu Ala His Asp Leu Cys Gly Leu Pro Val Thr
                965                 970                 975
Val Phe Arg Cys Asp Met Ile Leu Ala Asp Thr Ser Tyr Ala Gly Gln
            980                 985                 990
Leu Asn Val Pro Asp Met Phe Thr Arg Met Met Leu Ser Leu Ala Ala
        995                 1000                1005
Thr Gly Ile Ala Pro Gly Ser Phe Tyr Glu Leu Asp Ala Glu Ser
    1010                1015                1020
Asn Arg Gln Arg Ala His Tyr Asp Gly Leu Pro Val Glu Phe Ile
    1025                1030                1035
Ala Glu Ala Ile Ser Thr Leu Gly Asp Gln Ser Leu His Asp Arg
    1040                1045                1050
Asp Gly Phe Thr Thr Tyr His Val Met Asn Pro His Asp Asp Gly
    1055                1060                1065
Ile Gly Met Asp Glu Phe Val Asp Trp Leu Ile Asp Ala Gly Cys
    1070                1075                1080
Pro Ile Gln Arg Ile Asn Asp Tyr Asp Glu Trp Leu Arg Arg Phe
    1085                1090                1095
```

-continued

Glu Ile Ser Leu Arg Ala Leu Pro Glu Arg Gln Arg His Ser Ser
    1100            1105            1110

Leu Leu Pro Leu Leu His Asn Tyr Gln Lys Pro Glu Lys Pro Leu
    1115            1120            1125

His Gly Ser Leu Ala Pro Thr Ile Arg Phe Arg Thr Ala Val Gln
    1130            1135            1140

Asn Ala Asn Ile Gly Gln Asp Lys Asp Ile Pro His Ile Ser Pro
    1145            1150            1155

Ala Ile Ile Ala Lys Tyr Val Ser Asp Leu Gln Leu Leu Gly Leu
    1160            1165            1170

Val

<210> SEQ ID NO 35
<211> LENGTH: 1168
<212> TYPE: PRT
<213> ORGANISM: M. smegmatis MBCG

<400> SEQUENCE: 35

Met Thr Ile Glu Thr Arg Glu Asp Arg Phe Asn Arg Arg Ile Asp His
1               5                   10                  15

Leu Phe Glu Thr Asp Pro Gln Phe Ala Ala Arg Pro Asp Glu Ala
            20                  25                  30

Ile Ser Ala Ala Ala Asp Pro Glu Leu Arg Leu Pro Ala Ala Val
            35                  40                  45

Lys Gln Ile Leu Ala Gly Tyr Ala Asp Arg Pro Ala Leu Gly Lys Arg
50                  55                  60

Ala Val Glu Phe Val Thr Asp Glu Glu Gly Arg Thr Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
            115                 120                 125

Ile Ala Leu Leu Glu Leu Gly Ala Val Ser Val Pro Leu Gln Thr Ser
        130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
                165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
        195                 200                 205

Ala Gly Thr Gly Val Val Val Glu Thr Ile Thr Asp Ala Leu Asp Arg
    210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
        275                 280                 285

```
Leu Asn Phe Met Pro Met Ser His Val Met Gly Arg Gly Ile Leu Cys
    290                 295                 300
Ser Thr Leu Ala Ser Gly Gly Thr Ala Tyr Phe Ala Ala Arg Ser Asp
305                 310                 315                 320
Leu Ser Thr Phe Leu Glu Asp Leu Ala Leu Val Arg Pro Thr Gln Leu
                325                 330                 335
Asn Phe Val Pro Arg Ile Trp Asp Met Leu Phe Gln Glu Tyr Gln Ser
                340                 345                 350
Arg Leu Asp Asn Arg Arg Ala Glu Gly Ser Glu Asp Arg Ala Glu Ala
                355                 360                 365
Ala Val Leu Glu Glu Val Arg Thr Gln Leu Leu Gly Gly Arg Phe Val
    370                 375                 380
Ser Ala Leu Thr Gly Ser Ala Pro Ile Ser Ala Glu Met Lys Ser Trp
385                 390                 395                 400
Val Glu Asp Leu Leu Asp Met His Leu Leu Glu Gly Tyr Gly Ser Thr
                405                 410                 415
Glu Ala Gly Ala Val Phe Ile Asp Gly Gln Ile Gln Arg Pro Pro Val
                420                 425                 430
Ile Asp Tyr Lys Leu Val Asp Val Pro Asp Leu Gly Tyr Phe Ala Thr
            435                 440                 445
Asp Arg Pro Tyr Pro Arg Gly Glu Leu Leu Val Lys Ser Glu Gln Met
    450                 455                 460
Phe Pro Gly Tyr Tyr Lys Arg Pro Glu Ile Thr Ala Glu Met Phe Asp
465                 470                 475                 480
Glu Asp Gly Tyr Tyr Arg Thr Gly Asp Ile Val Ala Glu Leu Gly Pro
                485                 490                 495
Asp His Leu Glu Tyr Leu Asp Arg Arg Asn Asn Val Leu Lys Leu Ser
            500                 505                 510
Gln Gly Glu Phe Val Thr Val Ser Lys Leu Glu Ala Val Phe Gly Asp
    515                 520                 525
Ser Pro Leu Val Arg Gln Ile Tyr Val Tyr Gly Asn Ser Ala Arg Ser
530                 535                 540
Tyr Leu Leu Ala Val Val Pro Thr Glu Glu Ala Leu Ser Arg Trp
545                 550                 555                 560
Asp Gly Asp Glu Leu Lys Ser Arg Ile Ser Asp Ser Leu Gln Asp Ala
                565                 570                 575
Ala Arg Ala Ala Gly Leu Gln Ser Tyr Glu Ile Pro Arg Asp Phe Leu
                580                 585                 590
Val Glu Thr Thr Pro Phe Thr Leu Glu Asn Gly Leu Leu Thr Gly Ile
    595                 600                 605
Arg Lys Leu Ala Arg Pro Lys Leu Lys Ala His Tyr Gly Glu Arg Leu
    610                 615                 620
Glu Gln Leu Tyr Thr Asp Leu Ala Glu Gly Gln Ala Asn Glu Leu Arg
625                 630                 635                 640
Glu Leu Arg Arg Asn Gly Ala Asp Arg Pro Val Val Glu Thr Val Ser
                645                 650                 655
Arg Ala Ala Val Ala Leu Leu Gly Ala Ser Val Thr Asp Leu Arg Ser
                660                 665                 670
Asp Ala His Phe Thr Asp Leu Gly Gly Asp Ser Leu Ser Ala Leu Ser
            675                 680                 685
Phe Ser Asn Leu Leu His Glu Ile Phe Asp Val Asp Val Pro Val Gly
    690                 695                 700
Val Ile Val Ser Pro Ala Thr Asp Leu Ala Gly Val Ala Ala Tyr Ile
```

-continued

```
            705                 710                 715                 720
Glu Gly Glu Leu Arg Gly Ser Lys Arg Pro Thr Tyr Ala Ser Val His
                    725                 730                 735
Gly Arg Asp Ala Thr Glu Val Arg Ala Arg Asp Leu Ala Leu Gly Lys
                    740                 745                 750
Phe Ile Asp Ala Lys Thr Leu Ser Ala Ala Pro Gly Leu Pro Arg Ser
                    755                 760                 765
Gly Thr Glu Ile Arg Thr Val Leu Leu Thr Gly Ala Thr Gly Phe Leu
            770                 775                 780
Gly Arg Tyr Leu Ala Leu Glu Trp Leu Glu Arg Met Asp Leu Val Asp
785                 790                 795                 800
Gly Lys Val Ile Cys Leu Val Arg Ala Arg Ser Asp Asp Glu Ala Arg
                    805                 810                 815
Ala Arg Leu Asp Ala Thr Phe Asp Thr Gly Asp Ala Thr Leu Leu Glu
                    820                 825                 830
His Tyr Arg Ala Leu Ala Ala Asp His Leu Glu Val Ile Ala Gly Asp
                    835                 840                 845
Lys Gly Glu Ala Asp Leu Gly Leu Asp His Asp Thr Trp Gln Arg Leu
            850                 855                 860
Ala Asp Thr Val Asp Leu Ile Val Asp Pro Ala Ala Leu Val Asn His
865                 870                 875                 880
Val Leu Pro Tyr Ser Gln Met Phe Gly Pro Asn Ala Leu Gly Thr Ala
                    885                 890                 895
Glu Leu Ile Arg Ile Ala Leu Thr Thr Thr Ile Lys Pro Tyr Val Tyr
                    900                 905                 910
Val Ser Thr Ile Gly Val Gly Gln Gly Ile Ser Pro Glu Ala Phe Val
                    915                 920                 925
Glu Asp Ala Asp Ile Arg Glu Ile Ser Ala Thr Arg Arg Val Asp Asp
            930                 935                 940
Ser Tyr Ala Asn Gly Tyr Gly Asn Ser Lys Trp Ala Gly Glu Val Leu
945                 950                 955                 960
Leu Arg Glu Ala His Asp Trp Cys Gly Leu Pro Val Ser Val Phe Arg
                    965                 970                 975
Cys Asp Met Ile Leu Ala Asp Thr Thr Tyr Ser Gly Gln Leu Asn Leu
                    980                 985                 990
Pro Asp Met Phe Thr Arg Leu Met Leu Ser Leu Val Ala Thr Gly Ile
                    995                1000                1005
Ala Pro Gly Ser Phe Tyr Glu Leu Asp Ala Asp Gly Asn Arg Gln
            1010                1015                1020
Arg Ala His Tyr Asp Gly Leu Pro Val Glu Phe Ile Ala Glu Ala
            1025                1030                1035
Ile Ser Thr Ile Gly Ser Gln Val Thr Asp Gly Phe Glu Thr Phe
            1040                1045                1050
His Val Met Asn Pro Tyr Asp Asp Gly Ile Gly Leu Asp Glu Tyr
            1055                1060                1065
Val Asp Trp Leu Ile Glu Ala Gly Tyr Pro Val His Arg Val Asp
            1070                1075                1080
Asp Tyr Ala Thr Trp Leu Ser Arg Phe Glu Thr Ala Leu Arg Ala
            1085                1090                1095
Leu Pro Glu Arg Gln Arg Gln Ala Ser Leu Leu Pro Leu Leu His
            1100                1105                1110
Asn Tyr Gln Gln Pro Ser Pro Pro Val Cys Gly Ala Met Ala Pro
            1115                1120                1125
```

```
Thr Asp Arg Phe Arg Ala Ala Val Gln Asp Ala Lys Ile Gly Pro
    1130                1135                1140

Asp Lys Asp Ile Pro His Val Thr Ala Asp Val Ile Val Lys Tyr
    1145                1150                1155

Ile Ser Asn Leu Gln Met Leu Gly Leu Leu
    1160                1165

<210> SEQ ID NO 36
<211> LENGTH: 869
<212> TYPE: PRT
<213> ORGANISM: hypothetical

<400> SEQUENCE: 36

Val Asp Arg Leu Arg Arg Ile Glu Leu Phe Ala Asp Gln Phe Ala Ala
1               5                   10                  15

Ala Pro Glu Ala Val Ser Ala Val Pro Gly Met Leu Pro Gln Ile Ile
            20                  25                  30

Val Met Gly Tyr Ala Asp Arg Pro Ala Leu Gly Gln Arg Ala Phe Thr
        35                  40                  45

Asp Thr Gly Arg Leu Leu Gly Phe Ser Val Asp Tyr Thr Ile Asp Leu
    50                  55                  60

Ala Leu Ile Leu Gly Ala Val Thr Val Pro Leu Gln Thr Ser Ala Val
65                  70                  75                  80

Ser Leu Ile Val Thr Glu Thr Glu Pro Leu Ile Ala Ser Ser Ile Glu
                85                  90                  95

Leu Asp Ala Val Glu Val Leu Ala Pro Arg Leu Val Val Phe Asp Tyr
            100                 105                 110

His Val Asp Arg Glu Ala Glu Ala Arg Ala Arg Leu Ala Ser Val Val
        115                 120                 125

Glu Thr Leu Glu Val Ile Arg Gly Arg Leu Pro Ala Val Asp Asp Leu
    130                 135                 140

Ala Leu Leu Ile Tyr Thr Ser Gly Ser Thr Gly Pro Lys Gly Ala Met
145                 150                 155                 160

Tyr Ser Thr Trp Ser Ile Thr Leu Asn Phe Met Pro Met Ser His Val
                165                 170                 175

Gly Arg Val Leu Phe Gly Thr Leu Gly Gly Thr Ala Tyr Phe Ala Lys
            180                 185                 190

Ser Asp Leu Ser Thr Leu Glu Asp Leu Gly Leu Val Arg Pro Thr Glu
        195                 200                 205

Leu Phe Val Pro Arg Ile Trp Asp Met Val Phe Glu Tyr Ser Leu Asp
    210                 215                 220

Arg Arg Gly Ala Asp Leu Asp Ala Val Glu Leu Arg Asn Val Leu Gly
225                 230                 235                 240

Gly Arg Phe Leu Ala Val Thr Gly Ser Ala Pro Leu Ser Ala Glu Met
                245                 250                 255

Phe Val Glu Ser Leu Asp Leu His Leu Val Glu Gly Tyr Gly Ser Thr
            260                 265                 270

Glu Ala Gly Val Leu Asp Gly Ile Arg Pro Val Ile Asp Tyr Lys Leu
        275                 280                 285

Val Asp Val Pro Glu Leu Gly Tyr Phe Thr Asp Pro Tyr Pro Arg Gly
    290                 295                 300

Glu Leu Leu Leu Lys Thr Met Phe Pro Gly Tyr Tyr Arg Pro Glu Val
305                 310                 315                 320

Thr Ala Glu Ile Phe Asp Asp Gly Phe Tyr Lys Thr Gly Asp Ile Val
```

-continued

```
                325                 330                 335
Ala Leu Gly Pro Asp Val Tyr Val Asp Arg Arg Asn Asn Val Leu Lys
            340                 345                 350

Leu Ser Gln Gly Glu Phe Val Val Lys Leu Glu Ala Val Phe Ala Ser
            355                 360                 365

Pro Leu Val Arg Gln Ile Phe Ile Tyr Gly Asn Ser Ala Arg Tyr Leu
            370                 375                 380

Ala Val Val Val Pro Thr Asp Ala Leu Glu Leu Lys Ile Glu Ser Leu
385                 390                 395                 400

Gln Ile Ala Lys Ala Leu Gln Ser Tyr Glu Ile Pro Arg Asp Phe Leu
            405                 410                 415

Ile Glu Thr Thr Pro Phe Thr Leu Glu Asn Gly Leu Leu Thr Gly Ile
            420                 425                 430

Arg Lys Leu Ala Arg Pro Leu Lys Tyr Gly Arg Leu Glu Leu Tyr Thr
            435                 440                 445

Asp Leu Ala Asp Gln Asn Glu Leu Arg Leu Arg Ala Asp Pro Val Leu
            450                 455                 460

Thr Val Arg Ala Ala Ala Met Leu Gly Asp Met Arg Asp Ala His Phe
465                 470                 475                 480

Asp Leu Gly Gly Asp Ser Leu Ser Ala Leu Ser Asn Leu Leu His Glu
            485                 490                 495

Ile Phe Val Asp Val Pro Val Gly Val Ile Val Ser Pro Ala Glu Leu
            500                 505                 510

Ala Leu Ala Ile Glu Ala Arg Gly Lys Arg Pro Thr Phe Ser Val His
            515                 520                 525

Gly Arg Ala Ser Glu Val Arg Ala Asp Leu Thr Leu Asp Lys Phe Ile
            530                 535                 540

Asp Ala Thr Leu Ala Ala Pro Leu Pro Val Arg Thr Val Leu Leu Thr
545                 550                 555                 560

Gly Ala Thr Gly Phe Leu Gly Arg Tyr Leu Ala Leu Glu Trp Leu Glu
            565                 570                 575

Arg Met Asp Leu Val Gly Lys Leu Ile Cys Leu Val Arg Ala Arg Ser
            580                 585                 590

Glu Glu Ala Ala Arg Leu Asp Thr Phe Asp Ser Gly Asp Pro Leu Leu
            595                 600                 605

His Tyr Leu Ala Ala Arg Leu Glu Val Leu Ala Gly Asp Lys Gly Glu
            610                 615                 620

Asp Leu Gly Leu Asp Arg Thr Trp Gln Arg Leu Ala Asp Thr Val Asp
625                 630                 635                 640

Leu Ile Val Asp Pro Ala Ala Leu Val Asn His Val Leu Pro Tyr Ser
            645                 650                 655

Gln Leu Phe Gly Pro Asn Gly Thr Ala Glu Leu Val Arg Leu Ala Leu
            660                 665                 670

Thr Arg Lys Pro Tyr Ile Tyr Ser Thr Ile Gly Val Gly Gln Ile Pro
            675                 680                 685

Phe Glu Asp Asp Ile Arg Ile Ser Thr Arg Val Glu Ser Tyr Ala Asn
            690                 695                 700

Gly Tyr Gly Asn Ser Lys Trp Ala Gly Glu Val Leu Leu Arg Glu Ala
705                 710                 715                 720

His Asp Cys Gly Leu Pro Val Thr Val Phe Arg Cys Asp Met Ile Leu
            725                 730                 735

Ala Asp Thr Ser Tyr Gly Gln Leu Asn Val Pro Asp Met Phe Thr Arg
            740                 745                 750
```

Leu Met Leu Ser Leu Ala Thr Gly Ile Ala Pro Gly Ser Phe Tyr Glu
        755                 760                 765

Leu Asp Ala Gly Asn Arg Gln Arg Ala His Tyr Asp Gly Leu Pro Val
        770                 775                 780

Glu Phe Val Ala Glu Ala Ile Thr Leu Gly Asp Phe Thr Tyr Val Leu
785                 790                 795                 800

Asn Pro Asp Asp Gly Ile Leu Asp Glu Phe Val Asp Trp Leu Ile Arg
                805                 810                 815

Ile Asp Tyr Trp Arg Phe Glu Ile Arg Ala Leu Pro Glu Lys Gln Arg
                820                 825                 830

Ser Val Leu Pro Leu Leu Tyr Pro Val Gly Ile Pro Phe Ala Val Gln
        835                 840                 845

Ala Ile Gly Glu Asp Ile Pro His Leu Ser Leu Ile Lys Tyr Val Ser
850                 855                 860

Leu Leu Leu Leu Leu
865

<210> SEQ ID NO 37
<211> LENGTH: 4600
<212> TYPE: DNA
<213> ORGANISM: Nocardia

<400> SEQUENCE: 37

| | | | | | |
|---|---|---|---|---|---|
| ggtaccggca | atacctggat | aagcggtcgg | atcctgggcc | gctgcggtgg | agtggccgcc | 60 |
| gttccggccc | gatgtggcca | agaccactcg | agtcaccgcc | gcgtatcacc | ttcccggaag | 120 |
| tatttactta | ggctaacgtg | ttttacgggt | tgcagggctt | ttcctactta | tgacaaggga | 180 |
| ggcttgccat | ggcggtggat | tcaccggatg | agcggctaca | gcgccgcatt | gcgcagttgt | 240 |
| ttgcagaaga | tgagcaggtc | aaggccgcac | gtccgctcga | agcggtgagc | gcggcggtga | 300 |
| gcgcgcccgg | tatgcggctg | gcgcagatcg | ccgccactgt | tatggcgggt | tacgccgacc | 360 |
| gcccggccgc | cgggcagcgt | gcgttcgaac | tgaacaccga | cgacgcgacg | ggccgcacct | 420 |
| cgctgcggtt | acttccccga | ttcgagacca | tcacctatcg | cgaactgtgg | cagcgagtcg | 480 |
| gcgaggttgc | cgcggcctgg | catcatgatc | ccgagaaccc | cttgcgcgca | ggtgatttcg | 540 |
| tcgccctgct | cggcttcacc | agcatcgact | acgccaccct | cgacctggcc | gatatccacc | 600 |
| tcggcgcggt | taccgtgccg | ttgcaggcca | gcgcggcggt | gtcccagctg | atcgctatcc | 660 |
| tcaccgagac | ttcgccgcgg | ctgctcgcct | cgaccccgga | gcacctcgat | gcggcggtcg | 720 |
| agtgcctact | cgcgggcacc | acaccggaac | gactggtggt | cttcgactac | cacccgagg | 780 |
| acgacgacca | gcgtgcggcc | ttcgaatccg | cccgccgccg | ccttgccgac | gcgggcagct | 840 |
| cggtgatcgt | cgaaacgctc | gatgccgtgc | gtgcccgggg | ccgcgactta | ccggccgcgc | 900 |
| cactgttcgt | tcccgacacc | gacgacgacc | cgctggccct | gctgatctac | acctccggca | 960 |
| gcaccggaac | gccgaagggc | gcgatgtaca | ccaatcggtt | ggccgccacg | atgtggcagg | 1020 |
| ggaactcgat | gctgcagggg | aactcgcaac | gggtcgggat | caatctcaac | tacatgccga | 1080 |
| tgagccacat | cgccggtcgc | atatcgctgt | tcggcgtgct | cgctcgcggt | ggcaccgcat | 1140 |
| acttcgcggc | caagagcgac | atgtcgacac | tgttcgaaga | catcggcttg | gtacgtccca | 1200 |
| ccgagatctt | cttcgtcccg | cgcgtgtgcg | acatggtctt | ccagcgctat | cagagcgagc | 1260 |
| tggaccggcg | ctcggtggcg | ggcgccgacc | tggacacgct | cgatcgggaa | gtgaaagccg | 1320 |
| acctccggca | gaactacctc | ggtgggcgct | tcctggtggc | ggtcgtcggc | agcgcgccgc | 1380 |

```
tggccgcgga gatgaagacg ttcatggagt ccgtcctcga tctgccactg cacgacgggt   1440
acgggtcgac cgaggcgggc gcaagcgtgc tgctcgacaa ccagatccag cggccgccgg   1500
tgctcgatta caagctcgtc gacgtgcccg aactgggtta cttccgcacc gaccggccgc   1560
atccgcgcgg tgagctgttg ttgaaggcgg agaccacgat tccgggctac tacaagcggc   1620
ccgaggtcac cgcggagatc ttcgacgagg acggcttcta caagaccggc gatatcgtgg   1680
ccgagctcga gcacgatcgg ctggtctatg tcgaccgtcg caacaatgtg ctcaaactgt   1740 cgcaggcga gttcgtgacc gtcgcccatc tcgaggccgt gttcgccagc agcccgctga   1800
tccggcagat cttcatctac ggcagcagcg aacgttccta tctgctcgcg gtgatcgtcc   1860
ccaccgacga cgcgctgcgc ggccgcgaca ccgccacctt gaaatcggca ctggccgaat   1920
cgattcagcg catcgccaag gacgcgaacc tgcagcccta cgagattccg cgcgatttcc   1980
tgatcgagac cgagccgttc accatcgcca acggactgct ctccggcatc gcgaagctgc   2040
tgcgccccaa tctgaaggaa cgctacggcg ctcagctgga gcagatgtac accgatctcg   2100
cgacaggcca ggccgatgag ctgctcgccc tgcgccgcga agccgccgac ctgccggtgc   2160
tcgaaaccgt cagccgggca gcgaaagcga tgctcggcgt cgcctccgcc gatatgcgtc   2220
ccgacgcgca cttcaccgac ctgggcggcg attccctttc gcgctgtcg ttctcgaacc   2280 tgctgcacga gatcttcggg gtcgaggtgc cggtgggtgt cgtcgtcagc ccggcgaacg   2340
agctgcgcga tctggcgaat tacattgagg cggaacgcaa ctcgggcgcg aagcgtccca   2400
ccttcacctc ggtgcacggc ggcggttccg agatccgcgc cgccgatctg accctcgaca   2460
agttcatcga tgcccgcacc ctggccgccg ccgacagcat tccgcacgcg ccggtgccag   2520
cgcagacggt gctgctgacc ggcgcgaacg gctacctcgg ccggttcctg tgcctggaat   2580
ggctggagcg gctggacaag acgggtggca cgctgatctg cgtcgtgcgc ggtagtgacg   2640
cggccgcggc ccgtaaacgg ctggactcgg cgttcgacag cggcgatccc ggcctgctcg   2700
agcactacca gcaactggcc gcacggaccc tggaagtcct cgccggtgat atcggcgacc   2760
cgaatctcgg tctggacgac gcgacttggc agcggttggc cgaaaccgtc gacctgatcg   2820
tccatcccgc cgcgttggtc aaccacgtcc ttccctacac ccagctgttc ggccccaatg   2880
tcgtcggcac cgccgaaatc gtccggttgg cgatcacggc gcggcgcaag ccggtcacct   2940
acctgtcgac cgtcggagtg gccgaccagg tcgacccggc ggagtatcag gaggacagcg   3000
acgtccgcga gatgagcgcg gtgcgcgtcg tgcgcgagag ttacgccaac ggctacggca   3060
acagcaagtg ggcgggggag gtcctgctgc gcgaagcaca cgatctgtgt ggcttgccgg   3120
tcgcggtgtt ccgttcggac atgatcctgg cgcacagccg gtacgcgggt cagctcaacg   3180
tccaggacgt gttcacccgg ctgatcctca gcctggtcgc caccggcatc gcgccgtact   3240
cgttctaccg aaccgacgcg gacggcaacc ggcagcgggc ccactacgac ggtctgcccg   3300
ccgatttcac ggcggcggcg atcaccgcgc tcggcatcca agccaccgaa ggcttccgga   3360
cctacgacgt gctcaatccg tacgacgatg catctccct cgatgaattc gtcgactggc   3420
tcgtcgaatc cggccacccg atccagcgca tcaccgacta cagcgactgg ttccaccgtt   3480
tcgagacggc gatccgcgcg ctgccggaaa agcaacgcca ggcctcggtg ctgccgttgc   3540
tggacgccta ccgcaaccc tgcccggcgg tccgcggcgc gatactcccg gccaaggagt   3600
tccaagcggg ggtgcaaaca gccaaaatcg gtccggaaca ggacatcccg catttgtccg   3660
cgccactgat cgataagtac gtcagcgatc tggaactgct tcagctgctc tgacggatat   3720
caggccgccg cgcgcaccct cgtcggtgcgt tcggcgcctt cgcgccggag gcgaaacagg   3780
```

-continued

```
aataccgccg agccacccag gacagcggcg tagacgatga cgaagctgtt gatcaggacc    3840
tgggcgaccg gccaccacgg cgggaacagg aacagcccga cgacaacgta gtccgggctg    3900
tattcccacg tccacgcgcc gatcgagacg aagagcgcgg ccgaggcaag ccaccaccac    3960
ggctgcgact gcgccctgtg cagtagatag acgaacaggg gaacgaacca cacccagtgg    4020
tggtcccaga gaacggcga gaccgcgcag gcggtgaggc cggcgagggt gaccgcgagg    4080
agctgttcgc cacgccgata caggccgatg gtgacggcca gactcgccag cgcgacggag    4140
cccgcgatga gcagccacag ccacaccggc gccgggtgat gggtcaggtg cgcgatggcg    4200
ccgcggatgg attgattgga cgggtgcata tcgtccgcga tccgattgga ctggaagaac    4260
gtcgaggtcc agtactgccg ggaatcggcg ggcagcacga tccaggcgag gacgatggac    4320
gcgatgaaca ccgccacggc ggtgcacgcg gaccgccact gccgcaacgc gaggaattgc    4380
acgacgaagt agccagggac gagcttgatg cccgccgcca ccccgacgcc gaggccgcgc    4440
agcttgctgc ggtcgggccg ggagaagtcc cacagcacca gcagcatcag catcaggttg    4500
atctggccgt agaacagcgt tgtccggacg ggctcgatga acgcgcaggt gagcgccagt    4560
agggcgctga cgacggccag tctggcgttg atccggtacc                         4600
```

<210> SEQ ID NO 38
<211> LENGTH: 4600
<212> TYPE: DNA
<213> ORGANISM: Nocardia

<400> SEQUENCE: 38

```
ggtaccggca ataactggat aagcggtcgg atcctgggcc gctgcggtgg agtggccgcc      60
gttccggccc gatgtggcca agaccactcg agtcaccgcc gcgtatcacc ttcccggaag    120
tatttactta ggctaacgtg tttttacgggt tgcagggctt ttcctactta tgacaaggga    180
ggcttgccat ggcagtggat agtccggatg agcggctaca gcgccgcatt gcacagttgt    240
ttgcagaaga tgagcaggtc aaggccgcac gtccgctcga agcggtgagc gcggcggtga    300
gcgcgcccgg tatgcggctg gcgcagatcg ccgccactgt tatggcgggt tacgccgacc    360
gcccggccgc cgggcagcgt gcgttcgaac tgaacaccga cgacgcgacg ggccgcacct    420
cgctgcggtt acttccccga ttcgagacca tcacctatcg cgaactgtgg cagcgagtcg    480
gcgaggttgc cgcggcctgg catcatgatc ccgagaaccc cttgcgcgca ggtgatttcg    540
tcgccctgct cggcttcacc agcatcgact acgccaccct cgacctggcc gatatccacc    600
tcggcgcggt taccgtgccg ttgcaggcca gcgcggcggt gtcccagctg atcgctatcc    660
tcaccgagac ttcgccgcgg ctgctcgcct cgacccgga gcacctcgat gcggcggtcg    720
agtgcctact cgcgggcacc acaccggaac gactggtggt cttcgactac caccccgagg    780
acgacgacca gcgtgcggcc ttcgaatccg cccgccgccg ccttgccgac gcgggcagct    840
cggtgatcgt cgaaacgctc gatgccgtgc gtgcccgggg ccgcgactta ccggccgcgc    900
cactgttcgt tcccgacacc gacgacgacc cgctggccct gctgatctac acctccggca    960
gcaccggaac gccgaagggc gcgatgtaca ccaatcggtt ggccgccacg atgtggcagg    1020
ggaactcgat gctgcagggg aactcgcaac gggtcgggat caatctcaac tacatgccga    1080
tgagccacat cgccggtcgc atatcgctgt tcggcgtgct cgctcgcggt ggcaccgcat    1140
acttcgcggc caagagcgac atgtcgacac tgttcgaaga catcggcttg gtacgtccca    1200
ccgagatctt cttcgtcccg cgcgtgtgcg acatggtctt ccagcgctat cagagcgagc    1260
```

```
tggaccggcg ctcggtggcg ggcgccgacc tggacacgct cgatcgggaa gtgaaagccg    1320
acctccggca gaactacctc ggtgggcgct tcctggtggc ggtcgtcggc agcgcgccgc    1380
tggccgcgga gatgaagacg ttcatggagt ccgtcctcga tctgccactg cacgacgggt    1440
acgggtcgac cgaggcgggc gcaagcgtgc tgctcgacaa ccagatccag cggccgccgg    1500
tgctcgatta caagctcgtc gacgtgcccg aactgggtta cttccgcacc gaccggccgc    1560
atccgcgcgg tgagctgttg ttgaaggcgg agaccacgat tccgggctac tacaagcggc    1620
ccgaggtcac cgcggagatc ttcgacgagg acggcttcta caagaccggc gatatcgtgg    1680
ccgagctcga gcacgatcgg ctggtctatg tcgaccgtcg caacaatgtg ctcaaactgt    1740
cgcagggcga gttcgtgacc gtcgcccatc tcgaggccgt gttcgccagc agcccgctga    1800
tccggcagat cttcatctac ggcagcagcg aacgttccta tctgctcgcg gtgatcgtcc    1860
ccaccgacga cgcgctgcgc ggccgcgaca ccgccacctt gaaatcggca ctggccgaat    1920
cgattcagcg catcgccaag gacgcgaacc tgcagcccta cgagattccg cgcgatttcc    1980
tgatcgagac cgagccgttc accatcgcca acggactgct ctccggcatc gcgaagctgc    2040
tgcgccccaa tctgaaggaa cgctacggcg ctcagctgga gcagatgtac accgatctcg    2100
cgacaggcca ggccgatgag ctgctcgccc tgcgccgcga agccgccgac ctgccggtgc    2160
tcgaaaccgt cagccgggca gcgaaagcga tgctcggcgt cgcctccgcc gatatgcgtc    2220
ccgacgcgca cttcaccgac ctgggcggcg attccctttc cgcgctgtcg ttctcgaacc    2280
tgctgcacga gatcttcggg gtcgaggtgc cggtgggtgt cgtcgtcagc ccggcgaacg    2340
agctgcgcga tctggcgaat tacattgagg cggaacgcaa ctcgggcgcg aagcgtccca    2400
ccttcacctc ggtgcacggc ggcggttccg agatccgcgc cgccgatctg accctcgaca    2460
agttcatcga tgcccgcacc ctggccgccg ccgacagcat tccgcacgcg ccggtgccag    2520
cgcagacggt gctgctgacc ggcgcgaacg gctacctcgg ccggttcctg tgcctggaat    2580
ggctggagcg gctggacaag acgggtggca cgctgatctg cgtcgtgcgc ggtagtgacg    2640
cggccgcggc ccgtaaacgg ctggactcgg cgttcgacag cggcgatccc ggcctgctcg    2700
agcactacca gcaactggcc gcacggaccc tggaagtcct cgccggtgat atcggcgacc    2760
cgaatctcgg tctggacgac gcgacttggc agcggttggc cgaaaccgtc gacctgatcg    2820
tccatcccgc cgcgttggtc aaccacgtcc ttccctacac ccagctgttc ggccccaatg    2880
tcgtcggcac cgccgaaatc gtccggttgg cgatcacggc gcggcgcaag ccggtcacct    2940
acctgtcgac cgtcggagtg gccgaccagg tcgacccggc ggagtatcag gaggacagcg    3000
acgtccgcga gatgagcgcg gtgcgcgtcg tgcgcgagag ttacgccaac ggctacggca    3060
acagcaagtg ggcgggggag gtcctgctgc gcgaagcaca cgatctgtgt ggcttgccgg    3120
tcgcggtgtt ccgttcggac atgatcctgg cgcacagccg gtacgcgggt cagctcaacg    3180
tccaggacgt gttcacccgg ctgatcctca gcctggtcgc caccggcatc gcgccgtact    3240
cgttctaccg aaccgacgcg gacggcaacc ggcagcgggc ccactacgac ggtctgcccg    3300
ccgatttcac ggcggcggcg atcaccgcgc tcggcatcca agccaccgaa ggcttccgga    3360
cctacgacgt gctcaatccg tacgacgatg gcatctccct cgatgaattc gtcgactggc    3420
tcgtcgaatc cggccacccg atccagcgca tcaccgacta cagcgactgg ttccaccgtt    3480
tcgagacggt gatccgcgcg ctgccggaaa agcaacgcca ggcctcggtg ctgccgttgc    3540
tggacgccta ccgcaacccc tgcccggcgg tccgcggcgc gatactcccg gccaaggagt    3600
tccaagcggc ggtgcaaaca gccaaaatcg gtccggaaca ggacatcccg catttgtccg    3660
```

-continued

```
cgccactgat cgataagtac gtcagcgatc tggaactgct tcagctgctc tgacggatat    3720
caggccgccg cgcgcaccctc gtcggtgcgt tcggcgcctt cgcgccggag gcgaaacagg    3780
aataccgccg agcccaccag gacagcggcg tagacgatga cgaagctgtt gatcaggacc    3840
tgggcgaccg gccaccacgg cgggaacagg aacagcccga cgacaacgta gtccgggctg    3900
tattcccacg tccacgcgcc gatcgagacg aagagcgcgg ccgaggcaag ccaccaccac    3960
ggctgcgact gcgccctgtg cagtagatag acgaacaggg gaacgaacca cacccagtgg    4020
tggtcccagg agaacggcga gaccgcgcag gcggtgaggc cggcgagggt gaccgcgagg    4080
agctgttcgc cacgccgata caggccgatg gtgacggcca gactcgccag cgcgacggag    4140
cccgcgatga gcagccacag ccacaccggc gccgggtgat gggtcaggtg cgcgatggcg    4200
ccgcggatgg attgattgga cgggtgcata tcgtccgcga tccgattgga ctggaagaac    4260
gtcgaggtcc agtactgccg ggaatcggcg ggcagcacga tccaggcgag gacgatggac    4320
gcgatgaaca ccgccacggc ggtgcacgcg gaccgccact gccgcaacgc gaggaattgc    4380
acgacgaagt agccagggac gagcttgatg cccgccgcca ccccgacgcc gaggccgcgc    4440
agcttgctgc ggtcgggccg ggagaagtcc cacagcacca gcagcatcag catcaggttg    4500
atctggccgt agaacagcgt tgtccggacg ggctcgatga acgcgcaggt gagcgccagt    4560
agggcgctga cgacggccag tctggcgttg atccggtacc                          4600
```

<210> SEQ ID NO 39
<211> LENGTH: 1174
<212> TYPE: PRT
<213> ORGANISM: Nocardia

<400> SEQUENCE: 39

```
Met Ala Val Asp Ala Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
                20                  25                  30

Val Ser Ala Ala Val Ser Ala Pro Gly Met Arg Leu Ala Gln Ile Ala
            35                  40                  45

Ala Thr Val Met Ala Gly Tyr Ala Asp Arg Pro Ala Ala Gly Gln Arg
        50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205
```

```
Arg Arg Arg Leu Ala Asp Ala Gly Ser Ser Val Ile Val Glu Thr Leu
    210                 215                 220
Asp Ala Val Arg Ala Arg Gly Arg Asp Leu Pro Ala Ala Pro Leu Phe
225                 230                 235                 240
Val Pro Asp Thr Asp Asp Pro Leu Ala Leu Leu Ile Tyr Thr Ser
                245                 250                 255
Gly Ser Thr Gly Thr Pro Lys Gly Ala Met Tyr Thr Asn Arg Leu Ala
                260                 265                 270
Ala Thr Met Trp Gln Gly Asn Ser Met Leu Gln Gly Asn Ser Gln Arg
            275                 280                 285
Val Gly Ile Asn Leu Asn Tyr Met Pro Met Ser His Ile Ala Gly Arg
    290                 295                 300
Ile Ser Leu Phe Gly Val Leu Ala Arg Gly Gly Thr Ala Tyr Phe Ala
305                 310                 315                 320
Ala Lys Ser Asp Met Ser Thr Leu Phe Glu Asp Ile Gly Leu Val Arg
                325                 330                 335
Pro Thr Glu Ile Phe Phe Val Pro Arg Val Cys Asp Met Val Phe Gln
            340                 345                 350
Arg Tyr Gln Ser Glu Leu Asp Arg Arg Ser Val Ala Gly Ala Asp Leu
    355                 360                 365
Asp Thr Leu Asp Arg Glu Val Lys Ala Asp Leu Arg Gln Asn Tyr Leu
    370                 375                 380
Gly Gly Arg Phe Leu Val Ala Val Val Gly Ser Ala Pro Leu Ala Ala
385                 390                 395                 400
Glu Met Lys Thr Phe Met Glu Ser Val Leu Asp Leu Pro Leu His Asp
                405                 410                 415
Gly Tyr Gly Ser Thr Glu Ala Gly Ala Ser Val Leu Leu Asp Asn Gln
            420                 425                 430
Ile Gln Arg Pro Pro Val Leu Asp Tyr Lys Leu Val Asp Val Pro Glu
    435                 440                 445
Leu Gly Tyr Phe Arg Thr Asp Arg Pro His Pro Arg Gly Glu Leu Leu
450                 455                 460
Leu Lys Ala Glu Thr Thr Ile Pro Gly Tyr Tyr Lys Arg Pro Glu Val
465                 470                 475                 480
Thr Ala Glu Ile Phe Asp Glu Asp Gly Phe Tyr Lys Thr Gly Asp Ile
                485                 490                 495
Val Ala Glu Leu Glu His Asp Arg Leu Val Tyr Val Asp Arg Arg Asn
            500                 505                 510
Asn Val Leu Lys Leu Ser Gln Gly Glu Phe Val Thr Val Ala His Leu
    515                 520                 525
Glu Ala Val Phe Ala Ser Ser Pro Leu Ile Arg Gln Ile Phe Ile Tyr
    530                 535                 540
Gly Ser Ser Glu Arg Ser Tyr Leu Leu Ala Val Ile Val Pro Thr Asp
545                 550                 555                 560
Asp Ala Leu Arg Gly Arg Asp Thr Ala Thr Leu Lys Ser Ala Leu Ala
                565                 570                 575
Glu Ser Ile Gln Arg Ile Ala Lys Asp Ala Asn Leu Gln Pro Tyr Glu
            580                 585                 590
Ile Pro Arg Asp Phe Leu Ile Glu Thr Glu Pro Phe Thr Ile Ala Asn
    595                 600                 605
Gly Leu Leu Ser Gly Ile Ala Lys Leu Leu Arg Pro Asn Leu Lys Glu
610                 615                 620
```

-continued

```
Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
            645                 650                 655

Val Leu Glu Thr Val Ser Arg Ala Ala Lys Ala Met Leu Gly Val Ala
        660                 665                 670

Ser Ala Asp Met Arg Pro Asp Ala His Phe Thr Asp Leu Gly Gly Asp
    675                 680                 685

Ser Leu Ser Ala Leu Ser Phe Ser Asn Leu Leu His Glu Ile Phe Gly
690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
        755                 760                 765

Asp Ser Ile Pro His Ala Pro Val Pro Ala Gln Thr Val Leu Leu Thr
    770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
        835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910

Arg Lys Pro Val Thr Tyr Leu Ser Thr Val Gly Val Ala Asp Gln Val
        915                 920                 925

Asp Pro Ala Glu Tyr Gln Glu Asp Ser Asp Val Arg Glu Met Ser Ala
    930                 935                 940

Val Arg Val Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
            980                 985                 990

Ala Gly Gln Leu Asn Val Gln Asp Val Phe Thr Arg Leu Ile Leu Ser
        995                 1000                1005

Leu Val Ala Thr Gly Ile Ala Pro Tyr Ser Phe Tyr Arg Thr Asp
    1010                1015                1020

Ala Asp Gly Asn Arg Gln Arg Ala His Tyr Asp Gly Leu Pro Ala
    1025                1030                1035
```

```
                                         -continued
Asp Phe Thr Ala Ala Ala Ile Thr Ala Leu Gly Ile Gln Ala Thr
    1040            1045            1050

Glu Gly Phe Arg Thr Tyr Asp Val Leu Asn Pro Tyr Asp Asp Gly
    1055            1060            1065

Ile Ser Leu Asp Glu Phe Val Asp Trp Leu Val Glu Ser Gly His
    1070            1075            1080

Pro Ile Gln Arg Ile Thr Asp Tyr Ser Asp Trp Phe His Arg Phe
    1085            1090            1095

Glu Thr Ala Ile Arg Ala Leu Pro Glu Lys Gln Arg Gln Ala Ser
    1100            1105            1110

Val Leu Pro Leu Leu Asp Ala Tyr Arg Asn Pro Cys Pro Ala Val
    1115            1120            1125

Arg Gly Ala Ile Leu Pro Ala Lys Glu Phe Gln Ala Ala Val Gln
    1130            1135            1140

Thr Ala Lys Ile Gly Pro Glu Gln Asp Ile Pro His Leu Ser Ala
    1145            1150            1155

Pro Leu Ile Asp Lys Tyr Val Ser Asp Leu Glu Leu Leu Gln Leu
    1160            1165            1170

Leu
```